United States Patent
Lindquist et al.

(10) Patent No.: US 9,790,188 B2
(45) Date of Patent: Oct. 17, 2017

(54) BENZIMIDAZOLE DERIVATIVES AND USES THEREOF

(71) Applicants: Whitehead Institute for Biomedical Research, Cambridge, MA (US); Massachusetts Institute of Technology, Cambridge, MA (US)

(72) Inventors: Susan L. Lindquist, Cambridge, MA (US); Stephen L. Buchwald, Newton, MA (US); Daniel Tardiff, Arlington, MA (US); Nathan Jui, Cambridge, MA (US)

(73) Assignees: Whitehead Institute for Biomedical Research, Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/776,184

(22) PCT Filed: Mar. 17, 2014

(86) PCT No.: PCT/US2014/030733
§ 371 (c)(1),
(2) Date: Sep. 14, 2015

(87) PCT Pub. No.: WO2014/145887
PCT Pub. Date: Sep. 18, 2014

(65) Prior Publication Data
US 2016/0031824 A1    Feb. 4, 2016

Related U.S. Application Data

(60) Provisional application No. 61/794,870, filed on Mar. 15, 2013.

(51) Int. Cl.
| | | |
|---|---|---|
| C07D 235/04 | (2006.01) |
| A61K 31/4184 | (2006.01) |
| C07D 235/16 | (2006.01) |
| A61K 45/06 | (2006.01) |
| A61K 31/4439 | (2006.01) |
| C07D 235/08 | (2006.01) |
| C07D 401/12 | (2006.01) |
| C07D 403/04 | (2006.01) |
| C07D 405/04 | (2006.01) |
| C07D 409/12 | (2006.01) |

(52) U.S. Cl.
CPC ........ *C07D 235/16* (2013.01); *A61K 31/4184* (2013.01); *A61K 31/4439* (2013.01); *A61K 45/06* (2013.01); *C07D 235/08* (2013.01); *C07D 401/12* (2013.01); *C07D 403/04* (2013.01); *C07D 405/04* (2013.01); *C07D 409/12* (2013.01)

(58) Field of Classification Search
None
See application file for complete search history.

(56) References Cited

U.S. PATENT DOCUMENTS

| | | |
|---|---|---|
| 2002/0151550 A1 | 10/2002 | Desimone et al. |
| 2006/0035951 A1 | 2/2006 | Bolger et al. |
| 2006/0116402 A1 | 6/2006 | Crew et al. |
| 2008/0207720 A1 | 8/2008 | Moinet et al. |

(Continued)

FOREIGN PATENT DOCUMENTS

| | | |
|---|---|---|
| CN | 1838950 | 9/2006 |
| CN | 101193867 | 6/2008 |
| CN | 102573837 | 7/2012 |

(Continued)

OTHER PUBLICATIONS

Purandare et al, Tetrahedron Letters (2002), 43(21), 3903-3906.*
Wu et al., Toxicology, 236, pp. 1-6, 2007.*
International Search Report and Written Opinion, mailed Aug. 20, 2014, in connection with PCT/US2014/030733.
International Preliminary Report on Patentability, mailed Sep. 24, 2015, in connection with PCT/ US2014/030733.
Choi et al., Antidiabetic actions of a non-agonist PPARγ ligand blocking Cdk5-mediated phosphorylation. Nature. Sep. 4, 2011;477(7365):477-81. doi: 10.1038/nature10383.

(Continued)

*Primary Examiner* — Zinna Northington Davis
(74) *Attorney, Agent, or Firm* — Wolf, Greenfield & Sacks, P.C.

(57) ABSTRACT

The present invention provides novel compounds of Formula (I), and pharmaceutically acceptable salts, solvates, hydrates, polymorphs, co-crystals, tautomers, stereoisomers, isotopically labeled derivatives, prodrugs, and pharmaceutical compositions thereof. The present invention also provides methods and kits using the inventive compounds and pharmaceutical compositions for treating and/or preventing diseases associated with protein aggregation, such as amyloidoses (e.g., Parkinson's disease and Alzheimer's disease), treating and/or preventing neurodegenerative diseases, treating and/or preventing diseases associated with Tar DNA binding protein 43 kDa, reducing or preventing protein aggregation, and/or modulating E3 ubiquitin ligase in a subject in need thereof.

(I)

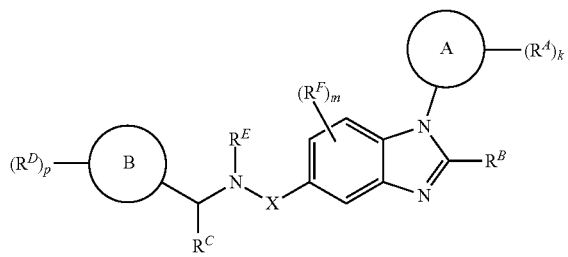

10 Claims, 38 Drawing Sheets

(56) References Cited

U.S. PATENT DOCUMENTS

| | | |
|---|---|---|
| 2011/0028527 A1 | 2/2011 | Chiang et al. |
| 2012/0115881 A1 | 5/2012 | Lee et al. |

FOREIGN PATENT DOCUMENTS

| | | |
|---|---|---|
| WO | WO 2002/042278 A2 | 5/2002 |
| WO | WO 2003/099811 A1 | 12/2003 |
| WO | WO 2005/021531 A1 | 3/2005 |
| WO | WO 2007/043653 A1 | 4/2007 |
| WO | WO 2011/005052 A2 | 1/2011 |
| WO | WO 2012/080729 A2 | 6/2012 |
| WO | WO 2013/078233 A1 | 5/2013 |

OTHER PUBLICATIONS

Su et al., Compounds from an unbiased chemical screen reverse both ER-to-Golgi trafficking defects and mitochondrial dysfunction in Parkinson's disease models. Dis Model Mech. Mar.-Apr. 2010;3(3-4):194-208. doi: 10.1242/dmm.004267. Epub Dec. 28. 2009.

Tardiff et al., Different 8-hydroxyquinolines protect models of TDP-43 protein, α-synuclein, and polyglutamine proteotoxicity through distinct mechanisms. J Biol Chem. Feb. 3, 2012;287(6):4107-20. doi: 10.1074/jbc.M111.308668. Epub Dec. 6, 2011.

[No Author Listed], RN 4514-96-79-0, 4514-96-98-3, 4514-98-00-3. STN on the Web, Database Chemical Library. Sep. 16, 2002.

Extended European Search Report, dated Nov. 23, 2016, in connection with EP 14764542.8.

Koel et al., Substitutions near the receptor binding site determine major antigenic change during influenza virus evolution. Science. Nov. 22, 2013;342(6161):976-9. doi: 10.1126/science.1244730.

Tardiff et al., Yeast reveal a "druggable" Rsp5/Nedd4 network that ameliorates α-synuclein toxicity in neurons. Science. Nov. 22, 2013;342(6161):979-83. doi:10.1126/science.1245321. Epub Oct. 24, 2013.

\* cited by examiner

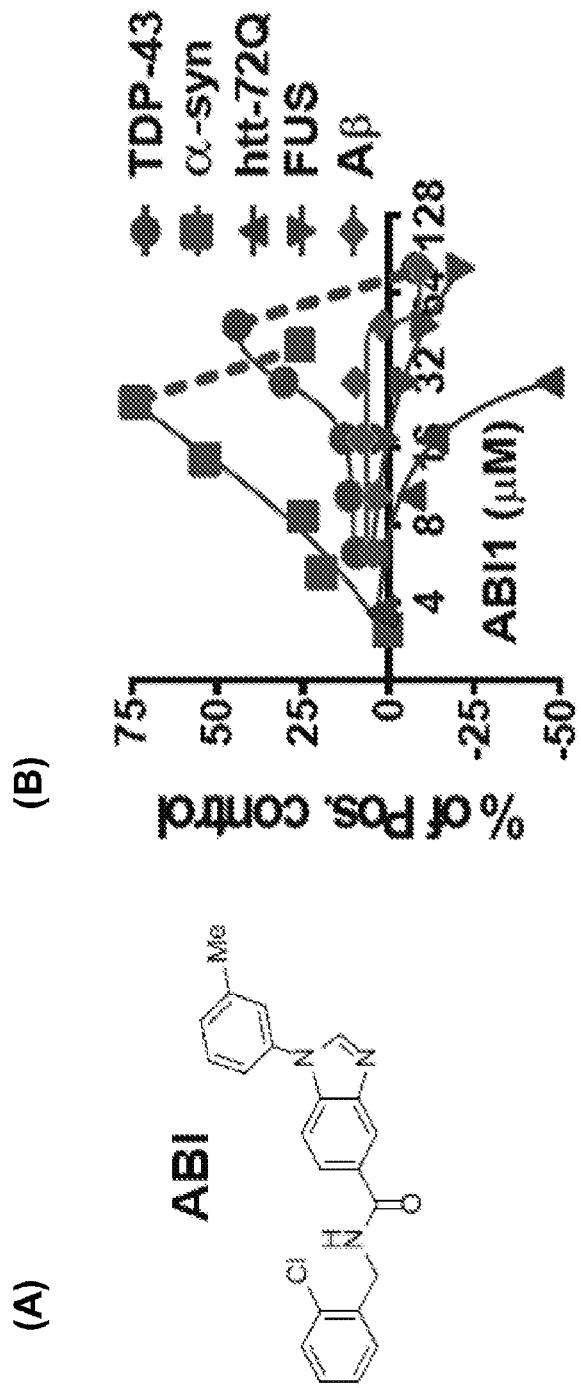
Figure 1A-B

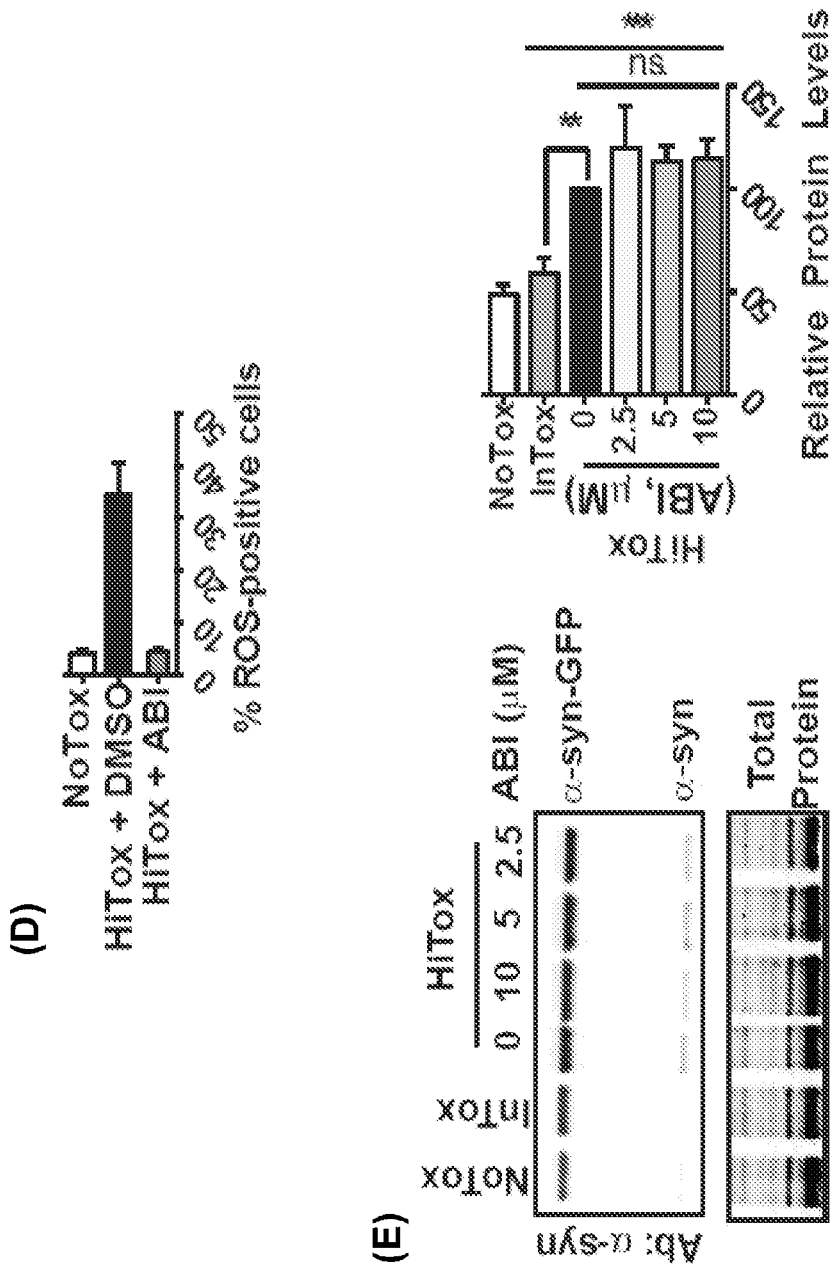
Figure 1D-E

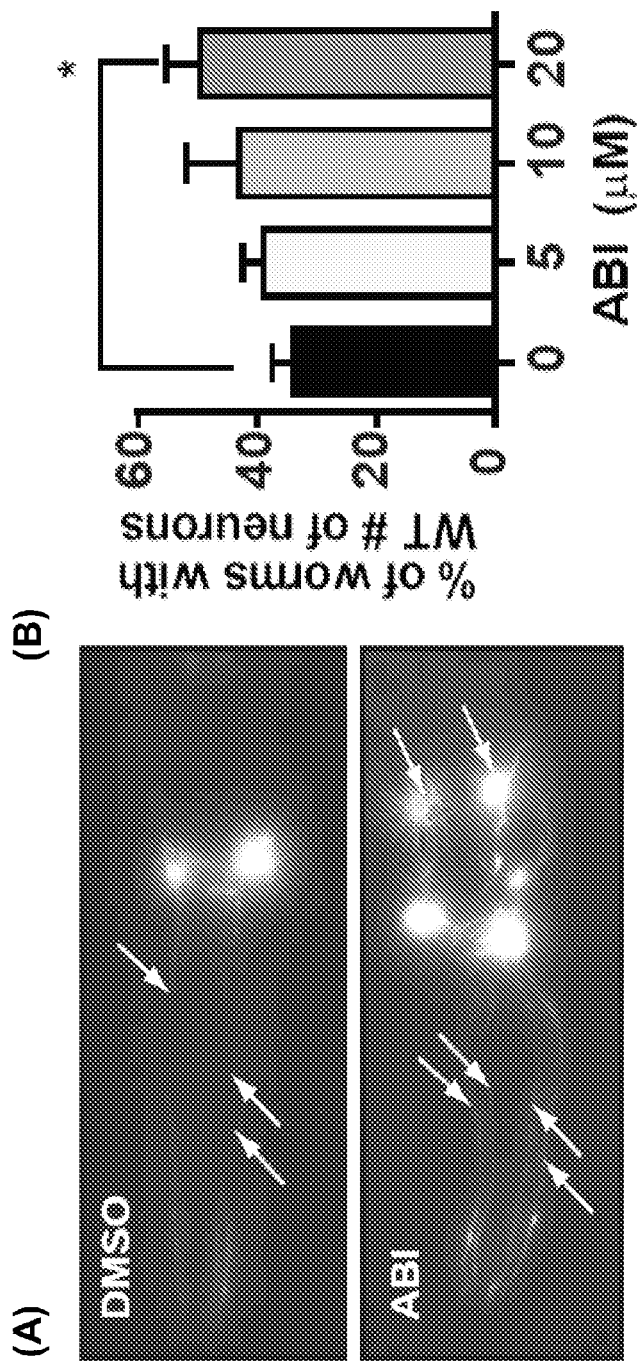
Figure 2A-B

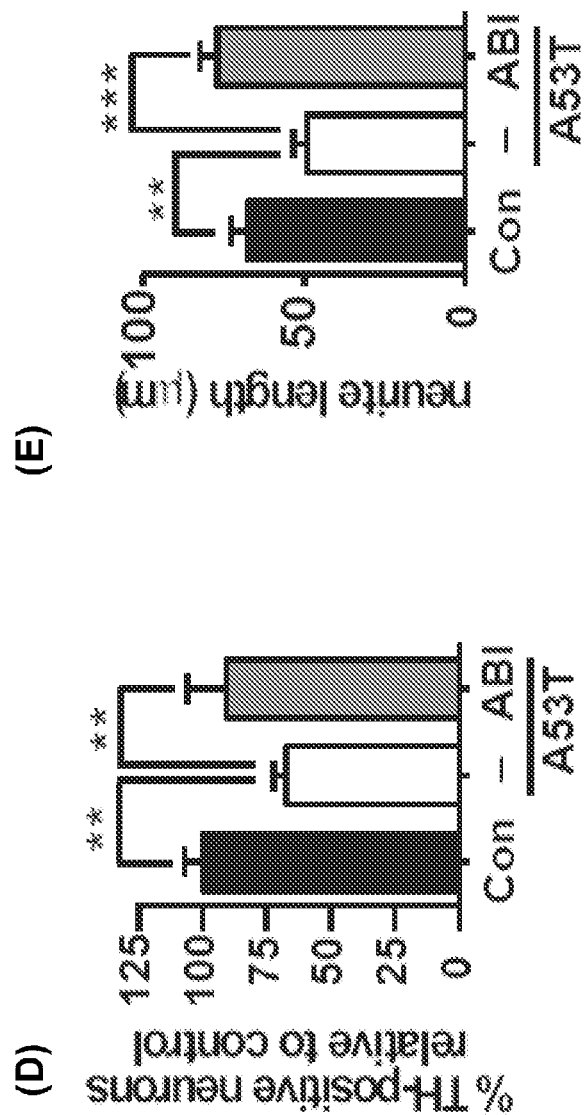
Figure 2D-E

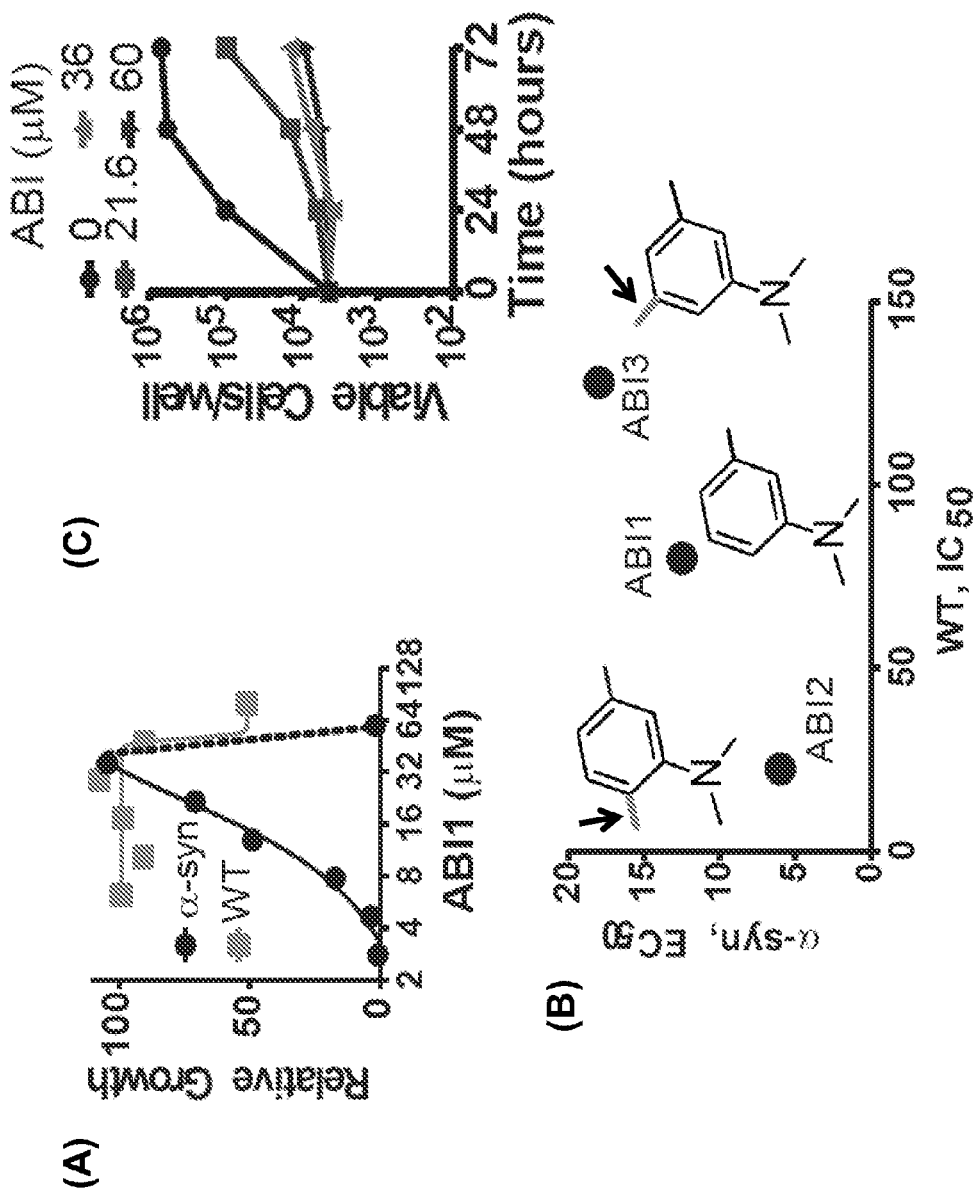
Figure 3A-C

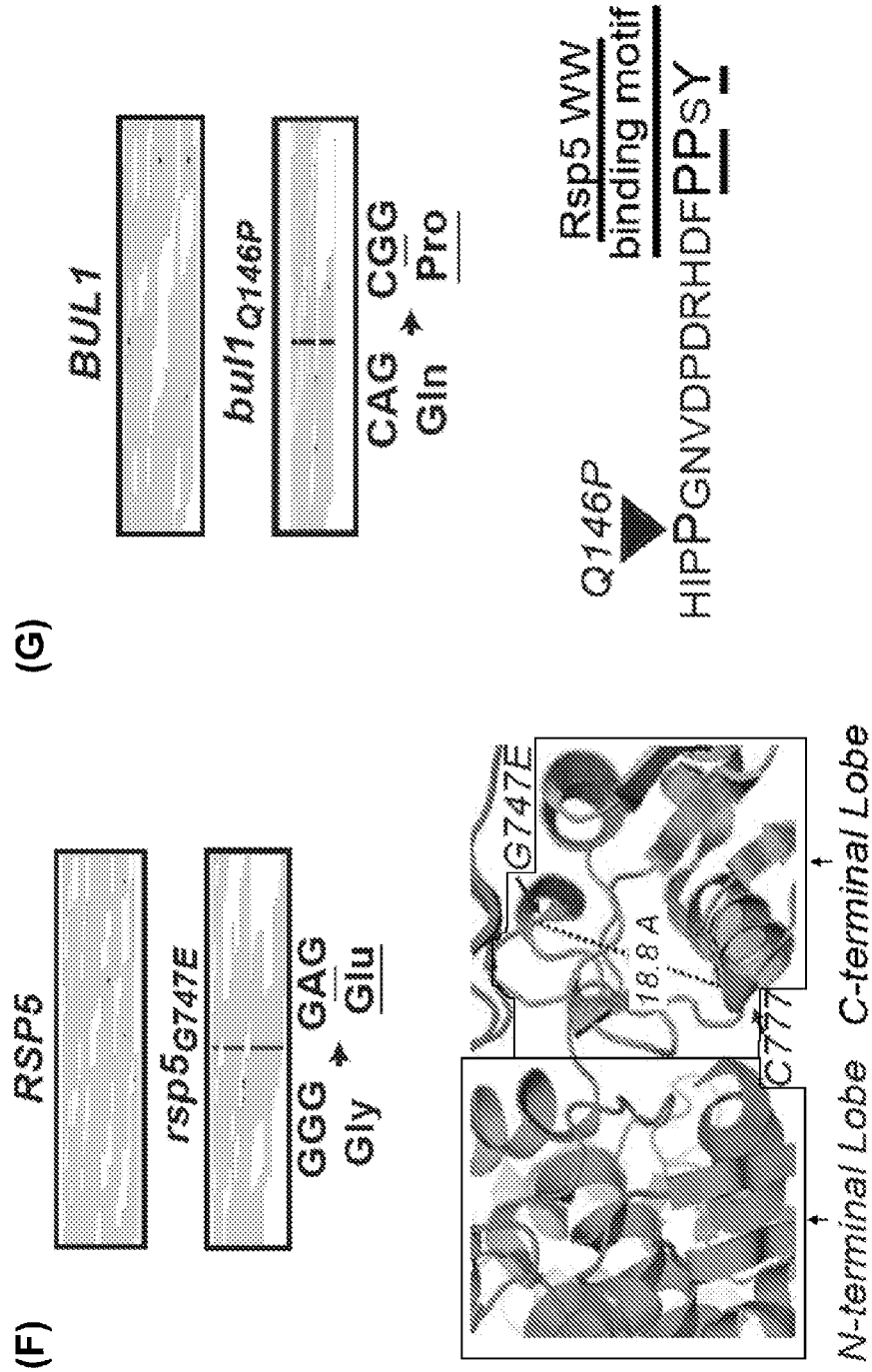
Figure 3F-G

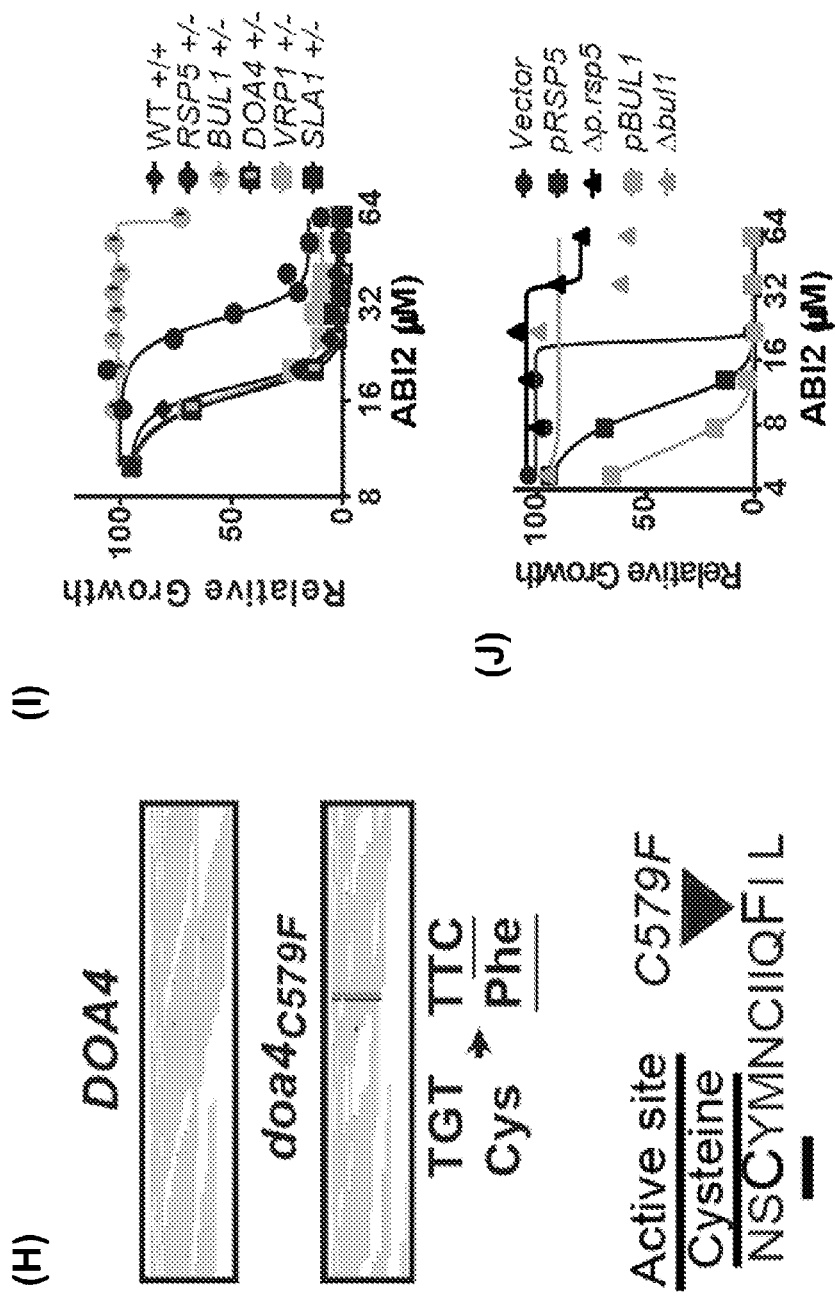
Figure 3H-J

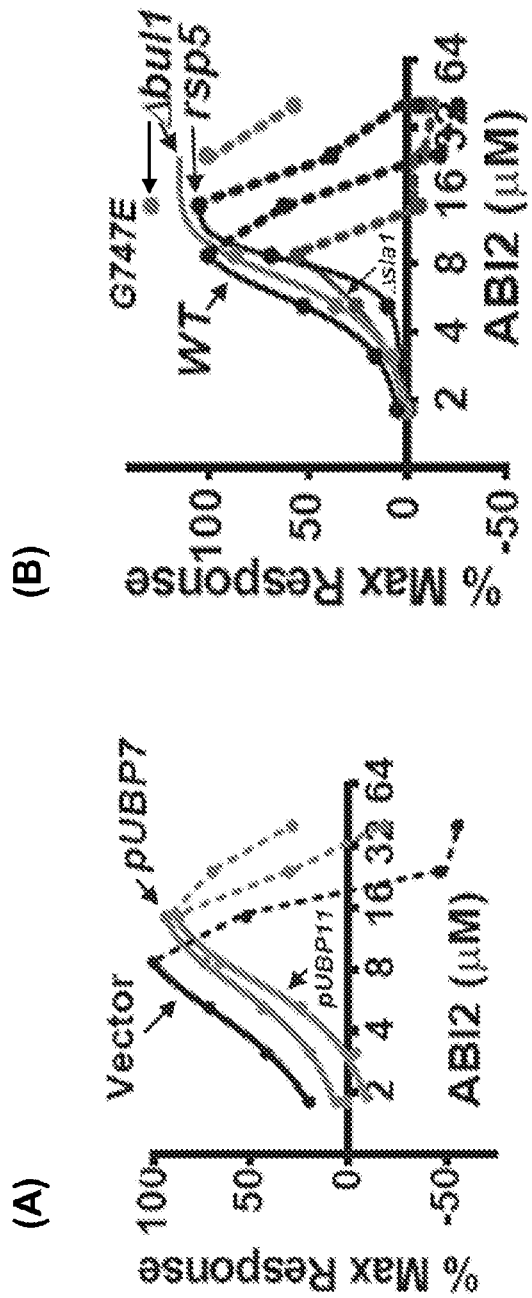
Figure 4A-B

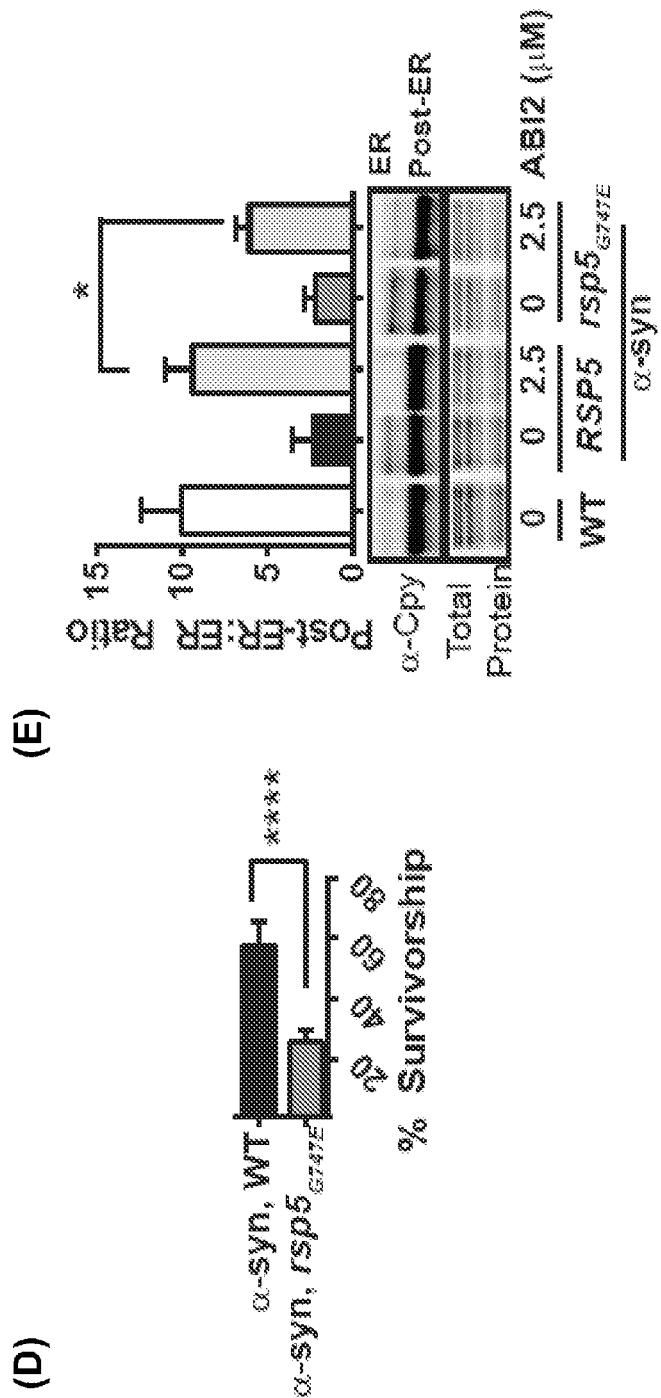
Figure 4D-E

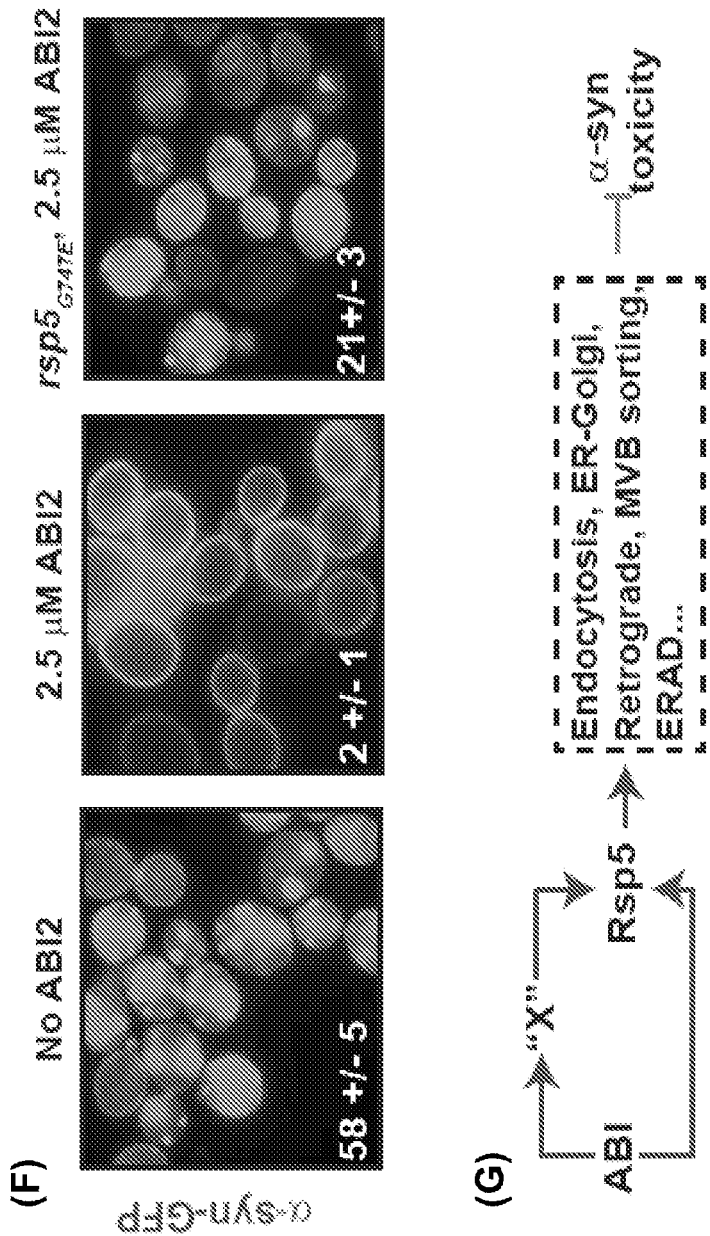
Figure 4F-G

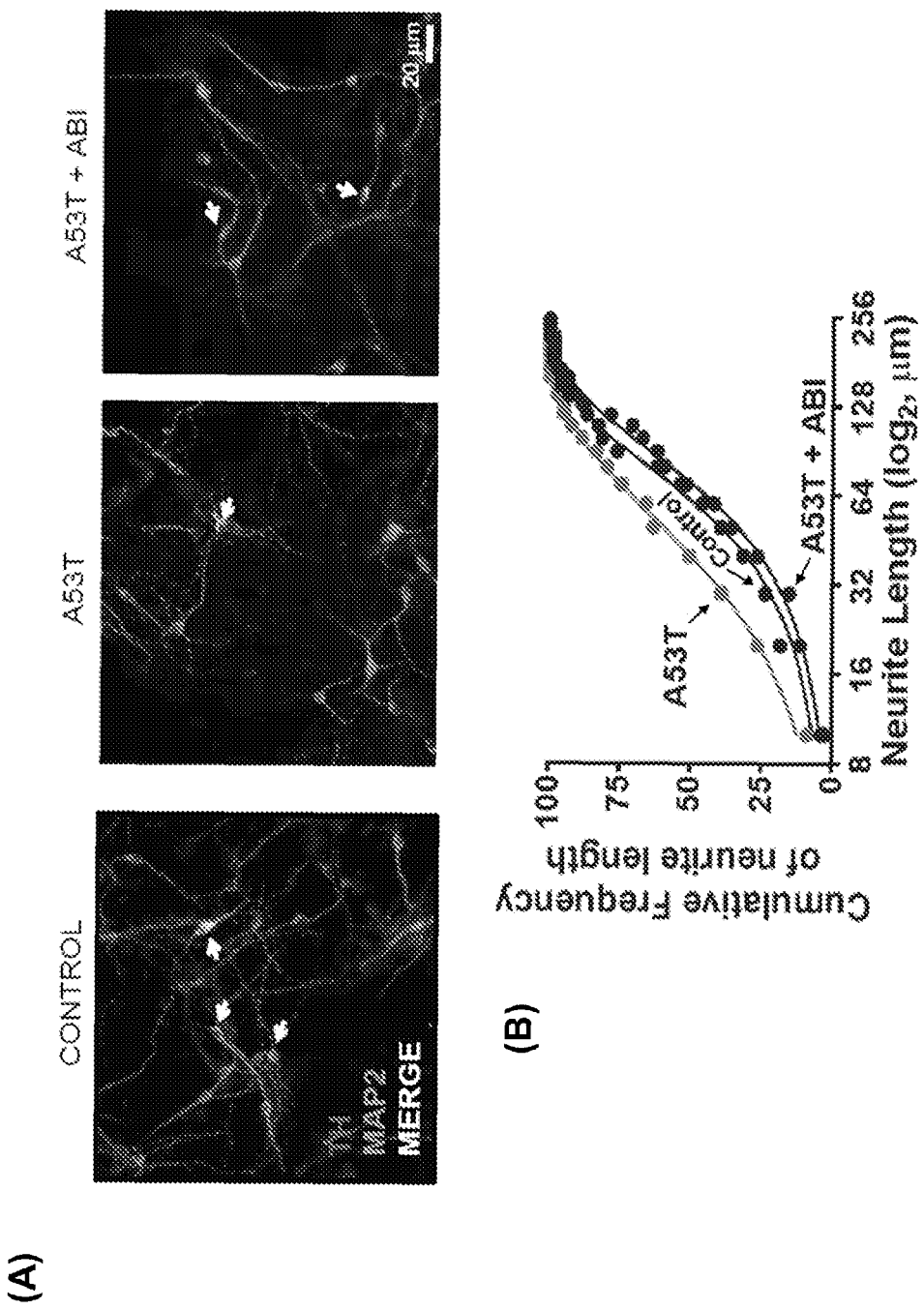
Figure 5A-B

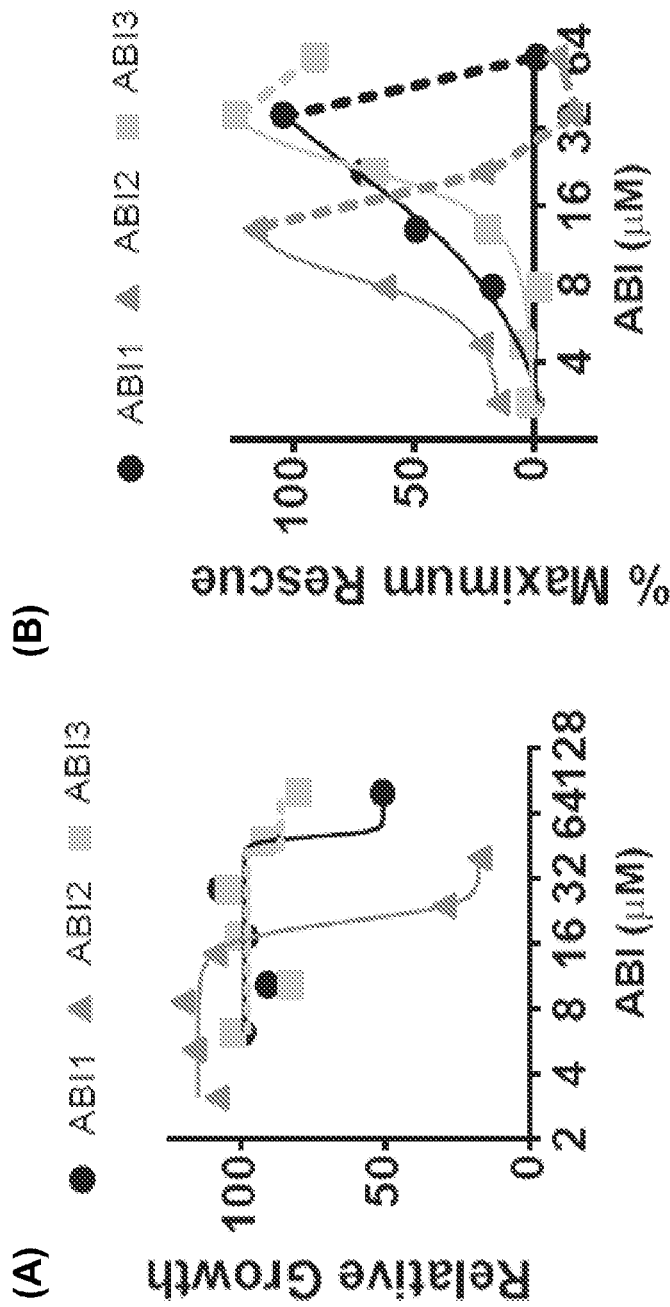
Figure 6A-B

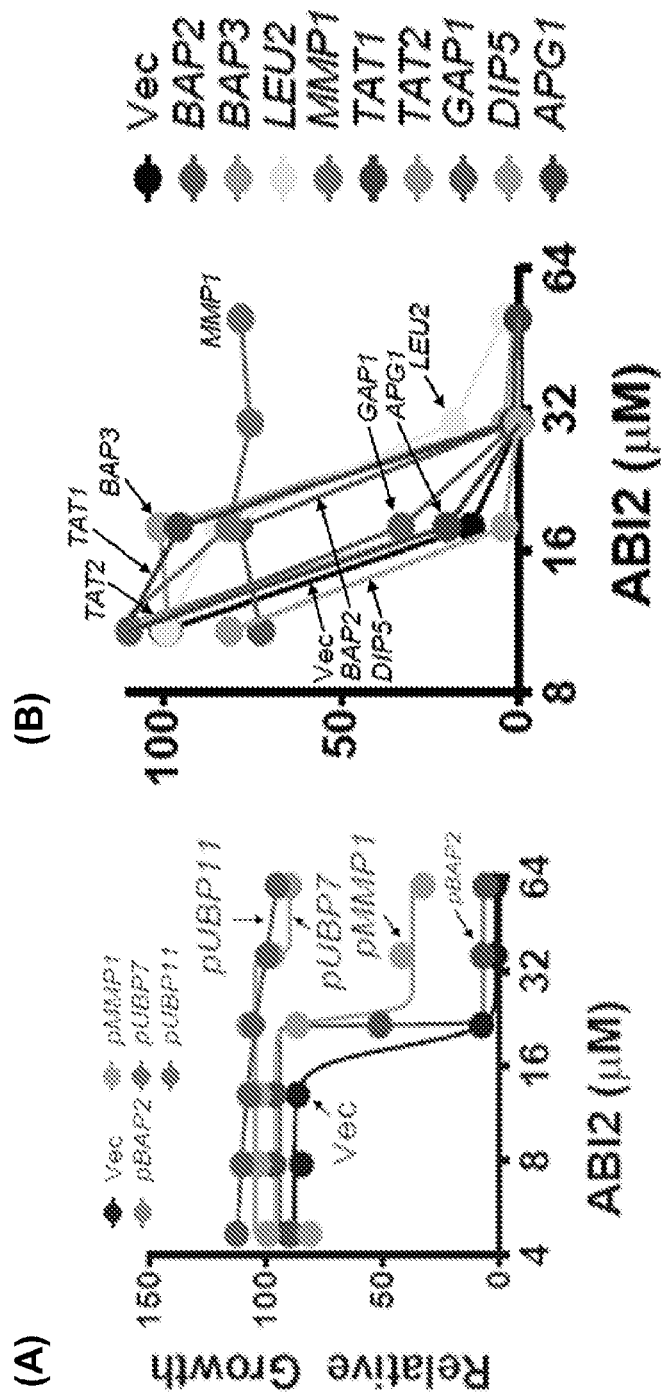
Figure 7A-B

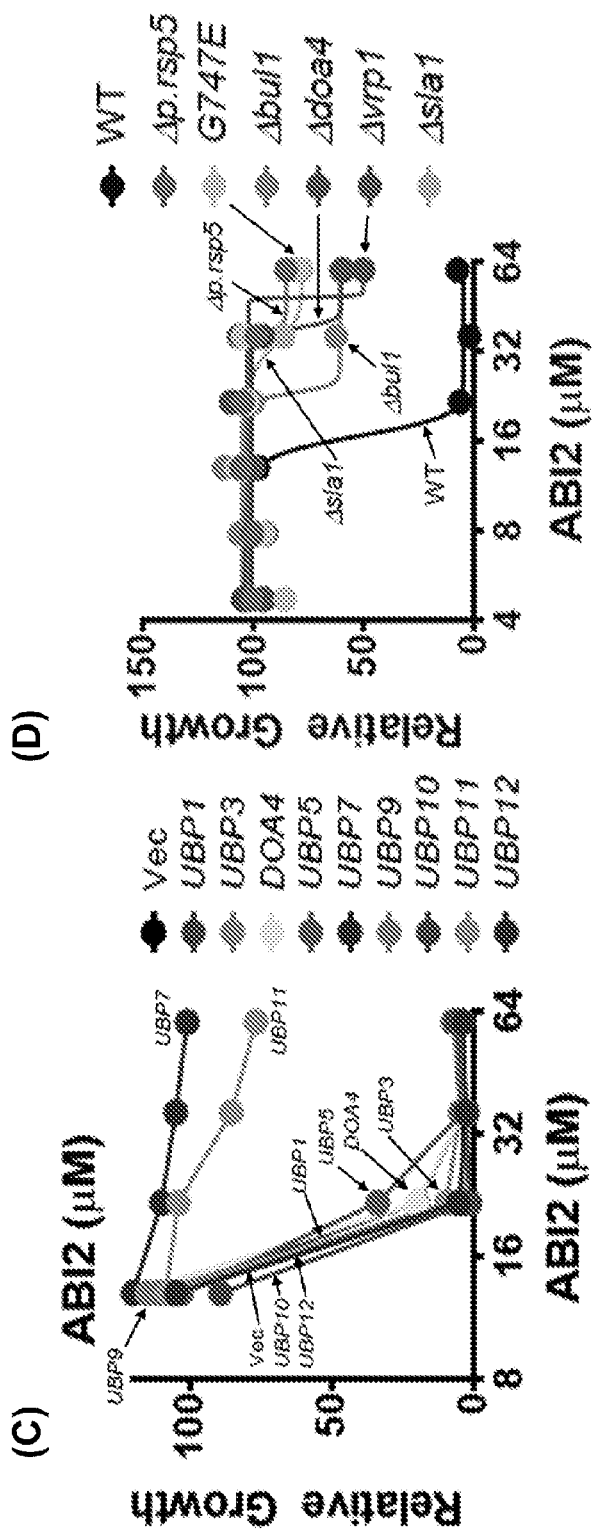
Figure 7C-D

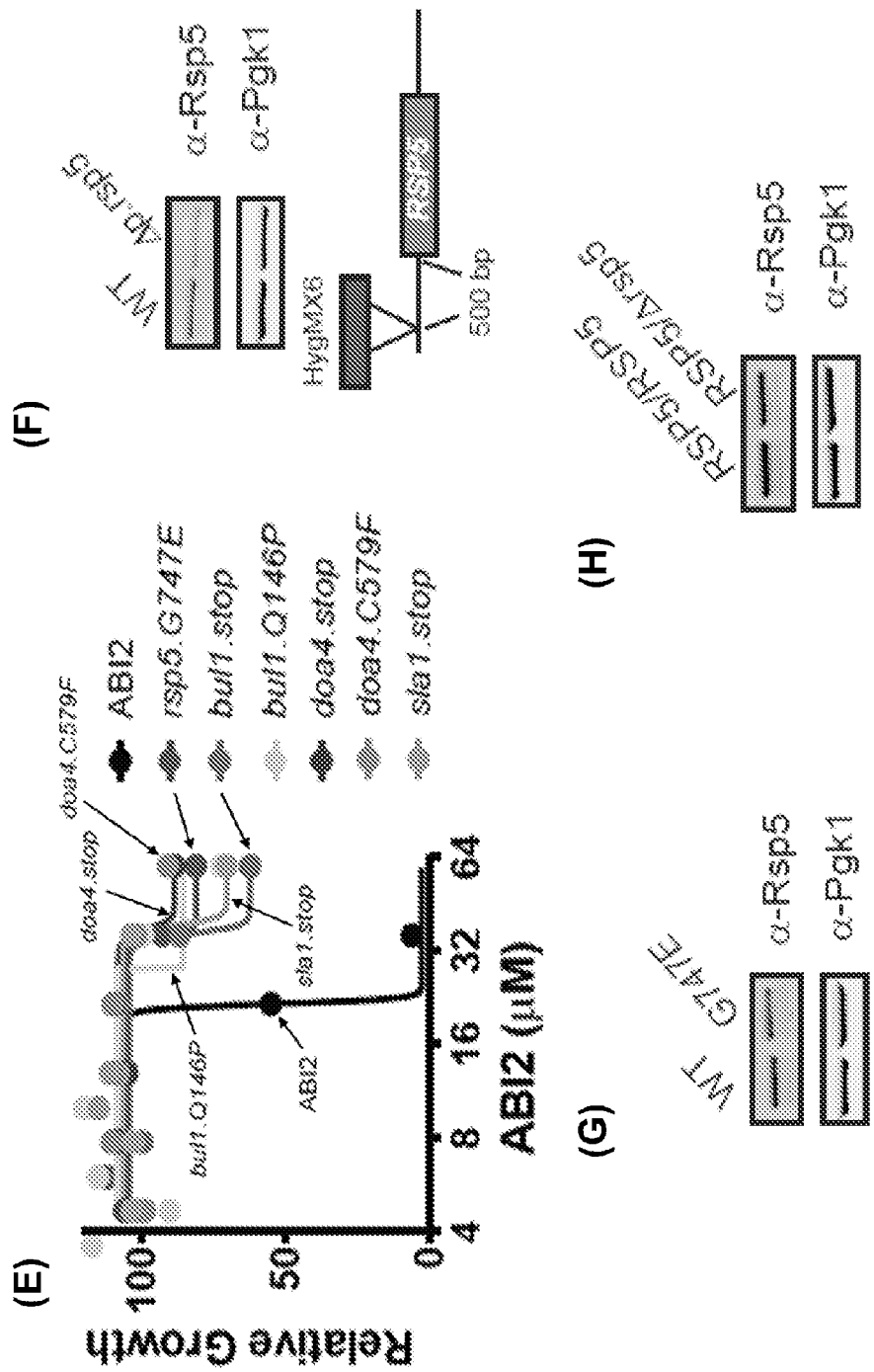
Figure 7E-H

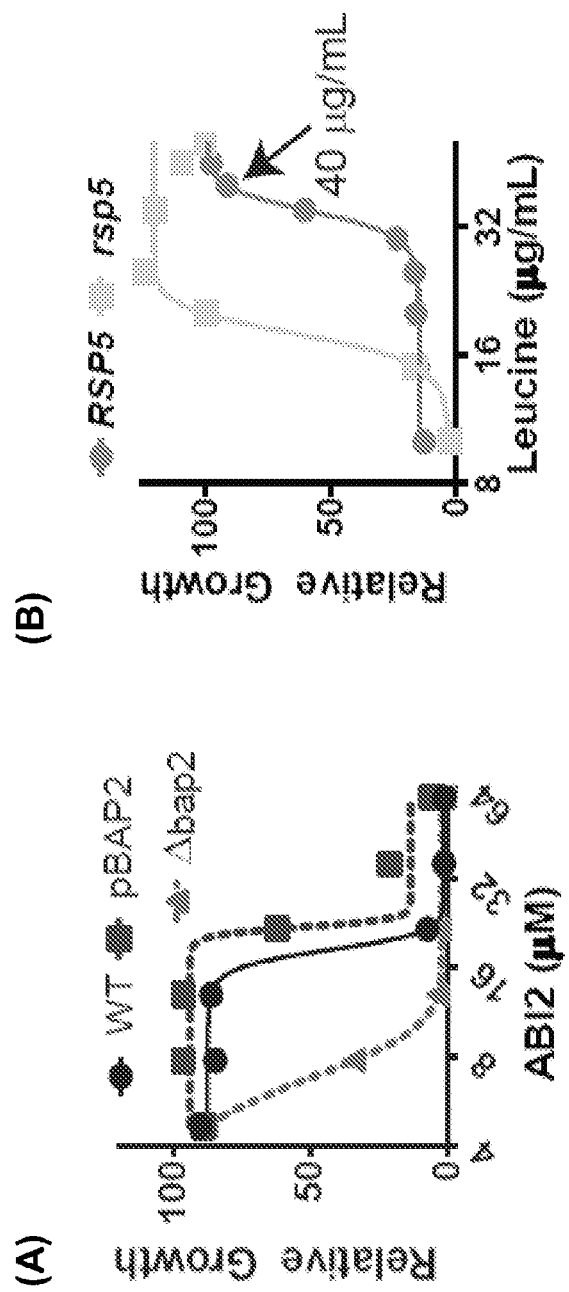
Figure 9A-B

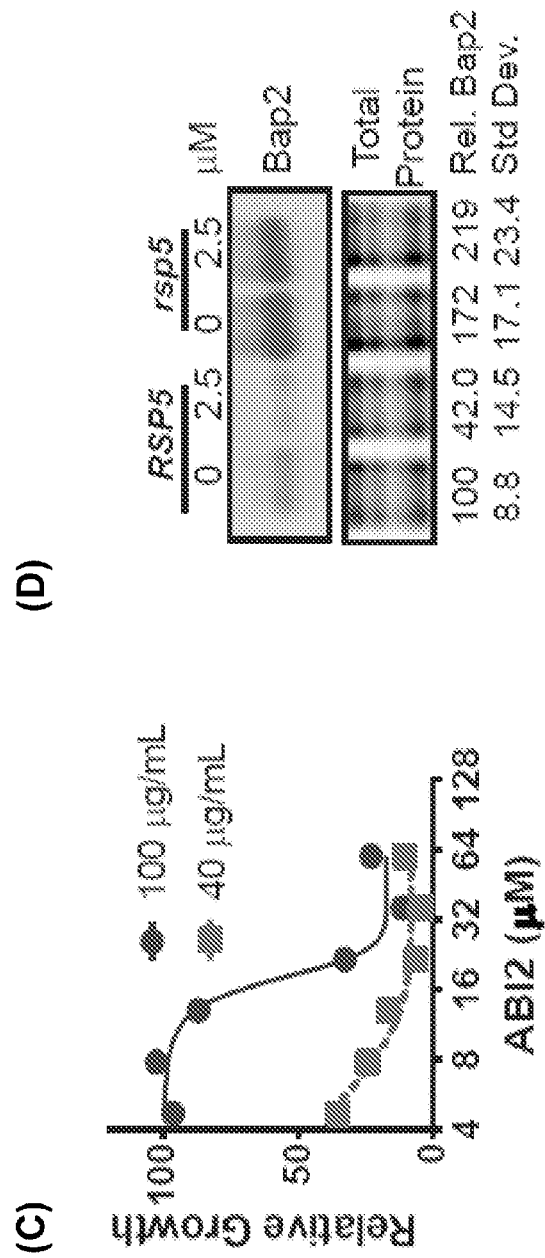
Figure 9C-D

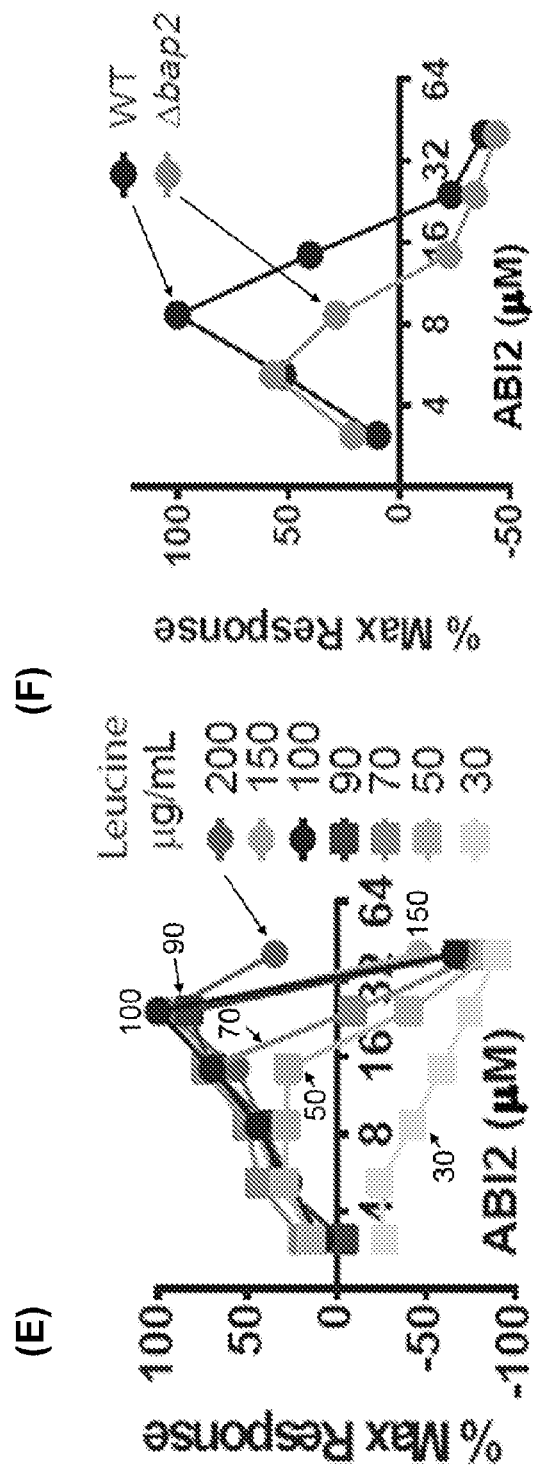
Figure 9E-F

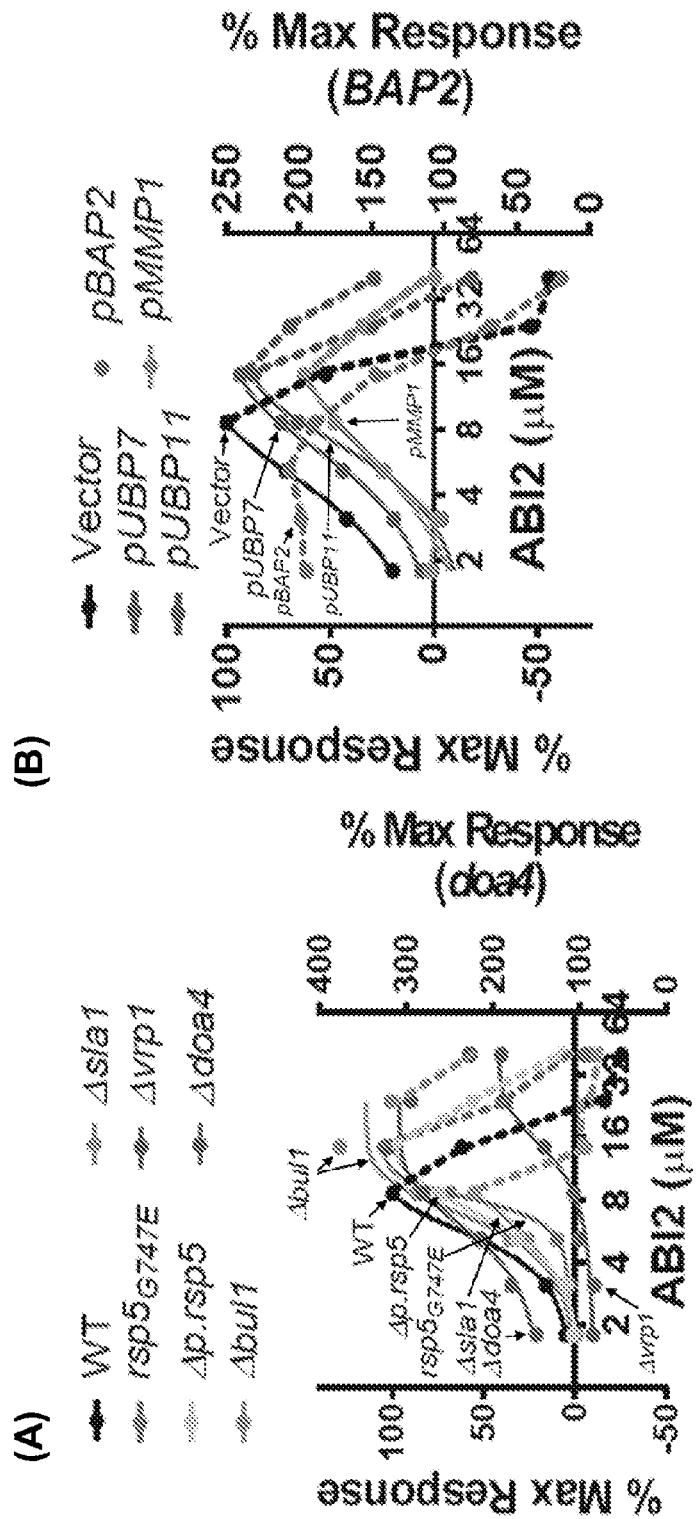
Figure 10A-B

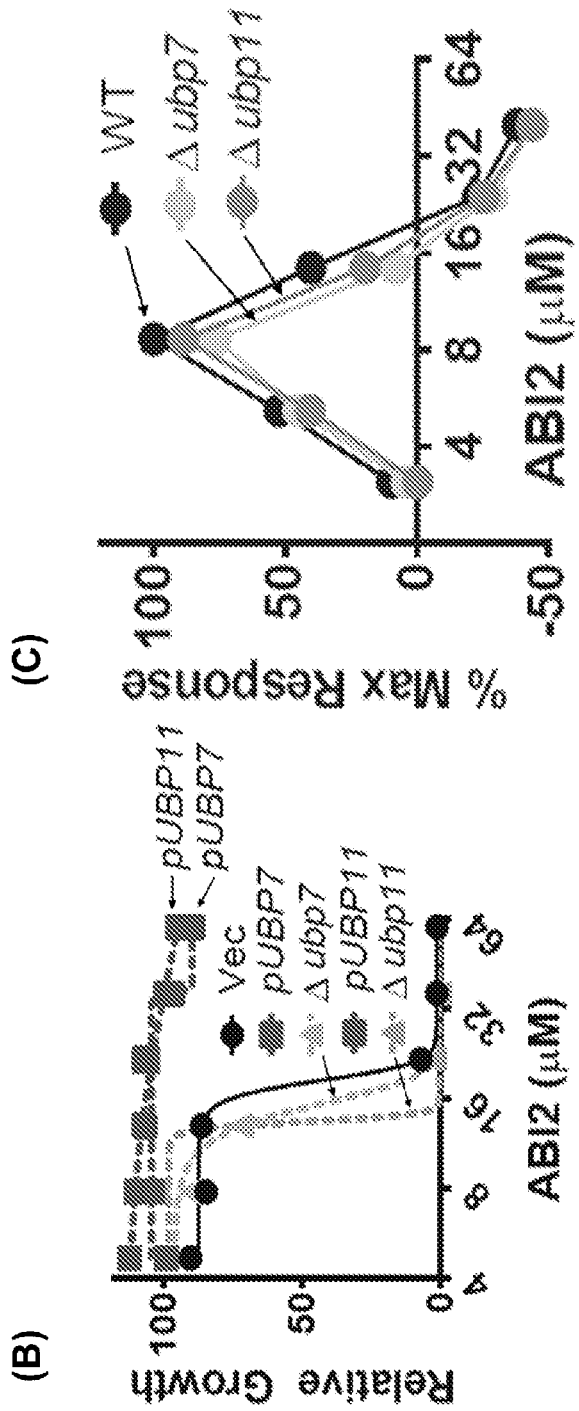
Figure 11B-C

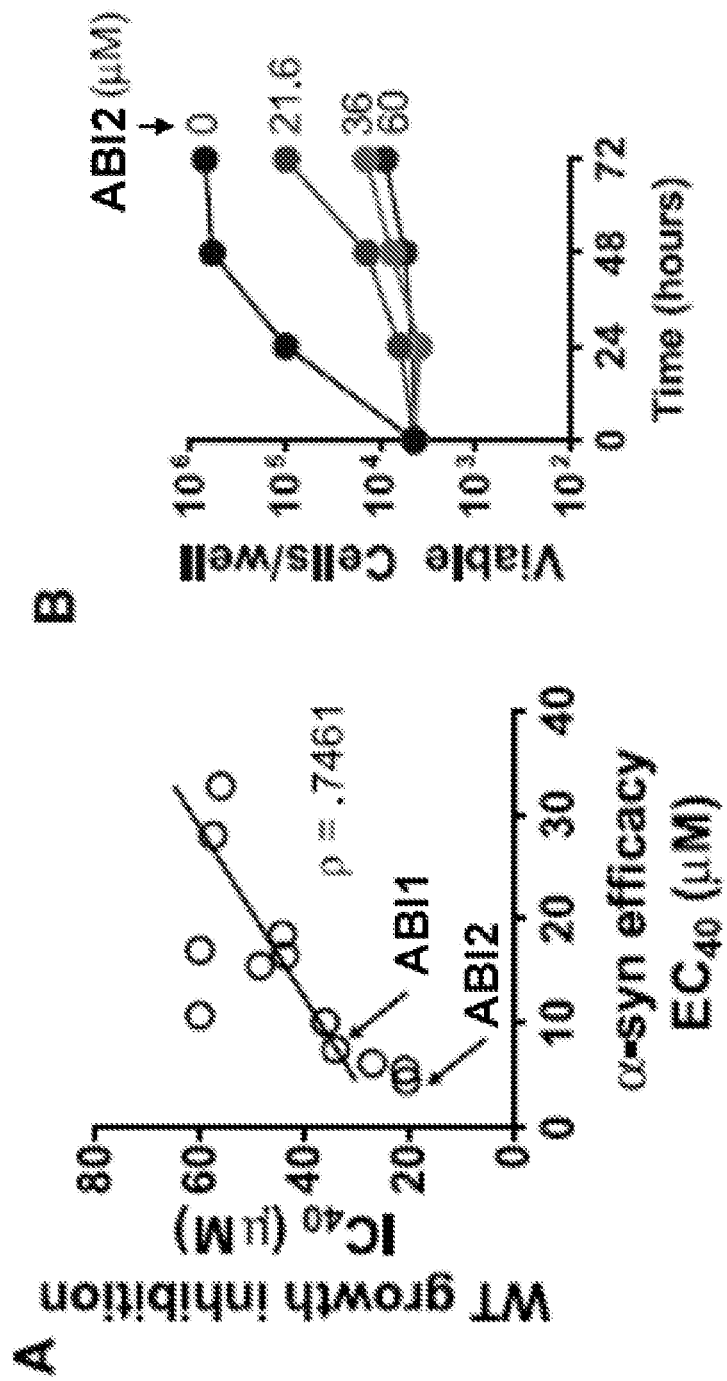
Figure 13A-B

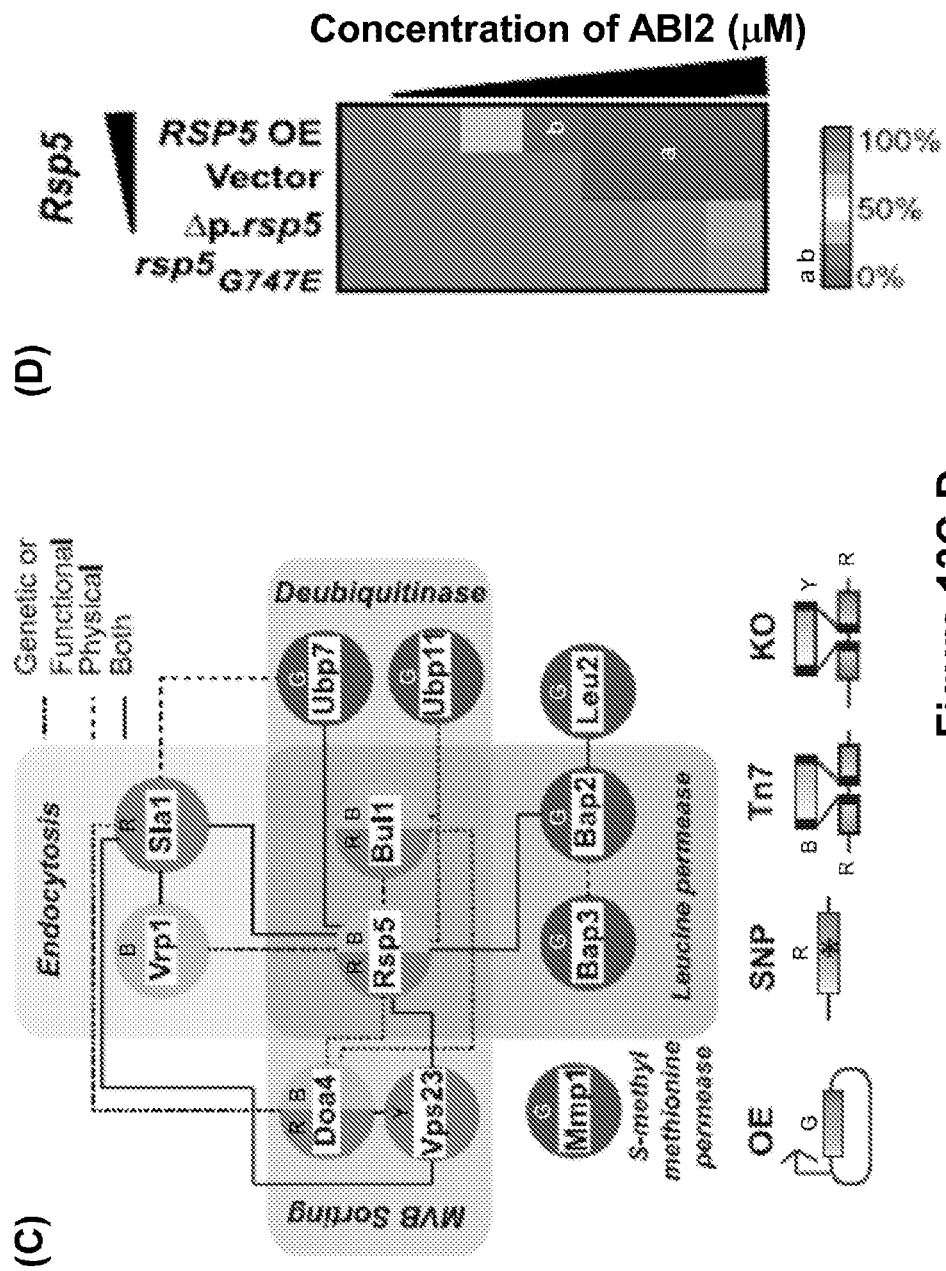
Figure 13C-D

BENZIMIDAZOLE DERIVATIVES AND USES THEREOF

RELATED APPLICATIONS

The present application is a national stage filing under 35 U.S.C. §371 of international PCT application, PCT/US2014/030733, filed Mar. 17, 2014, which claims priority under 35 U.S.C. §119(e) to U.S. provisional patent application, U.S. Ser. No. 61/794,870, filed Mar. 15, 2013, each of which is incorporated herein by reference.

GOVERNMENT SUPPORT

This invention was made with Government support under Grant No. R01 GM058160 awarded by the National Institutes of Health. The Government has certain rights in the invention.

BACKGROUND OF THE INVENTION

An incomplete understanding of the molecular perturbations that cause disease, as well as a limited arsenal of robust model systems, has contributed to the failure to generate successful disease-modifying therapies against common and progressive neurodegenerative diseases (ND), such as Parkinson's Disease (PD) and Alzheimer's Disease (AD). These limitations, combined with commonly-assumed restrictions on the "druggable" proteome, present a major challenge for target-based drug discovery. Despite the predominance of this strategy, in the past 15 years, unbiased phenotypic screens have identified greater than 50% more new chemical entities with new mechanisms of action (MOA) than target-based screens (1). This success has sparked renewed interest in unbiased cell-based screens for compounds that work in unanticipated ways (2). In the context of NDs, establishing neuronal screening platforms is exceptionally challenging (3). However, when neuronal pathologies derive from perturbations of conserved eukaryotic processes, simpler cell-based models offer a potential solution. Modeling the cellular pathologies that underlie α-synucleinopathies (including PD) in yeast recapitulates the derangements in protein trafficking and mitochondrial dysfunction that are seen in neurons and PD patients (4). The ease of yeast culture and the robust growth phenotypes induced by α-synuclein greatly facilitate high-throughput compound screening (3, 4). While phenotypic screens are unbiased, the formidable challenge of deciphering MOA can limit the advancement of lead compounds by impeding target-guided medicinal chemistry and early clinical evaluation of on-target efficacy. Therefore, there is a need to identify compounds that address underlying cellular pathologies in NDs and to define the specific target space in which they act.

SUMMARY OF THE INVENTION

Novel benzimidazole derivatives, such as compounds of Formula (I) (e.g., ABI, shown below and in FIG. 1A), are discovered that strongly and specifically protected yeast and neuronal models from the PD protein, α-synuclein (α-syn).

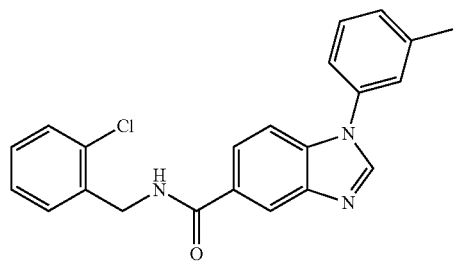

In one aspect, the present invention provides compounds of Formula (I):

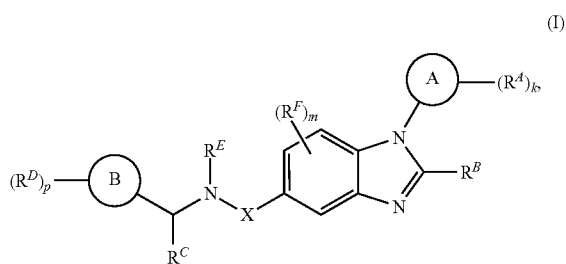

and pharmaceutically acceptable salts, solvates, hydrates, polymorphs, co-crystals, tautomers, stereoisomers, isotopically labeled derivatives, and prodrugs thereof, wherein Ring A, Ring B, X, $R^A$, $R^B$, $R^C$, $R^D$, $R^E$, $R^F$, k, m, and p are as defined herein.

Exemplary compounds of Formula (I) include, but are not limited to:

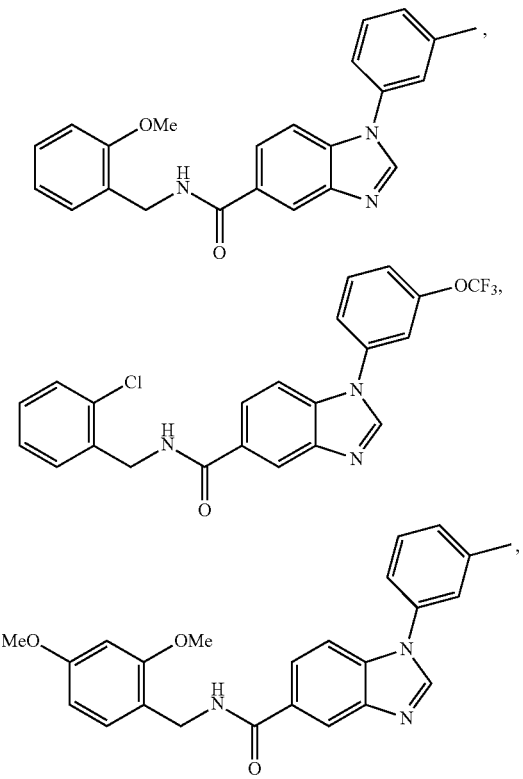

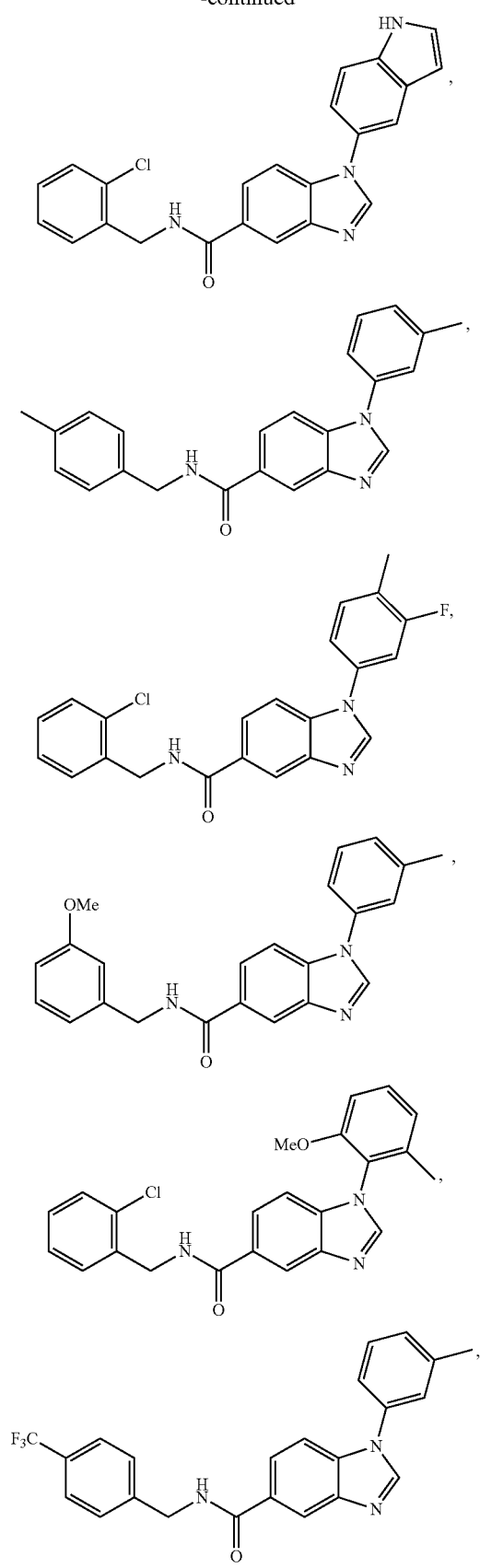
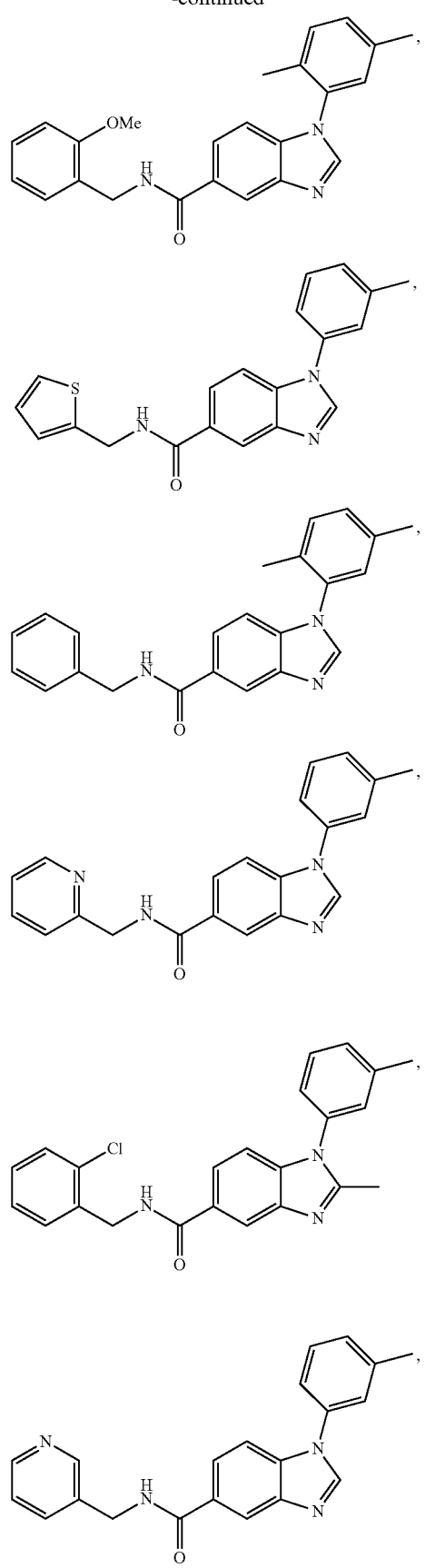

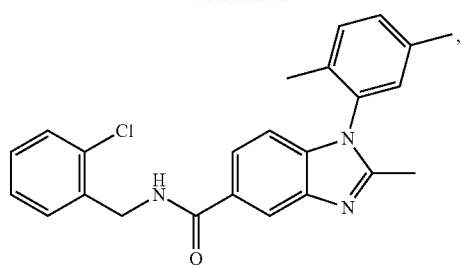
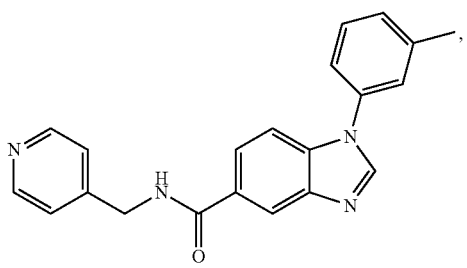
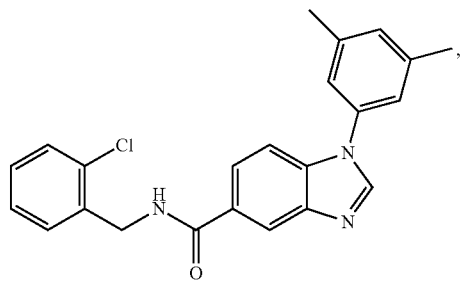
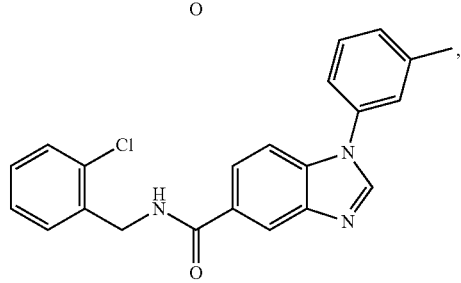
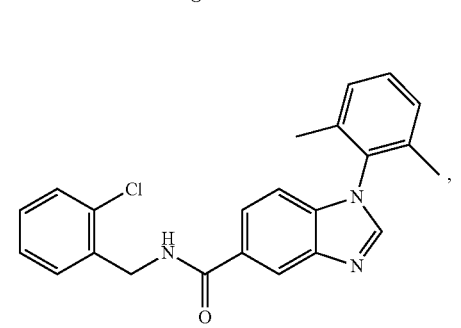
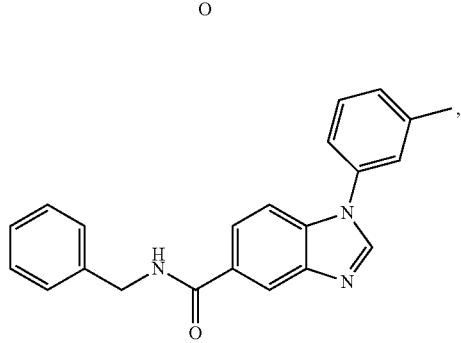
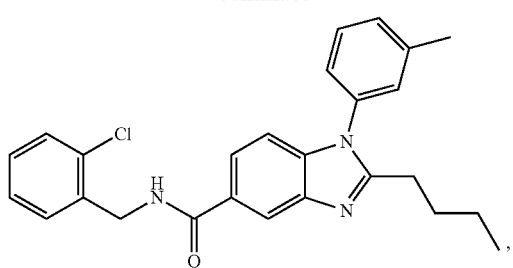
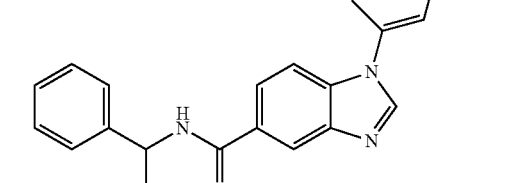
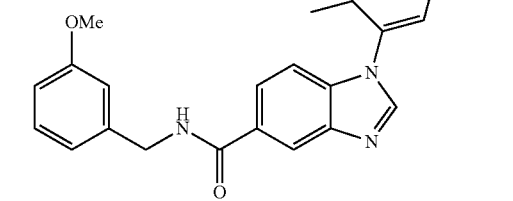
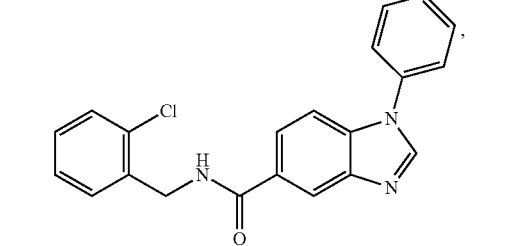
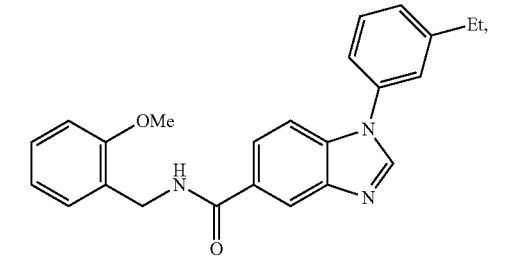
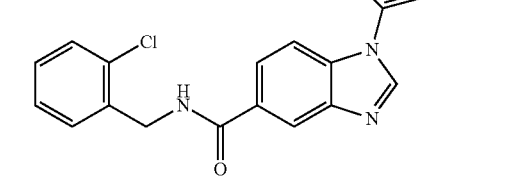

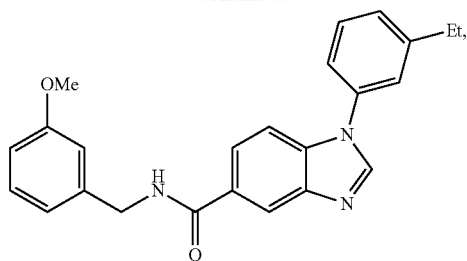
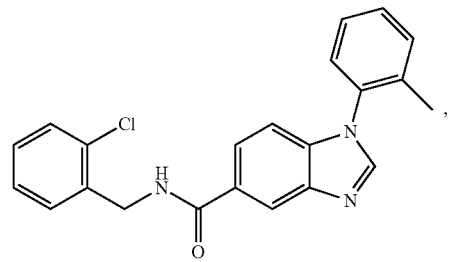
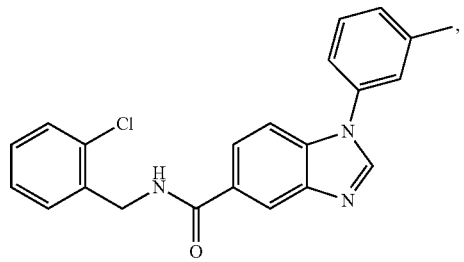
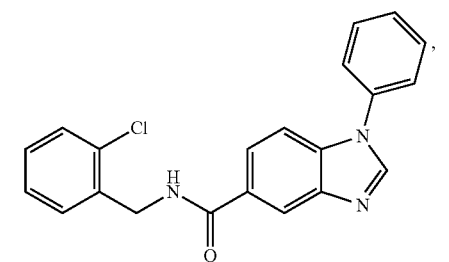
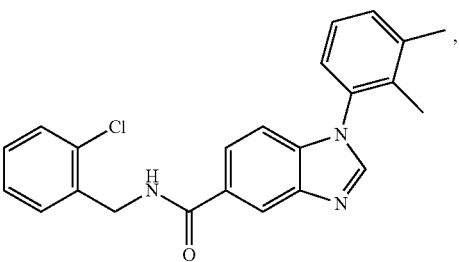
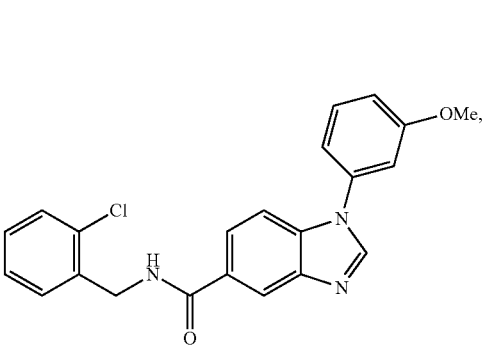
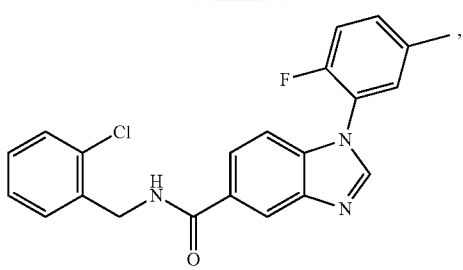
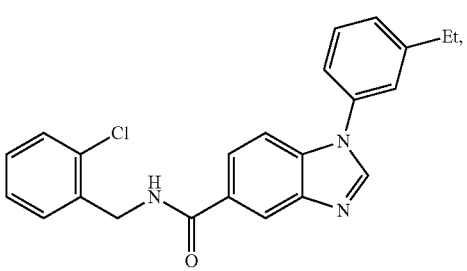
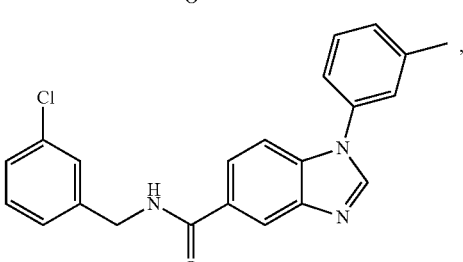
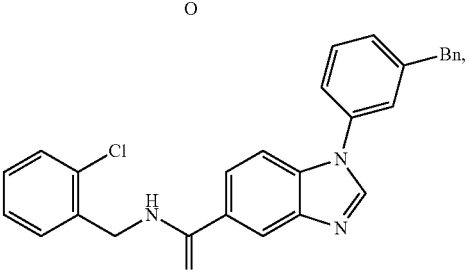
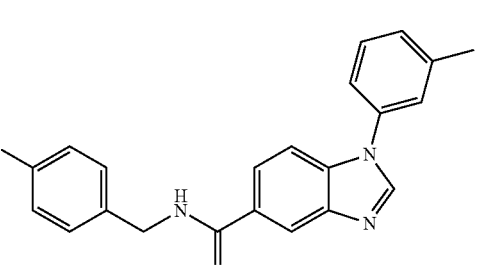
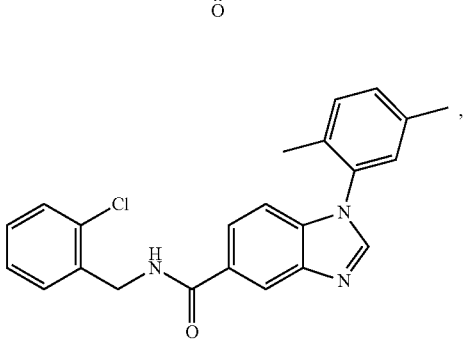

-continued

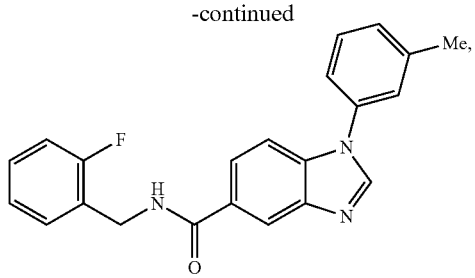

and pharmaceutically acceptable salts, solvates, hydrates, polymorphs, co-crystals, tautomers, stereoisomers, isotopically labeled derivatives, and prodrugs thereof.

In another aspect, the present invention provides pharmaceutical compositions comprising a compound of the invention, and optionally a pharmaceutically acceptable excipient. In certain embodiments, the inventive pharmaceutical compositions are useful for treating and/or preventing a disease associated with protein aggregation in a subject in need thereof. In certain embodiments, the inventive pharmaceutical compositions are useful for reducing and/or preventing protein aggregation in a subject in need thereof. In certain embodiments, the inventive pharmaceutical compositions are useful for modulating E3 ubiquitin ligase in a subject in need thereof. In certain embodiments, the inventive pharmaceutical compositions are useful in treating and/or preventing a neurodegenerative disease (e.g., PD, AD) in a subject. In certain embodiments, the inventive pharmaceutical compositions are useful in treating and/or preventing diseases associated with Tar DNA binding protein 43 kDa (TDP-43) (e.g., amyotrophic lateral sclerosis (ALS) and frontotemporal dementia).

Another aspect of the present invention relates to methods of treating and/or preventing a disease associated with protein aggregation or a neurodegenerative disease in a subject in need thereof. The diseases associated with protein aggregation and may be treated and/or prevented by the inventive methods and compositions include, but are not limited to, an amyloidosis (e.g., Parkinson's disease or Alzheimer's disease) or a prion disease.

In another aspect, the present invention provides methods of treating and/or preventing diseases associated with Tar DNA binding protein 43 kDa (TDP-43) (e.g., amyotrophic lateral sclerosis (ALS) and frontotemporal dementia).

In another aspect, the present invention provides methods of reducing and/or preventing protein aggregation in a subject in need thereof.

In yet another aspect, the present invention provides methods of modulating E3 ubiquitin ligase in a subject in need thereof.

The methods of the present invention include administering to the subject an effective amount of a compound described herein, or a pharmaceutical composition thereof. In certain embodiments, the effective amount is a therapeutically effective amount. In certain embodiments, the effective amount is a prophylactically effective amount.

Another aspect of the invention relates to methods of screening a library of compounds to identify one or more compounds that are useful for the methods of the invention. In certain embodiments, the compound identified by the methods of screening is useful for treating and/or preventing a disease associated with protein aggregation, for treating and/or preventing a neurodegenerative disease, for treating and/or preventing diseases associated with TDP-43, for reducing and/or preventing protein aggregation, and/or for modulating E3 ubiquitin ligase in a subject in need thereof.

In yet another aspect, the present invention provides the compounds described herein, and pharmaceutical compositions thereof, for use in the treatment and/or prevention of a disease associated with protein aggregation, in the treatment and/or prevention of a neurodegenerative disease, in the treatment and/or prevention of a disease associated with TDP-43, in the reduction and/or prevention of protein aggregation, and/or in the modulation of E3 ubiquitin ligase in a subject in need thereof.

Another aspect of the present invention relates to kits comprising a container with a compound described herein, or a pharmaceutical composition thereof. The kits of the invention may include a single dose or multiple doses of the compound or pharmaceutical composition. The provided kits may be useful for treating and/or preventing a disease associated with protein aggregation, for treating and/or preventing a neurodegenerative disease, for treating and/or preventing a disease associated with TDP-43, for reducing and/or preventing protein aggregation, and/or for modulating E3 ubiquitin ligase in a subject in need thereof. In certain embodiments, the kits further include instructions for administering the compound or pharmaceutical composition to the subject.

The details of particular embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-4}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

"Alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

"Haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-4}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix—ene, e.g., alkylene, alkenylene, alkynylene, carbocyclylene, heterocyclylene, arylene, and heteroarylene.

As used herein, the term "optionally substituted" refers to substituted or unsubstituted.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N $(C_{1-6}$ alkyl)$_2$, $-OC(=O)NH(C_{1-6}$ alkyl), $-NHC(=O)$ $(C_{1-6}$ alkyl), $-N(C_{1-6}$ alkyl)$C(=O)(C_{1-6}$ alkyl), $-NHCO_2$ $(C_{1-6}$ alkyl), $-NHC(=O)N(C_{1-6}$ alkyl)$_2$, $-NHC(=O)NH$ $(C_{1-6}$ alkyl), $-NHC(=O)NH_2$, $-C(=NH)O(C_{1-6}$ alkyl), $-OC(=NH)(C_{1-6}$ alkyl), $-OC(=NH)OC_{1-6}$ alkyl, $-C(=NH)N(C_{1-6}$ alkyl)$_2$, $-C(=NH)NH(C_{1-6}$ alkyl), $-C(=NH)NH_2$, $-OC(=NH)N(C_{1-6}$ alkyl)$_2$, $-OC(NH)NH(C_{1-6}$ alkyl), $-OC(NH)NH_2$, $-NHC(NH)N(C_{1-6}$ alkyl)$_2$, $-NHC(=NH)NH_2$, $-NHSO_2(C_{1-6}$ alkyl), $-SO_2N(C_{1-6}$ alkyl)$_2$, $-SO_2NH(C_{1-6}$ alkyl), $-SO_2NH_2$, $-SO_2C_{1-6}$ alkyl, $-SO_2OC_{1-6}$ alkyl, $-OSO_2C_{1-6}$ alkyl, $-SOC_{1-6}$ alkyl, $-Si(C_{1-6}$ alkyl)$_3$, $-OSi(C_{1-6}$ alkyl)$_3$ $-C(=S)N(C_{1-6}$ alkyl)$_2$, $C(=S)NH(C_{1-6}$ alkyl), $C(=S)$ $NH_2$, $-C(=O)S(C_{1-6}$ alkyl), $-C(=S)SC_{1-6}$ alkyl, $-SC(=S)SC_{1-6}$ alkyl, $-P(=O)_2(C_{1-6}$ alkyl), $-P(=O)(C_{1-6}$ alkyl)$_2$, $-OP(=O)(C_{1-6}$ alkyl)$_2$, $-OP(=O)(OC_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of $-C(=O)R^{aa}$, $-CHO$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-C(=O)NR^{bb}SO_2R^{aa}$, $-C(=S)N(R^{bb})_2$, $-C(=O)SR^{aa}$, or $-C(=S)SR^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{bb})R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)$ $(R^{aa})_2$, $-P(=O)_2N(R^{cc})_2$, $-P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, R, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR, $-N(R^{cc})_2$, $-C(=O)R^{aa}$, $-C(=O)N(R^{cc})_2$, $-CO_2R^{aa}$, $-SO_2R^{aa}$, $-C(=NR^{cc})R^{aa}$, $-C(=NR^{cc})OR^{aa}$, $-C(=NR^{cc})N$ $(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., $-C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., $-C(=O)OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)] methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl) methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

These and other exemplary substituents are described in more detail in the Detailed Description, Figures, Examples, and Claims. The invention is not intended to be limited in any manner by the above exemplary listing of substituents.

OTHER DEFINITIONS

The following definitions are more general terms used throughout the present application.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound and wherein x is a number greater than 0. A given compound may form more than one type of hydrates, including, e.g., monohydrates (is 1), lower hydrates (is a number greater than 0 and smaller than 1, e.g., hemihydrates (R.0.5$H_2O$)), and polyhydrates (is a number greater than 1, e.g., dihydrates (R.2$H_2O$) and hexahydrates (R.6$H_2O$)).

The term "tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds described herein, which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish.

The terms "administer," "administering," or "administration," as used herein, refers to implanting, absorbing, ingesting, injecting, inhaling, or otherwise introducing an inventive compound, or a pharmaceutical composition thereof, in or on a subject.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein, such as a disease associated with protein aggregation (e.g., Parkinson's disease). In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of exposure to a pathogen). Treatment may also be continued after symptoms have resolved, for example, to delay or prevent recurrence.

As used herein, the terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "protein" or "peptide" comprises a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The present application refers to various issued patent, published patent applications, journal articles, and other publications, all of which are incorporated herein by reference.

The details of one or more embodiments of the invention are set forth herein. Other features, objects, and advantages of the invention will be apparent from the Detailed Description, the Figures, the Examples, and the Claims.

BRIEF DESCRIPTION OF THE DRAWINGS

FIG. 5 shows that ABI rescues A53T α-syn toxicity ventral mesencephalic cultures. (A) Three representative fields (20× magnification) of control, A53T, and A53T+0.1 μM ABI. Green or dark grey; TH-positive neurons. Red or light grey; MAP2 neuronal marker. Yellow or white; merge. Arrows indicate TH-positive neurons. A53T α-syn decreases the % of TH-positive neurons and this is reversed by ABI. (B) Cumulative frequency plot of neurite length in control and A53T α-syn transduced neurons with or without 0.1 μM ABI. The shift of the frequency to shorter neurites by A53T α-syn is reversed by 0.1 μM ABI.

FIG. 6 shows that ABI efficacy against α-syn toxicity correlates with growth inhibition of WT cells. (A) Dose-response curves of ABI1-3 (μM) in WT cells. Y-axis is growth relative to untreated cells. (B) Dose-response curves of ABI1-3 (μM) in α-syn-expressing yeast. Y-axis is % of maximum rescue by ABI1. Growth and analysis was as described in the methods. Data from these curves were used to generate FIG. 3B showing that growth inhibition correlated with efficacy against α-syn toxicity.

FIG. 7 shows that chemical genetics reveals ABI network that alleviates growth inhibition in WT cells. (A) Dose-response curves for ABI2 (μM) in cells with either a vector control or a construct with hits from the overexpression screen. Y-axis is growth relative to untreated cells. (B) Dose-response curves for ABI2 in WT cells overexpressing several amino acid permeases (and biosynthetic enzyme, LEU2) show the specificity of the rescue. Only TAT1, which is a tryptophan and branched chain amino acid permease, also reverses ABI2 growth inhibition. X- and Y-axes are same as in (A). (C) Dose-response curves of ABI2 in WT cells overexpressing several UBPs. Rescue of ABI2 growth inhibition is highly specific to UBP7 and UBP11. X- and Y-axes are same as in (A). (D) Dose-response curves for ABI2 in strains mutated for genes identified in the Tn7 and spontaneous mutant screens. All strains are full genomic deletions, except for the Δp.rsp5 and rsp5$_{G747E}$ strains. X- and Y-axes are same as in (A). (E) Dose-response curves of ABI2 in original spontaneous ABI2-resistant mutants. X- and Y-axes are same as in (A). The single amino acid substitution is noted in the legend. 'stop' indicates that the point mutant created a premature stop codon that likely functions as a full deletion. (F). Western blot of WT and Δp.rsp5 show that inserting the HygMX cassette ~500 bp upstream of the promoter significantly reduced Rsp5p protein levels. A polyclonal antibody against Rsp5 was used to detect endogenous protein. Pgk1 serves as a loading control. (G) Western blot of Rsp5 in WT and rsp5$_{G747E}$ cells. There is only a mild decrease in protein levels between WT and mutant strains, indicating that the effects of this mutant are by reducing activity, not be reducing Rsp5 levels. Note, that the rsp5$_{G747E}$ mutation actually makes the protein run slightly slower than WT Rsp5p. (H) Western blot analysis of Rsp5 in WT (RSP5/RSP5) or heterozygous deletion (RSP5/Δrsp5) diploid yeast strains. Since RSP5 is essential, a full deletion was only tested in diploid strains. There was an approximate 2-fold decrease in protein in this strain.

FIG. 9 shows that ABI promotes Bap2 degradation in an Rsp5-dependent manner. (A) Dose-response curves of ABI2 (μM) in strains deleted for, or overexpressing BAP2. Y-axis is growth relative to untreated cells. (B) Dose-response curves of leucine concentration (μg/mL) for RSP5 or rsp5$_{G747E}$ yeast strains. Y-axis is growth relative to cells at normal leucine concentration (100 μg/mL). (C) ABI dose-response curves of WT yeast with 100 μg/mL or 40 μg/mL leucine. 100 μg/mL is the standard leucine concentration in complete synthetic media. 40 μg/mL is a leucine concentration that does not reduce the growth rate of WT cells (see arrow in panel (B). (D) Western blot analysis of proteinA-tagged Bap2 expressed form a GAL1-regulated construct. Bap2 was expressed for 2 hours with galactose and then compound added for 1.5 hrs. Quantitation represents Bap2-ProteinA (densitometry) normalized to total protein (from coomassie stained gel). (E) Altering leucine levels does not account for rescue of α-syn toxicity. Leucine (μg/mL) was both increased and decreased with no shift in ABI2 dose-response other than increasing the sensitivity to low leucine levels. (F) Deleting Δbap2 enhances ABI growth inhibition, but did not rescue α-syn toxicity. Together, (E) and (F) indicate that the leucine metabolism connection to ABI is not part of its efficacy against α-syn toxicity, yet is a consequence of Rsp5 over-activation.

FIG. 10 shows that genetic modifiers of ABI2 affect its ability to rescue α-syn toxicity. (A) Dose-response curves of ABI2 (μM) in α-syn with deletions of chemical genetic modifiers. Y-axis is % max response relative to ABI2 in the WT α-syn strain. The right Y-axis is for Δdoa4, which rescued α-syn toxicity on its own, thus requiring an extended scale. (B) Dose-response curves of ABI2 with overexpression suppressors. "p" in legend indicates gene is expressed from a plasmid. Axes are same as in (A), with the exception that the right Y-axis is for BAP2, which partially rescued α-syn toxicity on its own.

DETAILED DESCRIPTION OF CERTAIN EMBODIMENTS OF THE INVENTION

Figure 1C:
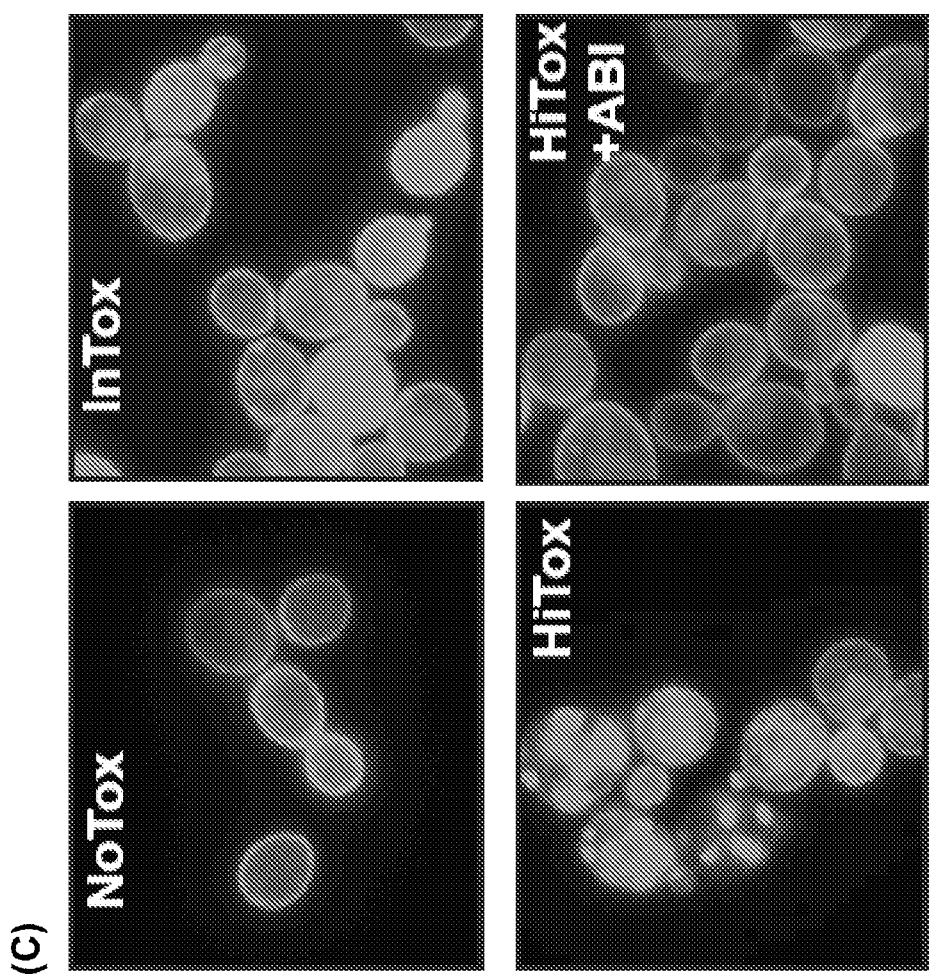
FIG. 1 shows that ABI protects yeast against α-syn toxicity. (A) Structure of lead compound ABI. (B) Dose-response curves showing the relative rescue of ABI ($\log_2$, μM) in five yeast proteinopathy models. Rescue is relative to a positive control compound as determined by growth ($OD_{600}$). (C) Localization of α-syn-GFP in strains with increasing toxicity: NoTox, InTox, HiTox and HiTox treated with 10 μM ABI. (D) ABI (10 μM) reduced the % of ROS-positive cells in the HiTox strain. (E) (Left panel) Western blot of α-syn-GFP in NoTox, InTox, and HiTox strains with anti-α-syn antibody. (Right panel) Quantitation of western blot (α-syn relative to total protein quantitated from a Coomassie gel and normalized to 100% for HiTo). : $P<0.01$; and *: $P<0.001$, according to one-way ANOVA and a Tukey's test.

The present invention provides benzimidazole derivatives and uses thereof. In one aspect, the invention provides compounds of Formula (I), and pharmaceutically acceptable salts, solvates, hydrates, polymorphs, co-crystals, tautomers, stereoisomers, isotopically labeled derivatives, prodrugs, and pharmaceutical compositions thereof. These compounds have been found to modulate E3 ubiquitin ligase and thus may be useful for the treatment and/or prevention of diseases associated with protein aggregation (e.g., amyloidoses (e.g., Parkinson's disease, Alzheimer's disease, and prion diseases)) and for the reduction and/or prevention of protein aggregation in a subject in need thereof. These compounds may also be used as biological probes to uncover new nodes in complex disease networks and study biological processes.

Compounds

In one aspect of the present invention, the present invention provides compounds of Formula (I):

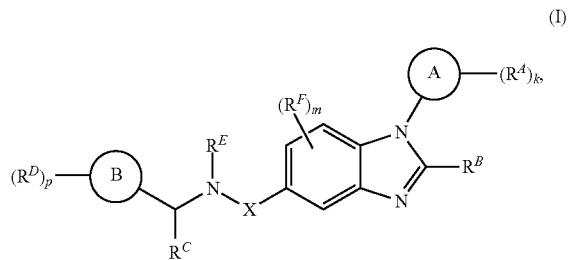

(I)

and pharmaceutically acceptable salts, solvates, hydrates, polymorphs, co-crystals, tautomers, stereoisomers, isotopically labeled derivatives, and prodrugs thereof;
wherein:
Ring A is substituted or unsubstituted aryl or substituted or unsubstituted heteroaryl;
Ring B is substituted or unsubstituted aryl or substituted or unsubstituted heteroaryl;
X is —C(=O)—, —C(=S)—, —C(=NR$^G$)—, —S(=O)—, or —S(=O)$_2$—;

each instance of R$^A$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A1}$, —N(R$^{A1}$)$_2$, —SR$^{A1}$, —CN, —SCN, —C(=NR$^{A1}$)R$^{A1}$, —C(=NR$^{A1}$)OR$^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, —OC(=O)N(R$^{A1}$)$_2$, or a nitrogen protecting group when attached to a nitrogen atom, or two R$^A$ groups are joined to form a substituted or unsubstituted carbocyclic, substituted or unsubstituted heterocyclic, substituted or unsubstituted aryl, or substituted or unsubstituted heteroaryl ring;

each instance of R$^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A1}$ groups are joined to form a substituted or unsubstituted heterocyclic ring;

R$^B$ is hydrogen, halogen, or substituted or unsubstituted C$_{1-6}$ alkyl;

R$^C$ is hydrogen, halogen, or substituted or unsubstituted C$_{1-6}$ alkyl;

each instance of R$^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D1}$, —N(R$^{D1}$)$_2$, —SR$^{D1}$, —CN, —SCN, —C(=NR$^{D1}$)R$^{D1}$, —C(=NR$^{D1}$)OR$^{D1}$, —C(=NR$^{D1}$)N(R$^{D1}$)$_2$, —C(=O)R$^{D1}$, —C(=O)OR$^{D1}$, —C(=O)N(R$^{D1}$)$_2$, —NO$_2$, —NR$^{D1}$C(=O)R$^{D1}$, —NR$^{D1}$C(=O)OR$^{D1}$, —NR$^{D1}$C(=O)N(R$^{D1}$)$_2$, —OC(=O)R$^{D1}$, —OC(=O)OR$^{D1}$, —OC(=O)N(R$^{D1}$)$_2$, or a nitrogen protecting group when attached to a nitrogen atom, or two R$^D$ groups are joined to form a substituted or unsubstituted carbocyclic, substituted or unsubstituted heterocyclic, substituted or unsubstituted aryl, or substituted or unsubstituted heteroaryl ring;

each instance of R$^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{D1}$ groups are joined to form a substituted or unsubstituted heterocyclic ring;

R$^E$ is hydrogen, substituted or unsubstituted C$_{1-6}$ alkyl, or a nitrogen protecting group;

each instance of R$^F$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{F1}$, —N(R$^{F1}$)$_2$, —SR$^{F1}$, —CN, —SCN, —C(=NR$^{F1}$)R$^{F1}$, —C(=NR$^{F1}$)OR$^{F1}$, —C(=NR$^{F1}$)N(R$^F$)$_2$, —C(=O)R$^{F1}$, —C(=O)OR$^{F1}$, —C(=O)N(R$^{F1}$)$_2$, —NO$_2$, —NR$^{F1}$C(=O)R$^{F1}$, —NR$^{F1}$C(=O)OR$^{F1}$, —NR$^{F1}$C(=O)N(R$^{F1}$)$_2$, —OC(=O)R$^{F1}$, —OC(=O)OR$^{F1}$, —OC(=O)N(R$^{F1}$)$_2$, or a nitrogen protecting group when attached to a nitrogen atom, or two R$^F$ groups are joined to form a substituted or unsubstituted carbocyclic, substituted or unsubstituted heterocyclic, substituted or unsubstituted aryl, or substituted or unsubstituted heteroaryl ring;

each instance of R$^{F1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{F1}$ groups are joined to form a substituted or unsubstituted heterocyclic ring;

R$^G$ is hydrogen, substituted or unsubstituted C$_{1-6}$ alkyl, or a nitrogen protecting group;

k is 0, 1, 2, 3, 4, or 5;

p is 0, 1, 2, 3, 4, or 5; and m is 0, 1, 2, or 3.

In certain embodiments, the present invention provides compounds of Formula (I), and pharmaceutically acceptable salts thereof.

Compounds of Formula (I) include substituted or unsubstituted aryl or substituted or unsubstituted heteroaryl as Ring A. In certain embodiments, Ring A is substituted aryl. In certain embodiments, Ring A is unsubstituted aryl. In certain embodiments, Ring A is substituted or unsubstituted, 6- to 14-membered aryl. In certain embodiments, Ring A is monocyclic aryl. In certain embodiments, Ring A is substituted phenyl. In certain embodiments, Ring A is of the formula:

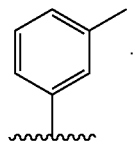

In certain embodiments, Ring A is of the formula:

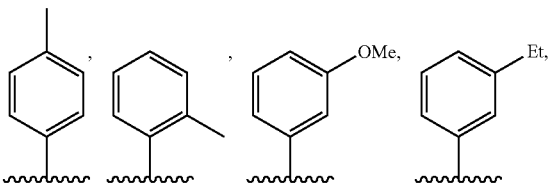

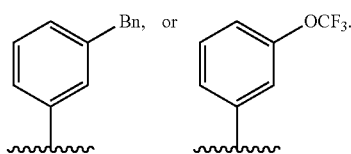

In certain embodiments, Ring A is of the formula:

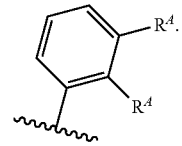

In certain embodiments, Ring A is of the formula:

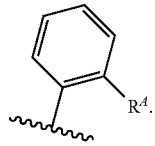

In certain embodiments, Ring A is of the formula:

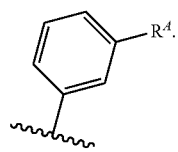

In certain embodiments, Ring A is of the formula:

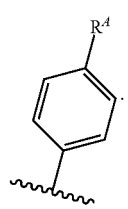

In certain embodiments, Ring A is of the formula:

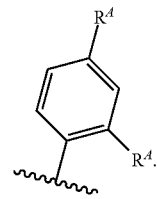

In certain embodiments, Ring A is of the formula:

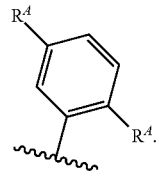

In certain embodiments, Ring A is of the formula:

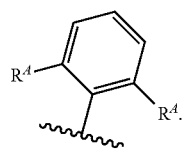

In certain embodiments, Ring A is of the formula:

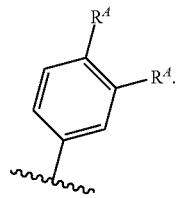

In certain embodiments, Ring A is of the formula:

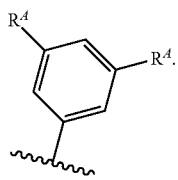

In certain embodiments, Ring A is of the formula:

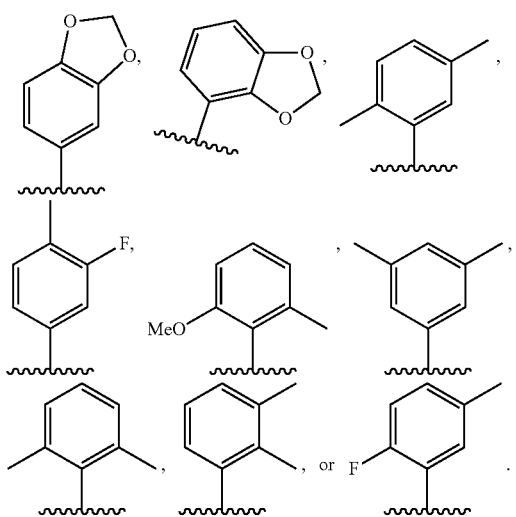

In certain embodiments, Ring A is unsubstituted phenyl. In certain embodiments, Ring A is substituted or unsubstituted, bicyclic aryl. In certain embodiments, Ring A is substituted naphthyl. In certain embodiments, Ring A is unsubstituted naphthyl. In certain embodiments, Ring A is tricyclic aryl. In certain embodiments, Ring A is substituted anthracenyl. In certain embodiments, Ring A is unsubstituted anthracenyl. In certain embodiments, Ring A is optionally substituted aryl fused with one or more optionally substituted carbocyclic, optionally substituted heterocyclic, optionally substituted aryl, or optionally substituted heteroaryl groups wherein the point of attachment is on the aryl.

Ring A of Formula (I) may also be an optionally substituted heteroaryl. In certain embodiments, Ring A is substituted heteroaryl. In certain embodiments, Ring A is unsubstituted heteroaryl. In certain embodiments, Ring A is monocyclic heteroaryl. In certain embodiments, Ring A is substituted or unsubstituted, 5- or 6-membered, monocyclic heteroaryl, wherein 1, 2, or 3 atoms in the ring of the heteroaryl is independently selected from the group consisting of nitrogen, oxygen, and sulfur. In certain embodiments, Ring A is substituted or unsubstituted, 6-membered monocyclic heteroaryl. In certain embodiments, Ring A is substituted or unsubstituted, 6-membered monocyclic heteroaryl, wherein only one of the six atoms in the ring of the heteroaryl is nitrogen. In certain embodiments, Ring A is of the formula:

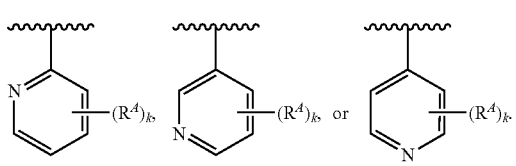

In certain embodiments, Ring A is substituted or unsubstituted, 6-membered monocyclic heteroaryl, wherein only two of the six atoms in the ring of the heteroaryl are nitrogen. In certain embodiments, Ring A is of the formula:

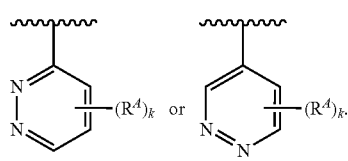

In certain embodiments, Ring A is of the formula:

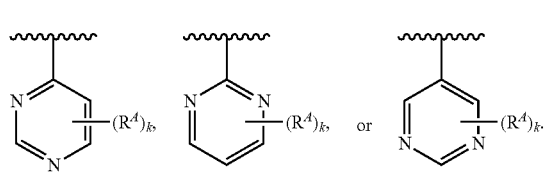

In certain embodiments, Ring A is of the formula:

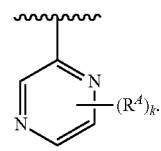

In certain embodiments, Ring A is substituted or unsubstituted, 6-membered monocyclic heteroaryl, wherein only three of the six atoms in the ring of the heteroaryl are nitrogen. In certain embodiments, Ring A is of the formula:

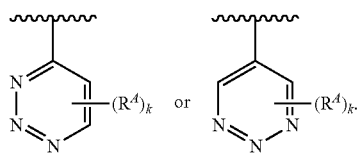

In certain embodiments, Ring A is of the formula:

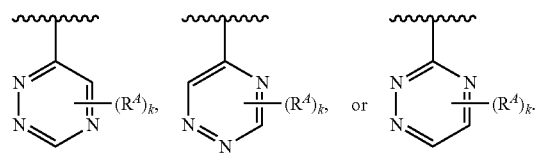

In certain embodiments, Ring A is of the formula:

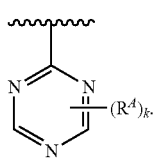

In certain embodiments, Ring A is substituted or unsubstituted, 5-membered monocyclic heteroaryl. In certain embodiments, Ring A is substituted or unsubstituted, 5-membered monocyclic heteroaryl, wherein only one of the five atoms in the ring of the heteroaryl is nitrogen, oxygen, or sulfur. In certain embodiments, Ring A is of the formula:

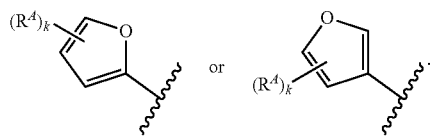

In certain embodiments, Ring A is of the formula:

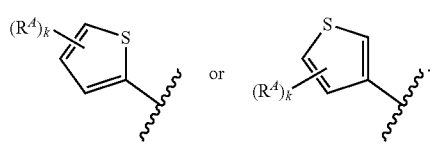

In certain embodiments, Ring A is of the formula:

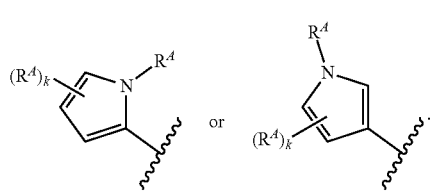

In certain embodiments, Ring A is substituted or unsubstituted, 5-membered monocyclic heteroaryl, wherein only two of the five atoms in the ring of the heteroaryl are independently nitrogen, oxygen, or sulfur. In certain embodiments, Ring A is of the formula:

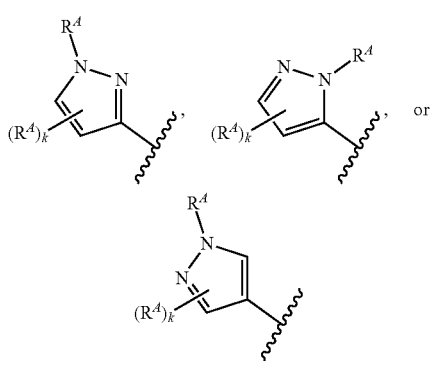

In certain embodiments, Ring A is of the formula:

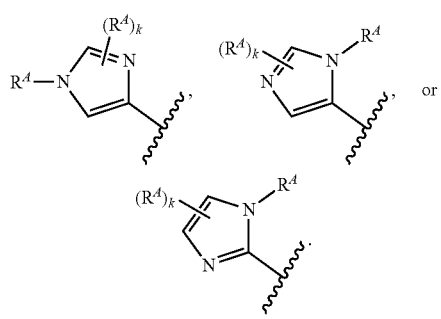

In certain embodiments, Ring A is of the formula:

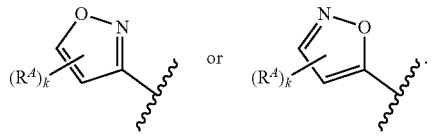

In certain embodiments, Ring A is of the formula:

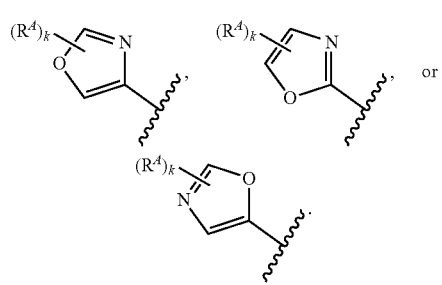

In certain embodiments, Ring A is of the formula:

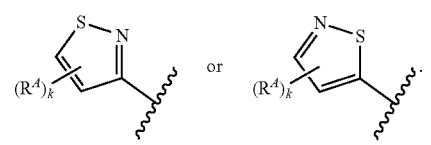

In certain embodiments, Ring A is of the formula:

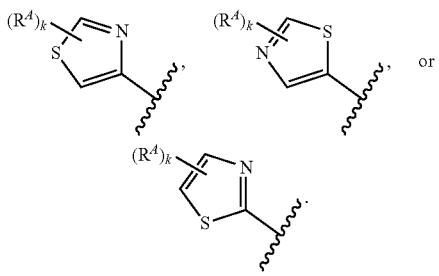

In certain embodiments, Ring A is substituted or unsubstituted, 5-membered monocyclic heteroaryl, wherein only three of the five atoms in the ring of the heteroaryl are independently nitrogen, oxygen, or sulfur. In certain embodiments, Ring A is of the formula:

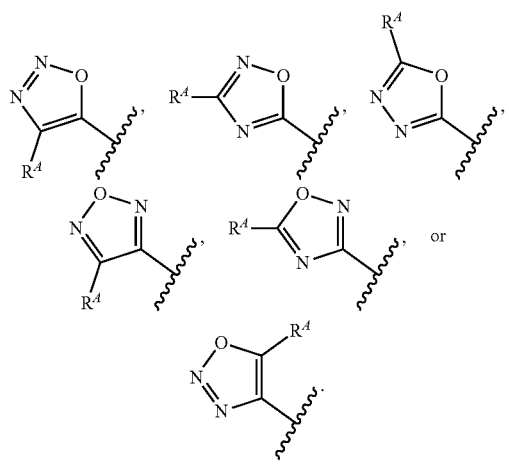

In certain embodiments, Ring A is of the formula

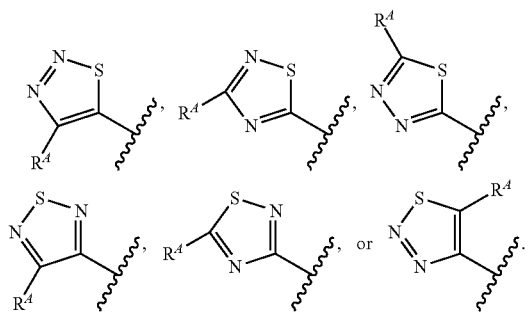

In certain embodiments, Ring A is of the formula:

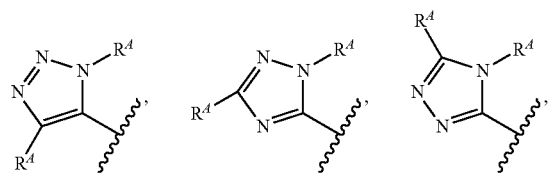

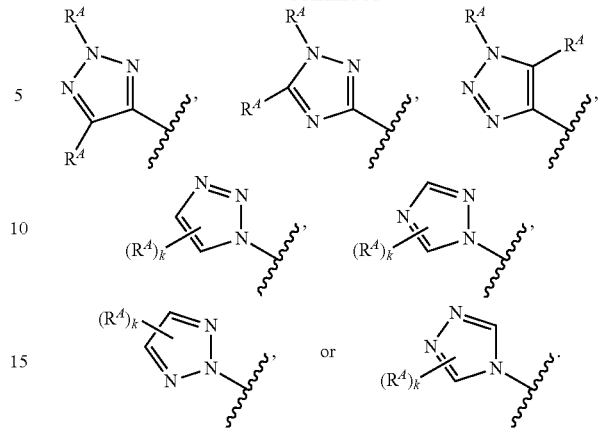

In certain embodiments, Ring A is substituted or unsubstituted, 5-membered monocyclic heteroaryl, wherein only four of the five atoms in the ring of the heteroaryl are nitrogen, oxygen, or sulfur. In certain embodiments, Ring A is of the formula:

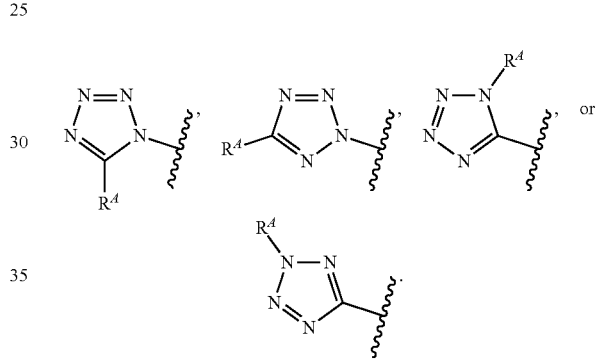

In certain embodiments, Ring A is bicyclic heteroaryl, wherein the point of attachment may be on any atom of the bicyclic heteroaryl ring system, as valency permits. In certain embodiments, Ring A is a monocyclic heteroaryl ring fused with phenyl. In certain embodiments, Ring A is a 5-membered monocyclic heteroaryl ring fused with phenyl. In certain embodiments, Ring A is a 6-membered monocyclic heteroaryl ring fused with phenyl. In certain embodiments, Ring A is a monocyclic heteroaryl ring fused with another monocyclic heteroaryl. In certain embodiments, Ring A is a 5-membered monocyclic heteroaryl ring fused with another 5-membered monocyclic heteroaryl. In certain embodiments, Ring A is a 5-membered monocyclic heteroaryl ring fused with a 6-membered monocyclic heteroaryl. In certain embodiments, Ring A is a 6-membered monocyclic heteroaryl ring fused with another 6-membered monocyclic heteroaryl. The bicyclic heteroaryl described herein may be substituted or unsubstituted. In certain embodiments, Ring A is substituted or unsubstituted, 9- or 10-membered, bicyclic heteroaryl, wherein 1, 2, 3, or 4 atoms in the ring of the heteroaryl is independently selected from the group consisting of nitrogen, oxygen, and sulfur. In certain embodiments, Ring A is substituted or unsubstituted, 9-membered, bicyclic heteroaryl, wherein only one atom in the ring of the heteroaryl is nitrogen, oxygen, or sulfur. In certain embodiments, Ring A is substituted or unsubstituted, 9-membered, bicyclic heteroaryl, wherein only one atom in the ring of the heteroaryl is nitrogen. In certain embodiments, Ring A is of the formula:

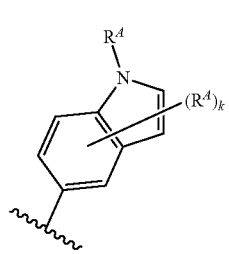

In certain embodiments, Ring A is of the formula:

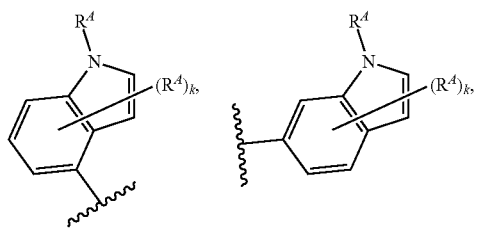

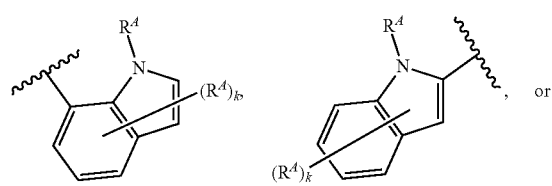, or

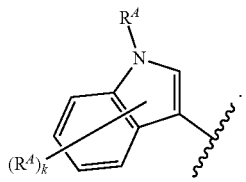

Compounds of Formula (I) include substituted or unsubstituted aryl or substituted or unsubstituted heteroaryl as Ring B. In certain embodiments, Ring B is substituted aryl. In certain embodiments, Ring B is unsubstituted aryl. In certain embodiments, Ring B is substituted or unsubstituted, 6- to 14-membered aryl. In certain embodiments, Ring B is monocyclic aryl. In certain embodiments, Ring B is substituted phenyl. In certain embodiments, Ring B is of the formula:

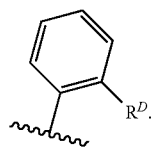

In certain embodiments, Ring B is of the formula:

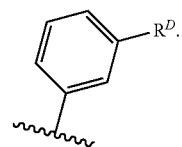

In certain embodiments, Ring B is of the formula:

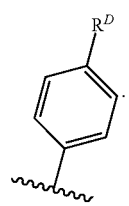

In certain embodiments, Ring B is of the formula:

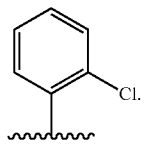

In certain embodiments, Ring B is of the formula:

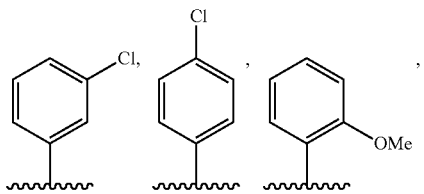

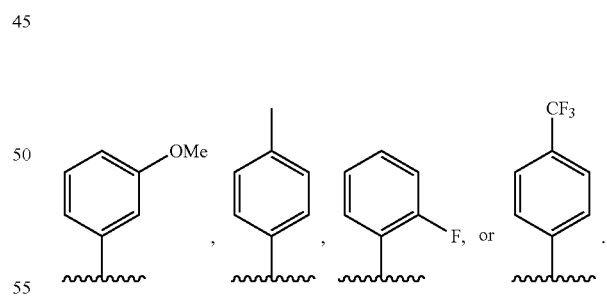

In certain embodiments, Ring B is of the formula:

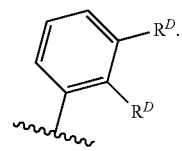

In certain embodiments, Ring B is of the formula:

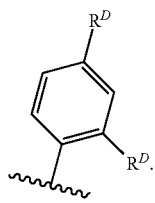

In certain embodiments, Ring B is of the formula:

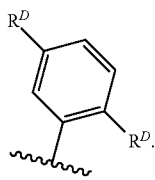

In certain embodiments, Ring B is of the formula:

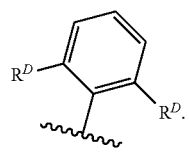

In certain embodiments, Ring B is of the formula:

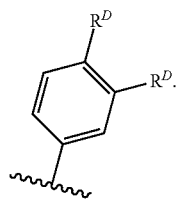

In certain embodiments, Ring B is of the formula:

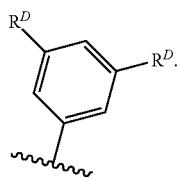

In certain embodiments, Ring B is of the formula:

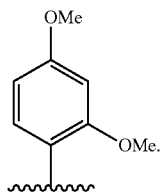 [SMILES: *c1ccc(OC)cc1OC]

In certain embodiments, Ring B is unsubstituted phenyl. In certain embodiments, Ring B is substituted or unsubstituted, bicyclic aryl. In certain embodiments, Ring B is substituted naphthyl. In certain embodiments, Ring B is unsubstituted naphthyl. In certain embodiments, Ring B is tricyclic aryl. In certain embodiments, Ring B is substituted anthracenyl. In certain embodiments, Ring B is unsubstituted anthracenyl. In certain embodiments, Ring B is optionally substituted aryl fused with one or more optionally substituted carbocyclic, optionally substituted heterocyclic, optionally substituted aryl, or optionally substituted heteroaryl groups wherein the point of attachment is on the aryl.

Ring B of Formula (I) may also be an optionally substituted heteroaryl. In certain embodiments, Ring B is substituted heteroaryl. In certain embodiments, Ring B is unsubstituted heteroaryl. In certain embodiments, Ring B is monocyclic heteroaryl. In certain embodiments, Ring B is substituted or unsubstituted, 5- or 6-membered, monocyclic heteroaryl, wherein 1, 2, or 3 atoms in the ring of the heteroaryl is independently selected from the group consisting of nitrogen, oxygen, and sulfur. In certain embodiments, Ring B is substituted or unsubstituted, 6-membered monocyclic heteroaryl. In certain embodiments, Ring B is substituted or unsubstituted, 6-membered monocyclic heteroaryl, wherein only one of the six atoms in the ring of the heteroaryl is nitrogen. In certain embodiments, Ring B is of the formula:

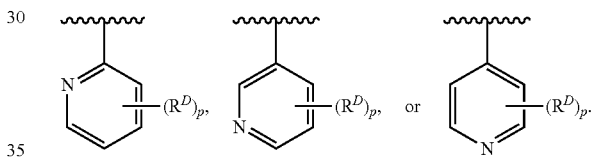

In certain embodiments, Ring B is substituted or unsubstituted, 6-membered monocyclic heteroaryl, wherein only two of the six atoms in the ring of the heteroaryl are nitrogen. In certain embodiments, Ring B is of the formula:

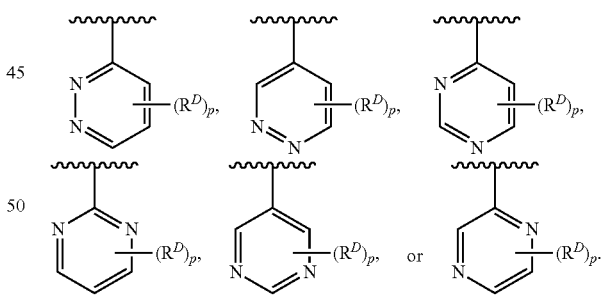

In certain embodiments, Ring B is substituted or unsubstituted, 6-membered monocyclic heteroaryl, wherein only three of the six atoms in the ring of the heteroaryl are nitrogen. In certain embodiments, Ring B is of the formula:

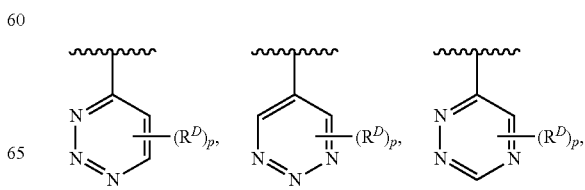

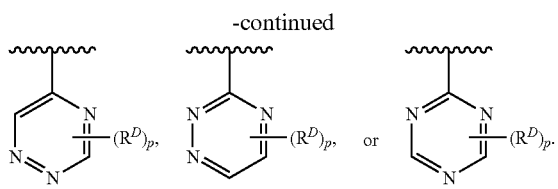

In certain embodiments, Ring B is substituted or unsubstituted, 5-membered monocyclic heteroaryl. In certain embodiments, Ring B is substituted or unsubstituted, 5-membered monocyclic heteroaryl, wherein only one of the five atoms in the ring of the heteroaryl is nitrogen, oxygen, or sulfur. In certain embodiments, Ring B is of the formula:

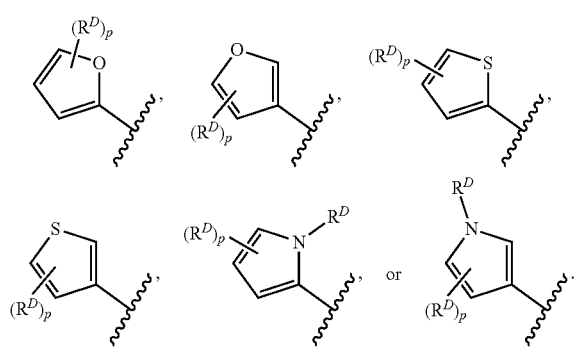

In certain embodiments, Ring B is substituted or unsubstituted, 5-membered monocyclic heteroaryl, wherein only two of the five atoms in the ring of the heteroaryl are independently nitrogen, oxygen, or sulfur. In certain embodiments, Ring B is of the formula:

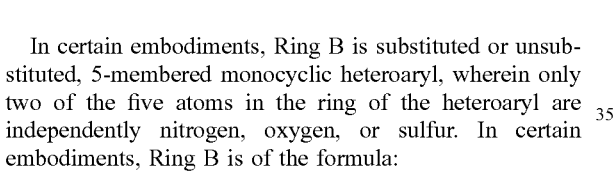

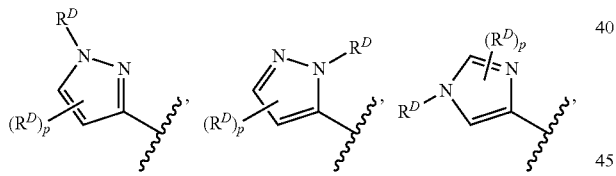

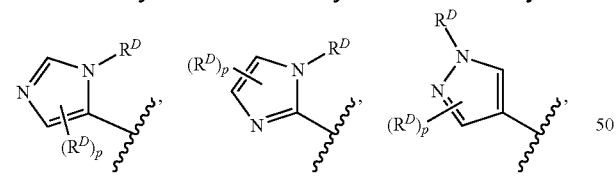

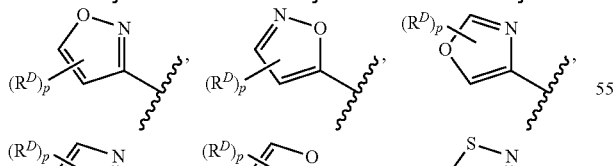

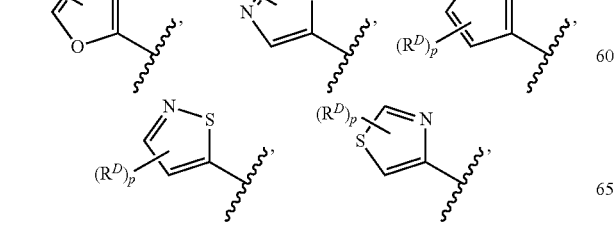

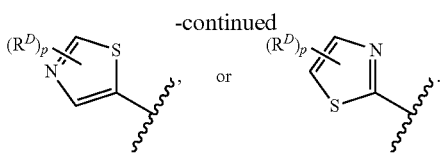

In certain embodiments, Ring B is substituted or unsubstituted, 5-membered monocyclic heteroaryl, wherein only three of the five atoms in the ring of the heteroaryl are independently nitrogen, oxygen, or sulfur. In certain embodiments, Ring B is of the formula:

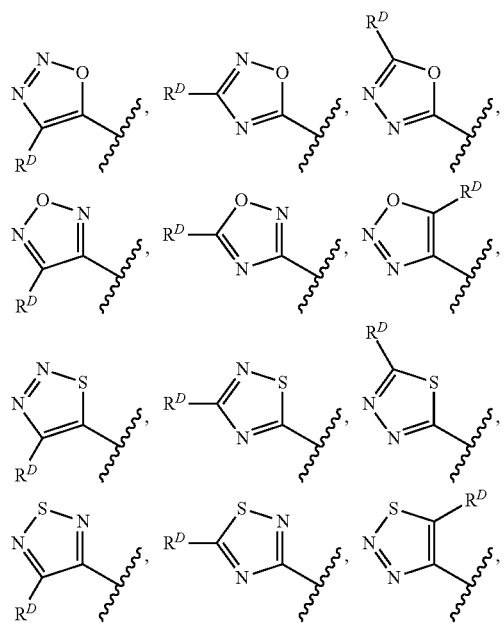

In certain embodiments, Ring B is substituted or unsubstituted, 5-membered monocyclic heteroaryl, wherein only four of the five atoms in the ring of the heteroaryl are nitrogen, oxygen, or sulfur. In certain embodiments, Ring B is of the formula:

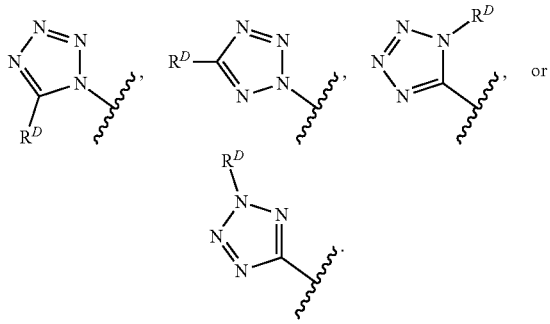

In certain embodiments, Ring B is bicyclic heteroaryl, wherein the point of attachment may be on any atom of the bicyclic heteroaryl ring system, as valency permits. In certain embodiments, Ring B is a monocyclic heteroaryl ring fused with phenyl. In certain embodiments, Ring B is a 5-membered monocyclic heteroaryl ring fused with phenyl. In certain embodiments, Ring B is a 6-membered monocyclic heteroaryl ring fused with phenyl. In certain embodiments, Ring B is a monocyclic heteroaryl ring fused with another monocyclic heteroaryl. In certain embodiments, Ring B is a 5-membered monocyclic heteroaryl ring fused with another 5-membered monocyclic heteroaryl. In certain embodiments, Ring B is a 5-membered monocyclic heteroaryl ring fused with a 6-membered monocyclic heteroaryl. In certain embodiments, Ring B is a 6-membered monocyclic heteroaryl ring fused with another 6-membered monocyclic heteroaryl. The bicyclic heteroaryl described herein may be substituted or unsubstituted. In certain embodiments, Ring B is substituted or unsubstituted, 9- or 10-membered, bicyclic heteroaryl, wherein 1, 2, 3, or 4 atoms in the ring of the heteroaryl is independently selected from the group consisting of nitrogen, oxygen, and sulfur. In certain embodiments, Ring B is substituted or unsubstituted, 9-membered, bicyclic heteroaryl, wherein only one atom in the ring of the heteroaryl is nitrogen, oxygen, or sulfur.

Compounds of Formula (I) includes a divalent linker moiety X. In certain embodiments, X is —C(=O)—. In certain embodiments, X is —C(=S)—. In certain embodiments, X is —C(=NR$^G$)—. In certain embodiments, X is —C(=NH)—. In certain embodiments, X is —S(=O)—. In certain embodiments, X is —S(=O)$_2$—.

Ring A of compounds of Formula (I) may include one or more substituents R$^A$. In certain embodiments, at least one R$^A$ is H. In certain embodiments, at least one R$^A$ is halogen. In certain embodiments, at least one R$^A$ is F. In certain embodiments, at least one R$^A$ is Cl. In certain embodiments, at least one R$^A$ is Br. In certain embodiments, at least one R. In certain embodiments, at least one R is I (iodine). In certain embodiments, at least one R$^A$ is substituted acyl. In certain embodiments, at least one R$^A$ is unsubstituted acyl. In certain embodiments, at least one R$^A$ is substituted alkyl. In certain embodiments, at least one R$^A$ is unsubstituted alkyl. In certain embodiments, at least one R$^A$ is C$_{1-6}$ alkyl. In certain embodiments, at least one R$^A$ is methyl. In certain embodiments, at least one R$^A$ is unsubstituted methyl. In certain embodiments, at least one R$^A$ is —CH$_2$F. In certain embodiments, at least one R$^A$ is —CHF$_2$. In certain embodiments, at least one R$^A$ is —CF$_3$. In certain embodiments, at least one R$^A$ is Bn. In certain embodiments, at least one R$^A$ is ethyl. In certain embodiments, at least one R$^A$ is substituted ethyl. In certain embodiments, at least one R$^A$ is —(CH$_2$)$_2$Ph. In certain embodiments, at least one R$^A$ is propyl. In certain embodiments, at least one R$^A$ is butyl. In certain embodiments, at least one R$^A$ is pentyl. In certain embodiments, at least one R$^A$ is hexyl. In certain embodiments, at least one R$^A$ is substituted alkenyl. In certain embodiments, at least one R$^A$ is unsubstituted alkenyl. In certain embodiments, at least one R$^A$ is vinyl. In certain embodiments, at least one R$^A$ is substituted alkynyl. In certain embodiments, at least one R$^A$ is unsubstituted alkynyl. In certain embodiments, at least one R$^A$ is ethynyl. In certain embodiments, at least one R$^A$ is substituted carbocycly. In certain embodiments, at least one R is substituted R$^A$ is unsubstituted carbocyclyl. In certain embodiments, at least one R$^A$ is cylcopropyl. In certain embodiments, at least one R$^A$ is cylcobutyl. In certain embodiments, at least one R$^A$ is cyclopentyl. In certain embodiments, at least one R$^A$ is cyclohexyl. In certain embodiments, at least one R$^A$ is cycloheptyl. In certain embodiments, at least one R$^A$ is substituted heterocyclyl. In certain embodiments, at least one R$^A$ is unsubstituted heterocyclyl. In certain embodiments, at least one R$^A$ is substituted aryl. In certain embodiments, at least one R$^A$ is unsubstituted aryl. In certain embodiments, at least one R$^A$ is substituted phenyl. In certain embodiments, at least one R$^A$ is unsubstituted phenyl. In certain embodiments, at least one R$^A$ is substituted naphthyl. In certain embodiments, at least one R$^A$ is unsubstituted naphthyl. In certain embodiments, at least one R$^A$ is substituted heteroaryl. In certain embodiments, at least one R$^A$ is unsubstituted heteroaryl. In certain embodiments, at least one R$^A$ is monocyclic heteroaryl. In certain embodiments, at least one R$^A$ is 5-membered monocyclic heteroaryl. In certain embodiments, at least one R$^A$ is 5-membered monocyclic heteroaryl, wherein only one of the five atoms in the ring of the heteroaryl is nitrogen, oxygen, or sulfur. In certain embodiments, at least one R$^A$ is 5-membered monocyclic heteroaryl, wherein only two of the five atoms in the ring of the heteroaryl are independently nitrogen, oxygen, or sulfur. In certain embodiments, at least one R$^A$ is 5-membered monocyclic heteroaryl, wherein only three of the five atoms in the ring of the heteroaryl are independently nitrogen, oxygen, or sulfur. In certain embodiments, at least one R$^A$ is tetrazolyl. In certain embodiments, at least one R$^A$ is 6-membered monocyclic heteroaryl. In certain embodiments, at least one R$^A$ is 6-membered monocyclic heteroaryl, wherein only one of the six atoms in the ring of the heteroaryl is nitrogen. In certain embodiments, at least one R$^A$ is 6-membered monocyclic heteroaryl, wherein only two of the six atoms in the ring of the heteroaryl are nitrogen. In certain embodiments, at least one R$^A$ is triazinyl. In certain embodiments, at least one R$^A$ is tetrazinyl. In certain embodiments, at least one R$^A$ is bicyclic heteroaryl, wherein the point of attachment may be on any atom of the bicyclic heteroaryl ring system, as valency permits. In certain embodiments, at least one R$^A$ is a monocyclic heteroaryl ring fused with phenyl. In certain embodiments, at least one R$^A$ is a 5-membered monocyclic heteroaryl ring fused with phenyl. In certain embodiments, at least one R$^A$ is a 6-membered monocyclic heteroaryl ring fused with phenyl. In certain embodiments, at least one R$^A$ is a monocyclic heteroaryl ring fused with another monocyclic heteroaryl. In certain embodiments, at least one R$^A$ is a 5-membered monocyclic heteroaryl ring fused with another 5-membered monocyclic heteroaryl. In certain embodiments, at least one R$^A$ is a 5-membered monocyclic heteroaryl ring fused with a 6-membered monocyclic heteroaryl. In certain embodiments, at least one R$^A$ is a 6-membered monocyclic heteroaryl fused with another 6-membered monocyclic heteroaryl. In certain embodiments, at least one $R^A$ is —$OR^{A1}$. In certain embodiments, at least one $R^A$ is —OMe. In certain embodiments, at least one $R^A$ is —OEt. In certain embodiments, at least one $R^A$ is —OPr. In certain embodiments, at least one $R^A$ is —OBu. In certain embodiments, at least one $R^A$ is —O(pentyl). In certain embodiments, at least one $R^A$ is —O(hexyl). In certain embodiments, at least one $R^A$ is —OPh. In certain embodiments, at least one $R^A$ is —OBn. In certain embodiments, at least one $R^A$ is —O(CH$_2$)$_2$Ph. In certain embodiments, at least one $R^A$ is —OH. In certain embodiments, at least one $R^A$ is —SR$^A$(C)Ph. In certain embodiments, at least one $R^A$ is —SH. In certain embodiments, at least one $R^A$ is —N(R$^{A1}$)$_2$. In certain embodiments, at least one $R^A$ is —NH$_2$. In certain embodiments, at least one $R^A$ is —CN. In certain embodiments, at least one $R^A$ is —SCN. In certain embodiments, at least one $R^A$ is —C(=NR$^{A1}$)R$^{A1}$, —C(=NR$^{A1}$)OR$^{A1}$, or —C(=NR$^{A1}$)N(R$^{A1}$)$_2$. In certain embodiments, at least one $R^A$ is —C(=O)R$^{A1}$, —C(=O)OR$^{A1}$, or —C(=O)N(R$^{A1}$)$_2$. In certain embodiments, at least one $R^A$ is —NO$_2$. In certain embodiments, at least one $R^A$ is —NR$^{A1}$C(=O)R$^{A1}$, —NR$^{A1}$C(=O)OR$^{A1}$, or —NR$^{A1}$C(=O)N(R$^{A1}$)$_2$. In certain embodiments, at least one $R^A$ is —OC(=O)R$^{A1}$, —OC(=O)OR$^{A1}$, or —OC(=O)N(R$^{A1}$)$_2$. In certain embodiments, at least one $R^A$ is a nitrogen protecting group when attached to a nitrogen atom. In certain embodiments, at least one $R^A$ is Bn, BOC, Cbz, Fmoc, trifluoroacetyl, triphenylmethyl, or Ts when attached to a nitrogen atom.

In compounds of Formula (I), two $R^A$ groups may be joined to form a substituted or unsubstituted carbocyclic ring. In certain embodiments, two $R^A$ groups are joined to form a substituted or unsubstituted cyclopropyl ring. In certain embodiments, two $R^A$ groups are joined to form a substituted or unsubstituted cyclobutyl ring. In certain embodiments, two $R^A$ groups are joined to form a substituted or unsubstituted cyclopentyl ring. In certain embodiments, two $R^A$ groups are joined to form a substituted or unsubstituted cyclohexyl ring. In certain embodiments, two $R^A$ groups are joined to form a substituted or unsubstituted cycloheptyl ring.

In certain embodiments, two $R^A$ groups are joined to form a substituted or unsubstituted heterocyclic ring. In certain embodiments, two $R^A$ groups are joined to form a substituted or unsubstituted 4-membered heterocyclic ring. In certain embodiments, two $R^A$ groups are joined to form a substituted or unsubstituted 5-membered heterocyclic ring. In certain embodiments, two $R^A$ groups are joined to form a substituted or unsubstituted 6-membered heterocyclic ring. In certain embodiments, two $R^A$ groups are joined to form a substituted or unsubstituted 7-membered heterocyclic ring.

In certain embodiments, two $R^A$ groups are joined to form a substituted or unsubstituted aryl ring. In certain embodiments, two $R^A$ groups are joined to form a substituted or unsubstituted monocyclic aryl ring. In certain embodiments, two $R^A$ groups are joined to form a substituted or unsubstituted phenyl ring. In certain embodiments, two $R^A$ groups are joined to form a substituted or unsubstituted bicyclic aryl ring. In certain embodiments, two $R^A$ groups are joined to form a substituted or unsubstituted naphthyl ring.

In certain embodiments, two $R^A$ groups are joined to form a substituted or unsubstituted heteroaryl ring. In certain embodiments, two $R^A$ groups are joined to form a substituted or unsubstituted monocyclic heteroaryl ring. In certain embodiments, two $R^A$ groups are joined to form a substituted or unsubstituted 5-membered monocyclic heteroaryl ring. In certain embodiments, two $R^A$ groups are joined to form a substituted or unsubstituted 6-membered monocyclic heteroaryl ring. In certain embodiments, two $R^A$ groups are joined to form a substituted or unsubstituted, bicyclic heteroaryl ring. In certain embodiments, two $R^A$ groups are joined to form a substituted or unsubstituted, 5,6-membered bicyclic heteroaryl ring. In certain embodiments, two $R^A$ groups are joined to form a substituted or unsubstituted, 6,5-membered bicyclic heteroaryl ring. In certain embodiments, two $R^A$ groups are joined to form a substituted or unsubstituted, 6,6-membered bicyclic heteroaryl ring.

In certain embodiments, at least one $R^A$ is halogen, substituted or unsubstituted $C_{1-6}$ alkyl, or —$OR^{A1}$. In certain embodiments, at least one $R^A$ is F, Cl, —CH$_3$, —CF$_3$, Et, Bn, —OMe, or —OEt.

In certain embodiments, at least one $R^{A1}$ is H. In certain embodiments, at least one $R^{A1}$ is substituted acyl. In certain embodiments, at least one $R^{A1}$ is unsubstituted acyl. In certain embodiments, at least one $R^{A1}$ is acetyl. In certain embodiments, at least one $R^{A1}$ is substituted alkyl. In certain embodiments, at least one $R^{A1}$ is unsubstituted alkyl. In certain embodiments, at least one $R^{A1}$ is $C_{1-6}$ alkyl. In certain embodiments, at least one $R^{A1}$ is methyl. In certain embodiments, at least one $R^{A1}$ is ethyl. In certain embodiments, at least one $R^{A1}$ is propyl. In certain embodiments, at least one $R^{A1}$ is butyl. In certain embodiments, at least one $R^{A1}$ is pentyl. In certain embodiments, at least one $R^{A1}$ is hexyl. In certain embodiments, at least one $R^{A1}$ is substituted alkenyl. In certain embodiments, at least one $R^{A1}$ is unsubstituted alkenyl. In certain embodiments, at least one $R^{A1}$ is vinyl. In certain embodiments, at least one $R^{A1}$ is substituted alkynyl. In certain embodiments, at least one $R^{A1}$ is unsubstituted alkynyl. In certain embodiments, at least one $R^{A1}$ is ethynyl. In certain embodiments, at least one $R^{A1}$ is substituted carbocyclyl. In certain embodiments, at least one $R^{A1}$ is unsubstituted carbocyclyl. In certain embodiments, at least one $R^{A1}$ is cylcopropyl. In certain embodiments, at least one $R^{A1}$ is cylcobutyl. In certain embodiments, at least one $R^{A1}$ is cyclopentyl. In certain embodiments, at least one $R^{A1}$ is cyclohexyl. In certain embodiments, at least one $R^{A1}$ is cycloheptyl. In certain embodiments, at least one $R^{A1}$ is substituted heterocyclyl. In certain embodiments, at least one $R^{A1}$ is unsubstituted heterocyclyl. In certain embodiments, at least one $R^{A1}$ is substituted aryl. In certain embodiments, at least one $R^{A1}$ is unsubstituted aryl. In certain embodiments, at least one $R^{A1}$ is substituted phenyl. In certain embodiments, at least one $R^{A1}$ is unsubstituted phenyl. In certain embodiments, at least one $R^{A1}$ is substituted heteroaryl. In certain embodiments, at least one $R^{A1}$ is unsubstituted heteroaryl. In certain embodiments, at least one $R^{A1}$ is substituted pyridyl. In certain embodiments, at least one $R^{A1}$ is unsubstituted pyridyl. In certain embodiments, at least one $R^{A1}$ is a nitrogen protecting group when attached to a nitrogen atom. In certain embodiments, at least one $R^{A1}$ is Bn, Boc, Cbz, Fmoc, trifluoroacetyl, triphenylmethyl, or Ts when attached to a nitrogen atom. In certain embodiments, $R^{A1}$ is an oxygen protecting group when attached to an oxygen atom. In certain embodiments, $R^{A1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1}$ is a sulfur protecting group when attached to a sulfur atom. In certain embodiments, $R^{A1}$ is acetamidomethyl, t-Bu, 3-nitro-2-pyridine sulfenyl, 2-pyridine-sulfenyl, or triphenylmethyl when attached to a sulfur atom. In certain embodiments, two $R^{A1}$ groups are joined to form a substituted heterocyclic ring. In certain embodiments, two $R^{A1}$ groups are joined to form an unsubstituted heterocyclic ring. In certain embodiments, two $R^{A1}$ groups are joined to form a substituted heteroaryl ring.

In certain embodiments, two $R^{A1}$ groups are joined to form an unsubstituted heteroaryl ring.

Compounds of Formula (I) may include a substituent $R^B$ on the benzimidazole moiety. In certain embodiments, $R^B$ is H. In certain embodiments, $R^B$ is halogen. In certain embodiments, $R^B$ is F. In certain embodiments, $R^B$ is Cl. In certain embodiments, $R^B$ is Br. In certain embodiments, $R^B$ is I (iodine). In certain embodiments, $R^B$ is substituted $C_{1-6}$ alkyl. In certain embodiments, $R^B$ is unsubstituted $C_{1-6}$ alkyl. In certain embodiments, $R^B$ is methyl. In certain embodiments, $R^B$ is substituted methyl. In certain embodiments, $R^B$ is —$CH_2F$. In certain embodiments, $R^B$ is —$CHF_2$. In certain embodiments, $R^B$ is —$CF_3$. In certain embodiments, $R^B$ is Bn. In certain embodiments, $R^B$ is ethyl. In certain embodiments, $R^B$ is substituted ethyl. In certain embodiments, $R^B$ is —$(CH_2)_2Ph$. In certain embodiments, $R^B$ is propyl. In certain embodiments, $R^B$ is butyl. In certain embodiments, $R^B$ is pentyl. In certain embodiments, $R^B$ is hexyl.

Compounds of Formula (I) may include a substituent $R^C$. In certain embodiments, $R^C$ is H. In certain embodiments, $R^C$ is halogen. In certain embodiments, $R^C$ is F. In certain embodiments, $R^C$ is Cl. In certain embodiments, $R^C$ is Br. In certain embodiments, $R^C$ is I (iodine). In certain embodiments, $R^C$ is substituted $C_{1-6}$ alkyl. In certain embodiments, $R^C$ is unsubstituted $C_{1-6}$ alkyl. In certain embodiments, $R^C$ is methyl. In certain embodiments, $R^C$ is substituted methyl. In certain embodiments, $R^C$ is —$CH_2F$. In certain embodiments, $R^C$ is —$CHF_2$. In certain embodiments, $R^C$ is —$CF_3$. In certain embodiments, $R^C$ is Bn. In certain embodiments, $R^C$ is ethyl. In certain embodiments, $R^C$ is substituted ethyl. In certain embodiments, $R^C$ is —$(CH_2)_2Ph$. In certain embodiments, $R^C$ is propyl. In certain embodiments, $R^C$ is butyl. In certain embodiments, $R^C$ is pentyl. In certain embodiments, $R^C$ is hexyl.

Ring B of compounds of Formula (I) may include one or more substituents $R^D$. In certain embodiments, at least one $R^D$ is H. In certain embodiments, at least one $R^D$ is halogen. In certain embodiments, at least one $R^D$ is F. In certain embodiments, at least one $R^D$ is Cl. In certain embodiments, at least one $R^D$ is Br. In certain embodiments, at least one $R^D$ is I (iodine). In certain embodiments, at least one $R^D$ is substituted acyl. In certain embodiments, at least one $R^D$ is unsubstituted acyl. In certain embodiments, at least one $R^D$ is substituted alkyl. In certain embodiments, at least one $R^D$ is unsubstituted alkyl. In certain embodiments, at least one $R^D$ is $C_{1-6}$ alkyl. In certain embodiments, at least one $R^D$ is methyl. In certain embodiments, at least one $R^D$ is substituted methyl. In certain embodiments, at least one $R^D$ is —$CH_2F$. In certain embodiments, at least one $R^D$ is —$CHF_2$. In certain embodiments, at least one $R^D$ is —$CF_3$. In certain embodiments, at least one $R^D$ is Bn. In certain embodiments, at least one $R^D$ is ethyl. In certain embodiments, at least one $R^D$ is substituted ethyl. In certain embodiments, at least one $R^D$ is —$(CH_2)_2Ph$. In certain embodiments, at least one $R^D$ is propyl. In certain embodiments, at least one $R^D$ is butyl. In certain embodiments, at least one $R^D$ is pentyl. In certain embodiments, at least one $R^D$ is hexyl. In certain embodiments, at least one $R^D$ is substituted alkenyl. In certain embodiments, at least one $R^D$ is unsubstituted alkenyl. In certain embodiments, at least one $R^D$ is vinyl. In certain embodiments, at least one $R^D$ is substituted alkynyl. In certain embodiments, at least one $R^D$ is unsubstituted alkynyl. In certain embodiments, at least one $R^D$ is ethynyl. In certain embodiments, at least one $R^D$ is substituted carbocyclyl. In certain embodiments, at least one $R^D$ is unsubstituted carbocyclyl. In certain embodiments, at least one $R^D$ is cylcopropyl. In certain embodiments, at least one $R^D$ is cylcobutyl. In certain embodiments, at least one $R^D$ is cyclopentyl. In certain embodiments, at least one $R^D$ is cyclohexyl. In certain embodiments, at least one $R^D$ is cycloheptyl. In certain embodiments, at least one $R^D$ is substituted heterocyclyl. In certain embodiments, at least one $R^D$ is unsubstituted heterocyclyl. In certain embodiments, at least one $R^D$ is substituted aryl. In certain embodiments, at least one $R^D$ is unsubstituted aryl. In certain embodiments, at least one $R^D$ is substituted phenyl. In certain embodiments, at least one $R^D$ is unsubstituted phenyl. In certain embodiments, at least one $R^D$ is substituted naphthyl. In certain embodiments, at least one $R^D$ is unsubstituted naphthyl. In certain embodiments, at least one $R^D$ is substituted heteroaryl. In certain embodiments, at least one $R^D$ is unsubstituted heteroaryl. In certain embodiments, at least one $R^D$ is monocyclic heteroaryl. In certain embodiments, at least one $R^D$ is 5-membered monocyclic heteroaryl. In certain embodiments, at least one $R^D$ is 5-membered monocyclic heteroaryl, wherein only one of the five atoms in the ring of the heteroaryl is nitrogen, oxygen, or sulfur. In certain embodiments, at least one $R^D$ is 5-membered monocyclic heteroaryl, wherein only two of the five atoms in the ring of the heteroaryl are independently nitrogen, oxygen, or sulfur. In certain embodiments, at least one $R^D$ is 5-membered monocyclic heteroaryl, wherein only three of the five atoms in the ring of the heteroaryl are independently nitrogen, oxygen, or sulfur. In certain embodiments, at least one $R^D$ is tetrazolyl. In certain embodiments, at least one $R^D$ is 6-membered monocyclic heteroaryl. In certain embodiments, at least one $R^D$ is 6-membered monocyclic heteroaryl, wherein only one of the six atoms in the ring of the heteroaryl is nitrogen. In certain embodiments, at least one $R^D$ is 6-membered monocyclic heteroaryl, wherein only two of the six atoms in the ring of the heteroaryl are nitrogen. In certain embodiments, at least one $R^D$ is triazinyl. In certain embodiments, at least one $R^D$ is tetrazinyl. In certain embodiments, at least one $R^D$ is bicyclic heteroaryl, wherein the point of attachment may be on any atom of the bicyclic heteroaryl ring system, as valency permits. In certain embodiments, at least one $R^D$ is a monocyclic heteroaryl ring fused with phenyl. In certain embodiments, at least one $R^D$ is a 5-membered monocyclic heteroaryl ring fused with phenyl. In certain embodiments, at least one $R^D$ is a 6-membered monocyclic heteroaryl ring fused with phenyl. In certain embodiments, at least one $R^D$ is a monocyclic heteroaryl ring fused with another monocyclic heteroaryl. In certain embodiments, at least one $R^D$ is a 5-membered monocyclic heteroaryl ring fused with another 5-membered monocyclic heteroaryl. In certain embodiments, at least one $R^D$ is a 5-membered monocyclic heteroaryl ring fused with a 6-membered monocyclic heteroaryl. In certain embodiments, at least one $R^D$ is a 6-membered monocyclic heteroaryl fused with another 6-membered monocyclic heteroaryl. In certain embodiments, at least one $R^D$ is —$OR^{D1}$. In certain embodiments, at least one $R^D$ is —OMe. In certain embodiments, at least one $R^D$ is —OEt. In certain embodiments, at least one $R^D$ is —OPr. In certain embodiments, at least one $R^D$ is —OBu. In certain embodiments, at least one $R^D$ is —O(pentyl). In certain embodiments, at least one $R^D$ is —O(hexyl). In certain embodiments, at least one $R^D$ is —OPh. In certain embodiments, at least one $R^D$ is —OBn. In certain embodiments, at least one $R^D$ is —$O(CH_2)_2Ph$. In certain embodiments, at least one $R^D$ is —OH. In certain embodiments, at least one $R^D$ is —$SR^D$. In certain embodiments, at least one $R^D$ is —SH. In certain embodiments, at least one $R^D$ is —$N(R^D)_2$.

In certain embodiments, at least one $R^D$ is —NH$_2$. In certain embodiments, at least one $R^D$ is —CN. In certain embodiments, at least one $R^D$ is —SCN. In certain embodiments, at least one $R^D$ is —C(=NR$^{D1}$)R$^{D1}$, —C(=NR$^{D1}$)OR$^{D1}$, or —C(=NR$^D$)N(R$^D$)$_2$. In certain embodiments, at least one $R^D$ is —C(=O)R$^{D1}$, —C(=O)OR$^{D1}$, or —C(=O)N(R$^{D1}$)$_2$. In certain embodiments, at least one $R^D$ is —NO$_2$. In certain embodiments, at least one $R^D$ is —NR$^{D1}$C(=O)R$^{D1}$, —NR$^{D1}$C(=O)OR$^{D1}$, or —NR$^{D1}$C(=O)N(R$^D$)$_2$. In certain embodiments, at least one $R^D$ is —OC(=O)R$^{D1}$, —OC(=O)OR$^{D1}$, or —OC(=O)N(R$^{D1}$)$_2$. In certain embodiments, at least one $R^D$ is a nitrogen protecting group when attached to a nitrogen atom. In certain embodiments, at least one $R^D$ is Bn, BOC, Cbz, Fmoc, trifluoroacetyl, triphenylmethyl, or Ts when attached to a nitrogen atom.

In compounds of Formula (I), two $R^D$ groups may be joined to form a substituted or unsubstituted carbocyclic ring. In certain embodiments, two $R^D$ groups are joined to form a substituted or unsubstituted cyclopropyl ring. In certain embodiments, two $R^D$ groups are joined to form a substituted or unsubstituted cyclobutyl ring. In certain embodiments, two $R^D$ groups are joined to form a substituted or unsubstituted cyclopentyl ring. In certain embodiments, two $R^D$ groups are joined to form a substituted or unsubstituted cyclohexyl ring. In certain embodiments, two $R^D$ groups are joined to form a substituted or unsubstituted cycloheptyl ring.

In certain embodiments, two $R^D$ groups are joined to form a substituted or unsubstituted heterocyclic ring. In certain embodiments, two $R^D$ groups are joined to form a substituted or unsubstituted 4-membered heterocyclic ring. In certain embodiments, two $R^D$ groups are joined to form a substituted or unsubstituted 5-membered heterocyclic ring. In certain embodiments, two $R^D$ groups are joined to form a substituted or unsubstituted 6-membered heterocyclic ring. In certain embodiments, two $R^D$ groups are joined to form a substituted or unsubstituted 7-membered heterocyclic ring.

In certain embodiments, two $R^D$ groups are joined to form a substituted or unsubstituted aryl ring. In certain embodiments, two $R^D$ groups are joined to form a substituted or unsubstituted monocyclic aryl ring. In certain embodiments, two $R^D$ groups are joined to form a substituted or unsubstituted phenyl ring. In certain embodiments, two $R^D$ groups are joined to form a substituted or unsubstituted bicyclic aryl ring. In certain embodiments, two $R^D$ groups are joined to form a substituted or unsubstituted naphthyl ring.

In certain embodiments, two $R^D$ groups are joined to form a substituted or unsubstituted heteroaryl ring. In certain embodiments, two $R^D$ groups are joined to form a substituted or unsubstituted monocyclic heteroaryl ring. In certain embodiments, two $R^D$ groups are joined to form a substituted or unsubstituted 5-membered monocyclic heteroaryl ring. In certain embodiments, two $R^D$ groups are joined to form a substituted or unsubstituted 6-membered monocyclic heteroaryl ring. In certain embodiments, two $R^D$ groups are joined to form a substituted or unsubstituted, bicyclic heteroaryl ring. In certain embodiments, two $R^D$ groups are joined to form a substituted or unsubstituted, 5,6-membered bicyclic heteroaryl ring. In certain embodiments, two $R^D$ groups are joined to form a substituted or unsubstituted, 6,5-membered bicyclic heteroaryl ring. In certain embodiments, two $R^D$ groups are joined to form a substituted or unsubstituted, 6,6-membered bicyclic heteroaryl ring.

In certain embodiments, at least one $R^D$ is halogen, substituted or unsubstituted C$_{1-6}$ alkyl, or —OR$^{D1}$. In certain embodiments, at least one $R^D$ is F, Cl, Br, Me, —CH$_2$F, —CHF$_2$, —CF$_3$, Et, —OMe, or —OEt.

In certain embodiments, at least one $R^{D1}$ is H. In certain embodiments, at least one $R^{D1}$ is substituted acyl. In certain embodiments, at least one $R^{D1}$ is unsubstituted acyl. In certain embodiments, at least one $R^{D1}$ is acetyl. In certain embodiments, at least one $R^{D1}$ is substituted alkyl. In certain embodiments, at least one $R^{D1}$ is unsubstituted alkyl. In certain embodiments, at least one $R^{D1}$ is C$_{1-6}$ alkyl. In certain embodiments, at least one $R^{D1}$ is methyl. In certain embodiments, at least one $R^{D1}$ is ethyl. In certain embodiments, at least one $R^{D1}$ is propyl. In certain embodiments, at least one $R^{D1}$ is butyl. In certain embodiments, at least one $R^{D1}$ is pentyl. In certain embodiments, at least one $R^{D1}$ is hexyl. In certain embodiments, at least one $R^{D1}$ is substituted alkenyl. In certain embodiments, at least one $R^{D1}$ is unsubstituted alkenyl. In certain embodiments, at least one $R^{D1}$ is vinyl. In certain embodiments, at least one $R^{D1}$ is substituted alkynyl. In certain embodiments, at least one $R^{D1}$ is unsubstituted alkynyl. In certain embodiments, at least one $R^{D1}$ is ethynyl. In certain embodiments, at least one $R^{D1}$ is substituted carbocyclyl. In certain embodiments, at least one $R^{D1}$ is unsubstituted carbocyclyl. In certain embodiments, at least one $R^{D1}$ is cylcopropyl. In certain embodiments, at least one $R^{D1}$ is cylcobutyl. In certain embodiments, at least one $R^{D1}$ is cyclopentyl. In certain embodiments, at least one $R^{D1}$ is cyclohexyl. In certain embodiments, at least one $R^{D1}$ is cycloheptyl. In certain embodiments, at least one $R^{D1}$ is substituted heterocyclyl. In certain embodiments, at least one $R^{D1}$ is unsubstituted heterocyclyl. In certain embodiments, at least one $R^{D1}$ is substituted aryl. In certain embodiments, at least one $R^{D1}$ is unsubstituted aryl. In certain embodiments, at least one $R^{D1}$ is substituted phenyl. In certain embodiments, at least one $R^{D1}$ is unsubstituted phenyl. In certain embodiments, at least one $R^{D1}$ is substituted heteroaryl. In certain embodiments, at least one $R^{D1}$ is unsubstituted heteroaryl. In certain embodiments, at least one $R^{D1}$ is substituted pyridyl. In certain embodiments, at least one $R^{D1}$ is unsubstituted pyridyl. In certain embodiments, at least one $R^{D1}$ is a nitrogen protecting group when attached to a nitrogen atom. In certain embodiments, at least one $R^{D1}$ is Bn, Boc, Cbz, Fmoc, trifluoroacetyl, triphenylmethyl, or Ts when attached to a nitrogen atom. In certain embodiments, $R^{D1}$ is an oxygen protecting group when attached to an oxygen atom. In certain embodiments, $R^{D1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1}$ is a sulfur protecting group when attached to a sulfur atom. In certain embodiments, $R^{D1}$ is acetamidomethyl, t-Bu, 3-nitro-2-pyridine sulfenyl, 2-pyridine-sulfenyl, or triphenylmethyl when attached to a sulfur atom. In certain embodiments, two $R^{D1}$ groups are joined to form a substituted heterocyclic ring. In certain embodiments, two $R^{D1}$ groups are joined to form an unsubstituted heterocyclic ring. In certain embodiments, two $R^{D1}$ groups are joined to form a substituted heteroaryl ring. In certain embodiments, two $R^{D1}$ groups are joined to form an unsubstituted heteroaryl ring.

Compounds of Formula (I) may include a substituent $R^E$. In certain embodiments, $R^E$ is H. In certain embodiments, $R^E$ is substituted C$_{1-6}$ alkyl. In certain embodiments, $R^E$ is unsubstituted C$_{1-6}$ alkyl. In certain embodiments, $R^E$ is methyl. In certain embodiments, $R^E$ is substituted methyl. In certain embodiments, $R^E$ is —CH$_2$F. In certain embodiments, $R^E$ is —CHF$_2$. In certain embodiments, $R^E$ is —CF$_3$. In certain embodiments, $R^E$ is Bn. In certain embodiments, $R^E$ is ethyl. In certain embodiments, $R^E$ is substituted ethyl. In certain embodiments, $R^E$ is —(CH$_2$)$_2$Ph. In certain embodiments, $R^E$ is propyl. In certain embodiments, $R^E$ is butyl. In certain embodiments, $R^E$ is pentyl. In certain embodiments, $R^E$ is hexyl. In certain embodiments, $R^E$ is a nitrogen protecting group. In certain embodiments, $R^E$ is Bn, BOC, Cbz, Fmoc, trifluoroacetyl, triphenylmethyl, or Ts.

Compounds of Formula (I) may include one or more substituents $R^F$ on the benzimidazolyl moiety. In certain embodiments, at least one $R^F$ is H. In certain embodiments, at least one $R^F$ is halogen. In certain embodiments, at least one $R^F$ is F. In certain embodiments, at least one $R^F$ is Cl. In certain embodiments, at least one $R^F$ is Br. In certain embodiments, at least one $R^F$ is I (iodine). In certain embodiments, at least one $R^F$ is substituted acyl. In certain embodiments, at least one $R^F$ is unsubstituted acyl. In certain embodiments, at least one $R^F$ is substituted alkyl. In certain embodiments, at least one R is unsubstituted alkyl. In certain embodiments, at least one $R^F$ is $C_{1-6}$ alkyl. In certain embodiments, at least one $R^F$ is methyl. In certain embodiments, at least one $R^F$ is substituted methyl. In certain embodiments, at least one $R^F$ is —$CH_2F$. In certain embodiments, at least one $R^F$ is —$CHF_2$. In certain embodiments, at least one $R^F$ is —$CF_3$. In certain embodiments, at least one $R^F$ is Bn. In certain embodiments, at least one $R^F$ is ethyl. In certain embodiments, at least one $R^F$ is substituted ethyl. In certain embodiments, at least one $R^F$ is —$(CH_2)_2$Ph. In certain embodiments, at least one $R^F$ is propyl. In certain embodiments, at least one $R^F$ is butyl. In certain embodiments, at least one $R^F$ is pentyl. In certain embodiments, at least one $R^F$ is hexyl. In certain embodiments, at least one $R^F$ is substituted alkenyl. In certain embodiments, at least one $R^F$ is unsubstituted alkenyl. In certain embodiments, at least one $R^F$ is vinyl. In certain embodiments, at least one $R^F$ is substituted alkynyl. In certain embodiments, at least one $R^F$ is unsubstituted alkynyl. In certain embodiments, at least one $R^F$ is ethynyl. In certain embodiments, at least one $R^F$ is substituted carbocyclyl. In certain embodiments, at least one $R^F$ is unsubstituted carbocyclyl. In certain embodiments, at least one $R^F$ is cylcopropyl. In certain embodiments, at least one $R^F$ is cylcobutyl. In certain embodiments, at least one $R^F$ is cyclopentyl. In certain embodiments, at least one $R^F$ is cyclohexyl. In certain embodiments, at least one $R^F$ is cycloheptyl. In certain embodiments, at least one $R^F$ is substituted heterocyclyl. In certain embodiments, at least one $R^F$ is unsubstituted heterocyclyl. In certain embodiments, at least one $R^F$ is substituted aryl. In certain embodiments, at least one $R^F$ is unsubstituted aryl. In certain embodiments, at least one $R^F$ is substituted phenyl. In certain embodiments, at least one $R^F$ is unsubstituted phenyl. In certain embodiments, at least one $R^F$ is substituted naphthyl. In certain embodiments, at least one $R^F$ is unsubstituted naphthyl. In certain embodiments, at least one $R^F$ is substituted heteroaryl. In certain embodiments, at least one $R^F$ is unsubstituted heteroaryl. In certain embodiments, at least one $R^F$ is monocyclic heteroaryl. In certain embodiments, at least one $R^F$ is 5-membered monocyclic heteroaryl. In certain embodiments, at least one $R^F$ is 5-membered monocyclic heteroaryl, wherein only one of the five atoms in the ring of the heteroaryl is nitrogen, oxygen, or sulfur. In certain embodiments, at least one $R^F$ is 5-membered monocyclic heteroaryl, wherein only two of the five atoms in the ring of the heteroaryl are independently nitrogen, oxygen, or sulfur. In certain embodiments, at least one $R^F$ is 5-membered monocyclic heteroaryl, wherein only three of the five atoms in the ring of the heteroaryl are independently nitrogen, oxygen, or sulfur. In certain embodiments, at least one $R^F$ is tetrazolyl. In certain embodiments, at least one $R^F$ is 6-membered monocyclic heteroaryl. In certain embodiments, at least one $R^F$ is 6-membered monocyclic heteroaryl, wherein only one of the six atoms in the ring of the heteroaryl is nitrogen. In certain embodiments, at least one $R^F$ is 6-membered monocyclic heteroaryl, wherein only two of the six atoms in the ring of the heteroaryl are nitrogen. In certain embodiments, at least one $R^F$ is triazinyl. In certain embodiments, at least one $R^F$ is tetrazinyl. In certain embodiments, at least one $R^F$ is bicyclic heteroaryl, wherein the point of attachment may be on any atom of the bicyclic heteroaryl ring system, as valency permits. In certain embodiments, at least one $R^F$ is a monocyclic heteroaryl ring fused with phenyl. In certain embodiments, at least one $R^F$ is a 5-membered monocyclic heteroaryl ring fused with phenyl. In certain embodiments, at least one $R^F$ is a 6-membered monocyclic heteroaryl ring fused with phenyl. In certain embodiments, at least one $R^F$ is a monocyclic heteroaryl ring fused with another monocyclic heteroaryl. In certain embodiments, at least one $R^F$ is a 5-membered monocyclic heteroaryl ring fused with another 5-membered monocyclic heteroaryl. In certain embodiments, at least one $R^F$ is a 5-membered monocyclic heteroaryl ring fused with a 6-membered monocyclic heteroaryl. In certain embodiments, at least one $R^F$ is a 6-membered monocyclic heteroaryl fused with another 6-membered monocyclic heteroaryl. In certain embodiments, at least one $R^F$ is —$OR^{F1}$. In certain embodiments, at least one $R^F$ is —OMe. In certain embodiments, at least one $R^F$ is —OEt. In certain embodiments, at least one $R^F$ is —OPr. In certain embodiments, at least one $R^F$ is —OBu. In certain embodiments, at least one $R^F$ is —O(pentyl). In certain embodiments, at least one $R^F$ is —O(hexyl). In certain embodiments, at least one $R^F$ is —OPh. In certain embodiments, at least one $R^F$ is —OBn. In certain embodiments, at least one $R^F$ is —$O(CH_2)_2$Ph. In certain embodiments, at least one $R^F$ is —OH. In certain embodiments, at least one $R^F$ is —$SR^{F1}$. In certain embodiments, at least one $R^F$ is —SH. In certain embodiments, at least one $R^F$ is —$N(R^{F1})_2$. In certain embodiments, at least one $R^F$ is —$NH_2$. In certain embodiments, at least one $R^F$ is —CN. In certain embodiments, at least one $R^F$ is —SCN. In certain embodiments, at least one $R^F$ is —C($=NR^{F1}$)$R^{F1}$, —C($=$NR F)$OR^{F1}$, or —C($=NR^{F1}$)N($R^{F1}$)$_2$. In certain embodiments, at least one $R^F$ is —C($=$O)$R^{F1}$, —C($=$O)$OR^{F1}$, or —C($=$O)N($R^{F1}$)$_2$. In certain embodiments, at least one $R^F$ is —$NO_2$. In certain embodiments, at least one $R^F$ is —$NR^{F1}$C($=$O)$R^{F1}$, —$NR^{F1}$C($=$O)$OR^{F1}$, or —$NR^{F1}$C($=$O)N($R^{F1}$)$_2$. In certain embodiments, at least one $R^F$ is —OC($=$O)$R^{F1}$, —OC($=$O)$OR^{F1}$, or —OC($=$O)N($R^{F1}$)$_2$. In certain embodiments, at least one $R^F$ is a nitrogen protecting group when attached to a nitrogen atom. In certain embodiments, at least one $R^F$ is Bn, BOC, Cbz, Fmoc, trifluoroacetyl, triphenylmethyl, or Ts when attached to a nitrogen atom.

In compounds of Formula (I), two $R^F$ groups may be joined to form a substituted or unsubstituted carbocyclic ring. In certain embodiments, two $R^F$ groups are joined to form a substituted or unsubstituted cyclopropyl ring. In certain embodiments, two $R^F$ groups are joined to form a substituted or unsubstituted cyclobutyl ring. In certain embodiments, two $R^F$ groups are joined to form a substituted or unsubstituted cyclopentyl ring. In certain embodiments, two $R^F$ groups are joined to form a substituted or unsubstituted cyclohexyl ring. In certain embodiments, two $R^F$ groups are joined to form a substituted or unsubstituted cycloheptyl ring.

In certain embodiments, two $R^F$ groups are joined to form a substituted or unsubstituted heterocyclic ring. In certain embodiments, two $R^F$ groups are joined to form a substituted or unsubstituted 4-membered heterocyclic ring. In certain embodiments, two $R^F$ groups are joined to form a substituted or unsubstituted 5-membered heterocyclic ring. In certain embodiments, two $R^F$ groups are joined to form a substituted or unsubstituted 6-membered heterocyclic ring. In certain embodiments, two $R^F$ groups are joined to form a substituted or unsubstituted 7-membered heterocyclic ring.

In certain embodiments, two $R^F$ groups are joined to form a substituted or unsubstituted aryl ring. In certain embodiments, two $R^F$ groups are joined to form a substituted or unsubstituted monocyclic aryl ring. In certain embodiments, two $R^F$ groups are joined to form a substituted or unsubstituted phenyl ring. In certain embodiments, two $R^F$ groups are joined to form a substituted or unsubstituted bicyclic aryl ring. In certain embodiments, two $R^F$ groups are joined to form a substituted or unsubstituted naphthyl ring.

In certain embodiments, two $R^F$ groups are joined to form a substituted or unsubstituted heteroaryl ring. In certain embodiments, two $R^F$ groups are joined to form a substituted or unsubstituted monocyclic heteroaryl ring. In certain embodiments, two $R^F$ groups are joined to form a substituted or unsubstituted 5-membered monocyclic heteroaryl ring. In certain embodiments, two $R^F$ groups are joined to form a substituted or unsubstituted 6-membered monocyclic heteroaryl ring. In certain embodiments, two $R^F$ groups are joined to form a substituted or unsubstituted, bicyclic heteroaryl ring. In certain embodiments, two $R^F$ groups are joined to form a substituted or unsubstituted, 5,6-membered bicyclic heteroaryl ring. In certain embodiments, two $R^F$ groups are joined to form a substituted or unsubstituted, 6,5-membered bicyclic heteroaryl ring. In certain embodiments, two $R^F$ groups are joined to form a substituted or unsubstituted, 6,6-membered bicyclic heteroaryl ring.

In certain embodiments, at least one $R^{F1}$ is H. In certain embodiments, at least one $R^{F1}$ is substituted acyl. In certain embodiments, at least one $R^{F1}$ is unsubstituted acyl. In certain embodiments, at least one $R^{F1}$ is acetyl. In certain embodiments, at least one $R^{F1}$ is substituted alkyl. In certain embodiments, at least one $R^{F1}$ is unsubstituted alkyl. In certain embodiments, at least one $R^{F1}$ is $C_{1-6}$ alkyl. In certain embodiments, at least one $R^{F1}$ is methyl. In certain embodiments, at least one $R^{F1}$ is ethyl. In certain embodiments, at least one $R^{F1}$ is propyl. In certain embodiments, at least one $R^{F1}$ is butyl. In certain embodiments, at least one $R^{F1}$ is pentyl. In certain embodiments, at least one $R^{F1}$ is hexyl. In certain embodiments, at least one $R^{F1}$ is substituted alkenyl. In certain embodiments, at least one $R^{F1}$ is unsubstituted alkenyl. In certain embodiments, at least one $R^{F1}$ is vinyl. In certain embodiments, at least one $R^{F1}$ is substituted alkynyl. In certain embodiments, at least one $R^{F1}$ is unsubstituted alkynyl. In certain embodiments, at least one $R^{F1}$ is ethynyl. In certain embodiments, at least one $R^{F1}$ is substituted carbocyclyl. In certain embodiments, at least one $R^{F1}$ is unsubstituted carbocyclyl. In certain embodiments, at least one $R^{F1}$ is cylcopropyl. In certain embodiments, at least one $R^{F1}$ is cylcobutyl. In certain embodiments, at least one $R^{F1}$ is cyclopentyl. In certain embodiments, at least one $R^{F1}$ is cyclohexyl. In certain embodiments, at least one $R^{F1}$ is cycloheptyl. In certain embodiments, at least one $R^{F1}$ is substituted heterocyclyl. In certain embodiments, at least one $R^{F1}$ is unsubstituted heterocyclyl. In certain embodiments, at least one $R^{F1}$ is substituted aryl. In certain embodiments, at least one $R^{F1}$ is unsubstituted aryl. In certain embodiments, at least one $R^{F1}$ is substituted phenyl. In certain embodiments, at least one $R^{F1}$ is unsubstituted phenyl. In certain embodiments, at least one $R^{F1}$ is substituted heteroaryl. In certain embodiments, at least one $R^{F1}$ is unsubstituted heteroaryl. In certain embodiments, at least one $R^{F1}$ is substituted pyridyl. In certain embodiments, at least one $R^{F1}$ is unsubstituted pyridyl. In certain embodiments, at least one $R^{F1}$ is a nitrogen protecting group when attached to a nitrogen atom. In certain embodiments, at least one $R^{F1}$ is Bn, Boc, Cbz, Fmoc, trifluoroacetyl, triphenylmethyl, or Ts when attached to a nitrogen atom. In certain embodiments, $R^{F1}$ is an oxygen protecting group when attached to an oxygen atom. In certain embodiments, $R^{F1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{F1}$ is a sulfur protecting group when attached to a sulfur atom. In certain embodiments, $R^{F1}$ is acetamidomethyl, t-Bu, 3-nitro-2-pyridine sulfenyl, 2-pyridine-sulfenyl, or triphenylmethyl when attached to a sulfur atom. In certain embodiments, two $R^{F1}$ groups are joined to form a substituted heterocyclic ring. In certain embodiments, two $R^{F1}$ groups are joined to form an unsubstituted heterocyclic ring. In certain embodiments, two $R^{F1}$ groups are joined to form a substituted heteroaryl ring. In certain embodiments, two $R^{F1}$ groups are joined to form an unsubstituted heteroaryl ring.

In compounds of Formula (I), when X is —C(=$NR^G$)—, $R^G$ may be hydrogen, substituted or unsubstituted $C_{1-6}$ alkyl, or a nitrogen protecting group. In certain embodiments, $R^G$ is H. In certain embodiments, $R^G$ is substituted $C_{1-6}$ alkyl. In certain embodiments, $R^G$ is unsubstituted $C_{1-6}$ alkyl. In certain embodiments, $R^G$ is methyl. In certain embodiments, $R^G$ is substituted methyl. In certain embodiments, $R^G$ is —$CH_2F$. In certain embodiments, $R^G$ is —$CHF_2$. In certain embodiments, $R^G$ is —$CF_3$. In certain embodiments, $R^G$ is Bn. In certain embodiments, $R^G$ is ethyl. In certain embodiments, $R^G$ is substituted ethyl. In certain embodiments, $R^G$ is —$(CH_2)_2Ph$. In certain embodiments, $R^G$ is propyl. In certain embodiments, $R^G$ is butyl. In certain embodiments, $R^G$ is pentyl. In certain embodiments, $R^G$ is hexyl. In certain embodiments, $R^G$ is a nitrogen protecting group. In certain embodiments, $R^G$ is Bn, BOC, Cbz, Fmoc, trifluoroacetyl, triphenylmethyl, or Ts.

In certain embodiments, k is 0. In certain embodiments, k is 1. In certain embodiments, k is 2. In certain embodiments, k is 3. In certain embodiments, k is 4. In certain embodiments, k is 5.

In certain embodiments, p is 0. In certain embodiments, p is 1. In certain embodiments, p is 2. In certain embodiments, p is 3. In certain embodiments, p is 4. In certain embodiments, p is 5.

In certain embodiments, m is 0. In certain embodiments, m is 1. In certain embodiments, m is 2. In certain embodiments, m is 3.

In certain embodiments, the compound of Formula (I) is of the formula:

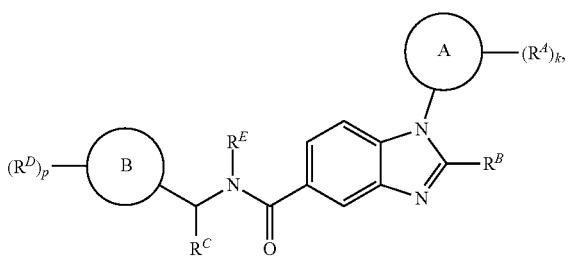

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

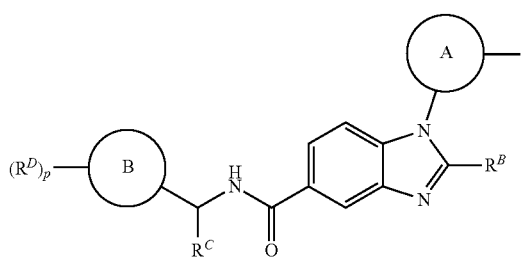

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

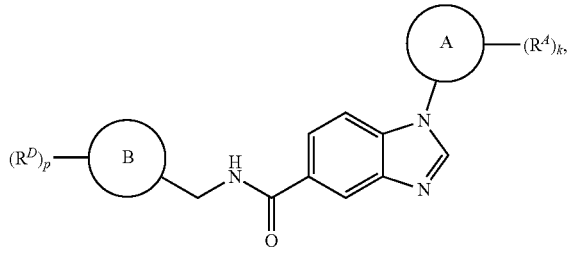

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

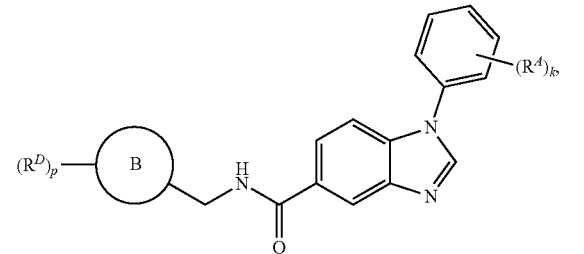

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

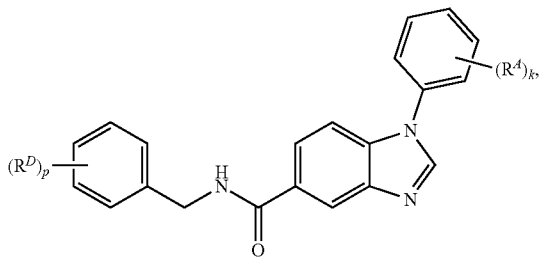

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

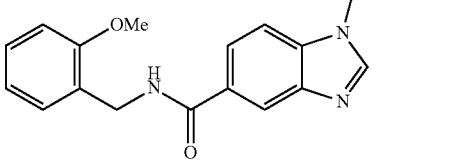

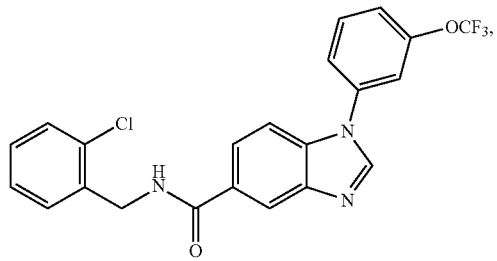

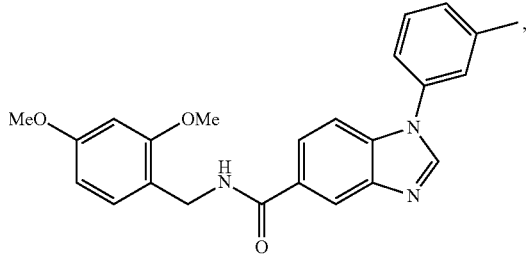

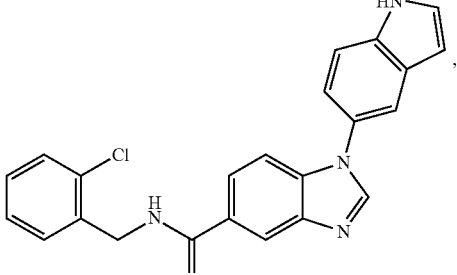

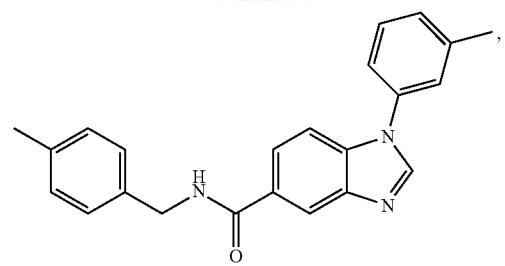
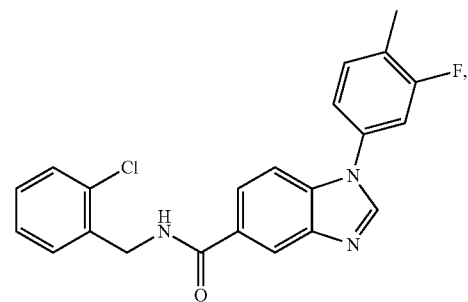
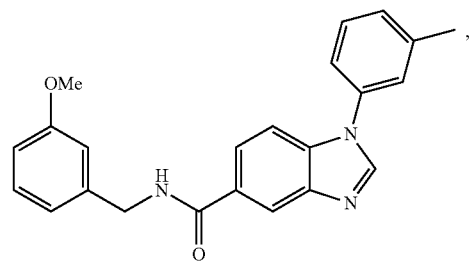
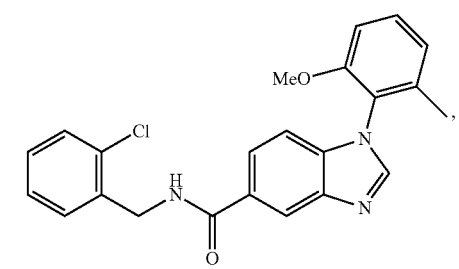
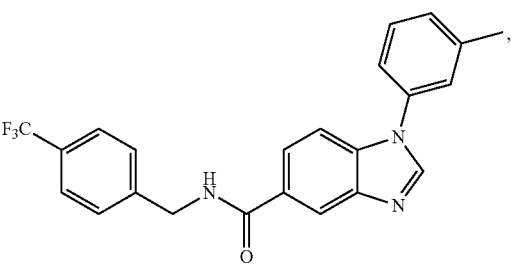
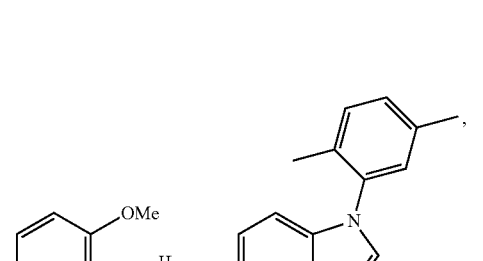
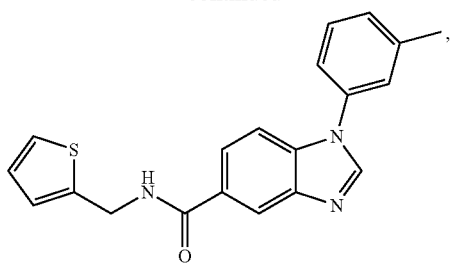
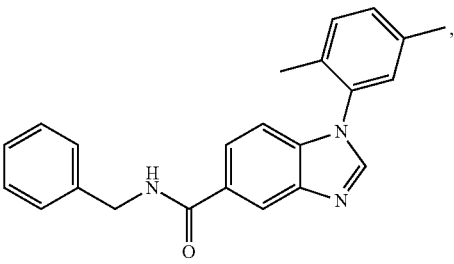
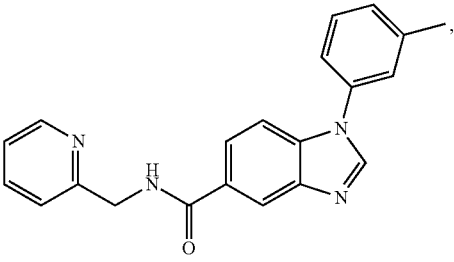
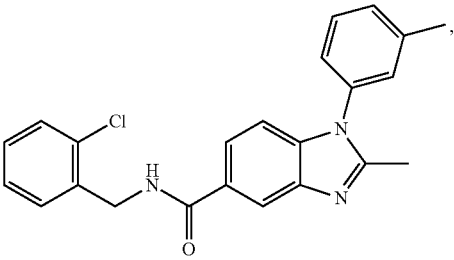
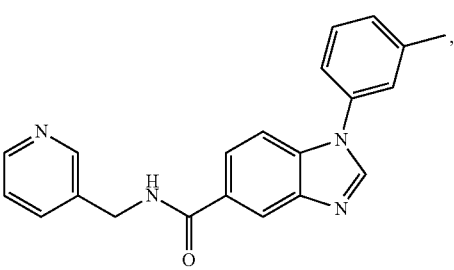
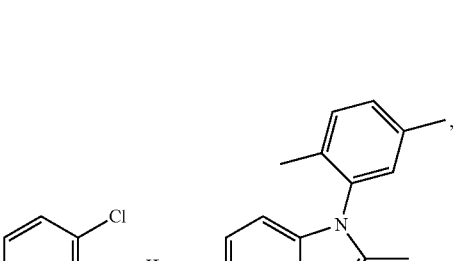

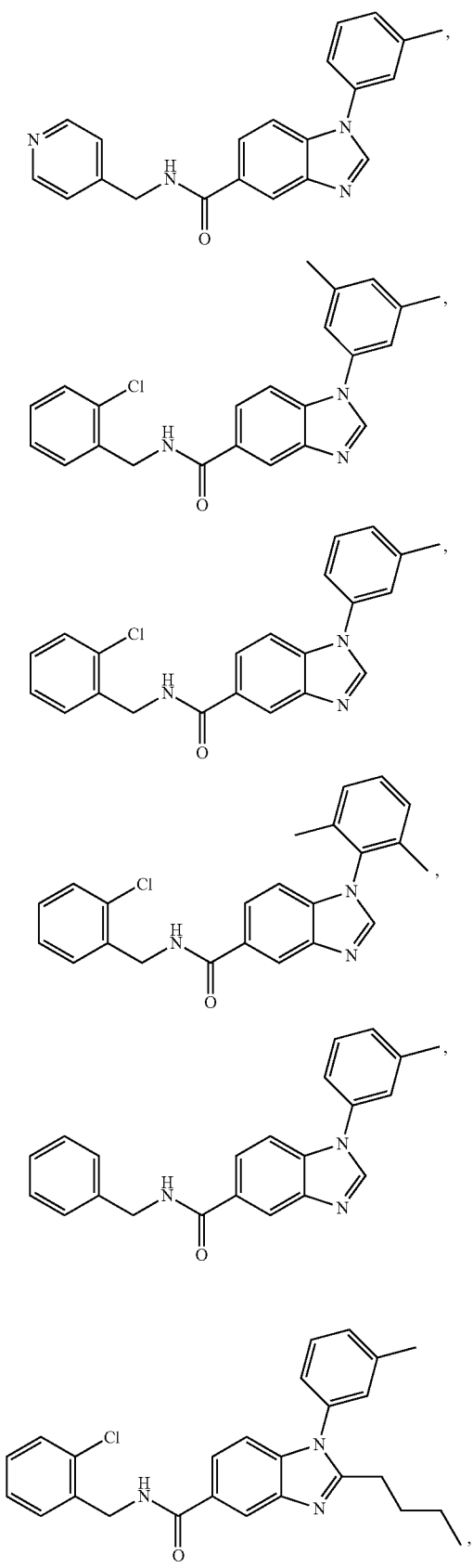
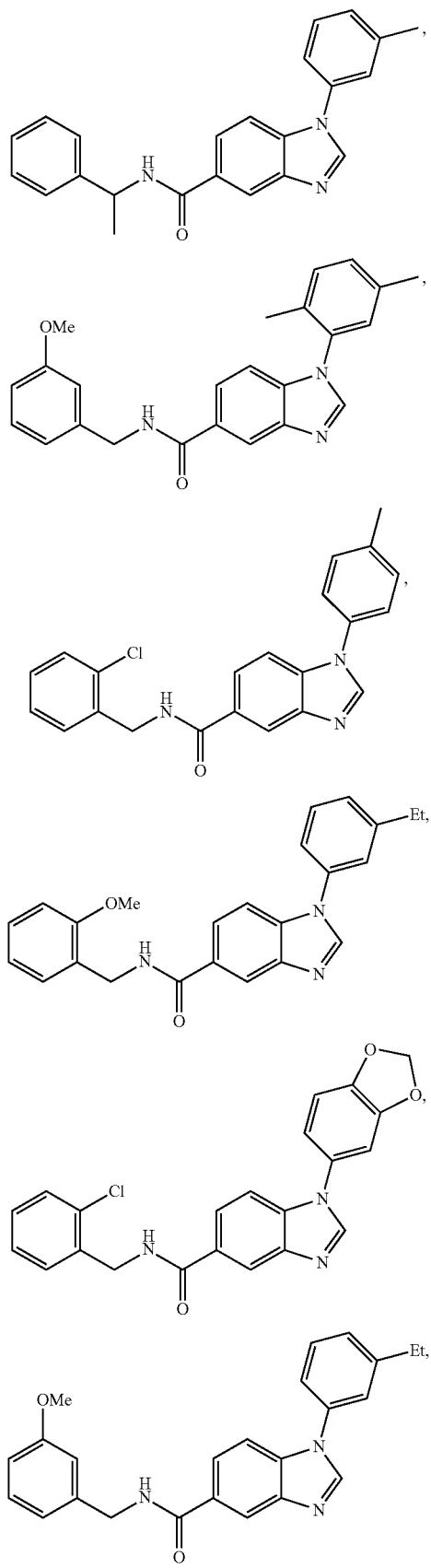

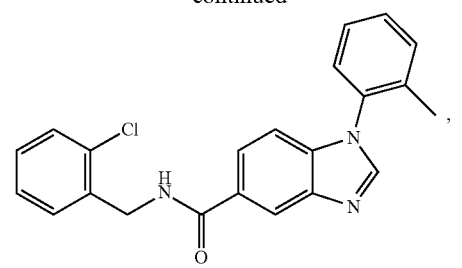
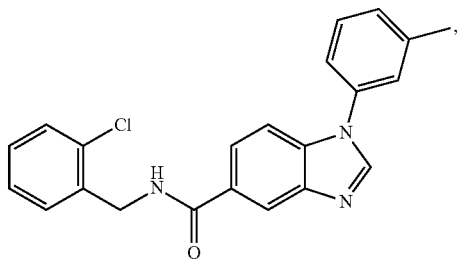
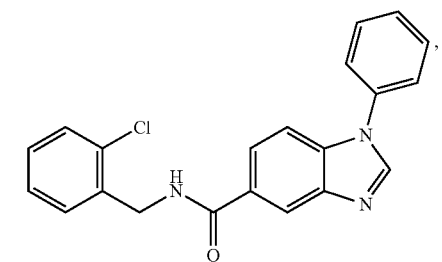
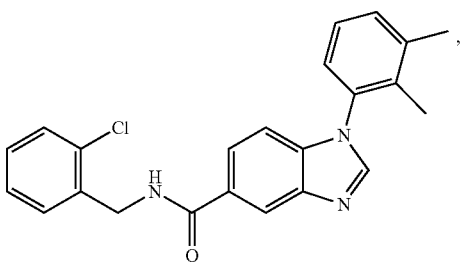
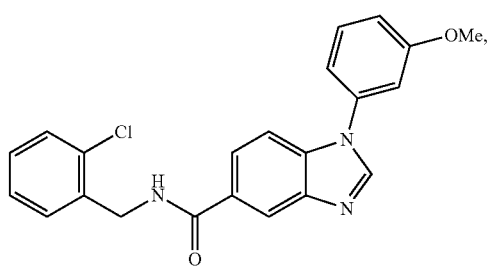
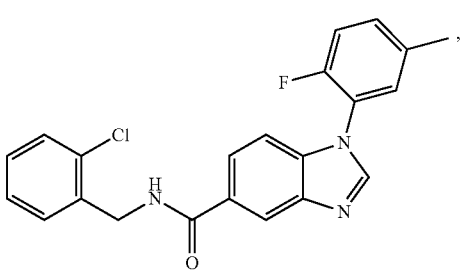
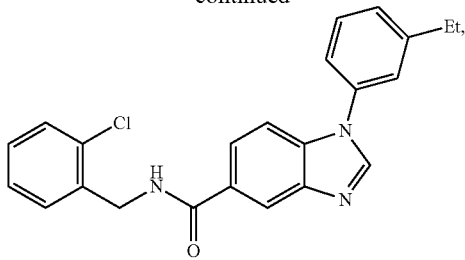
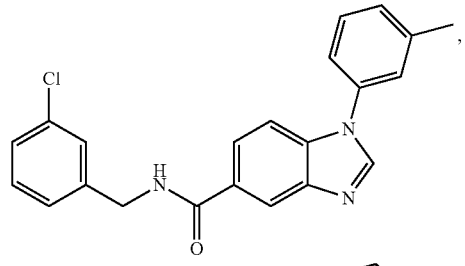
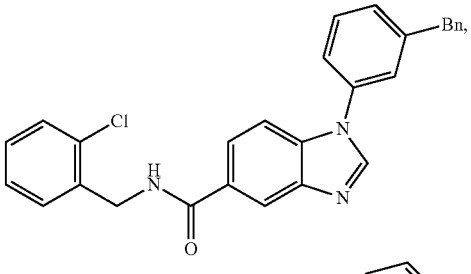
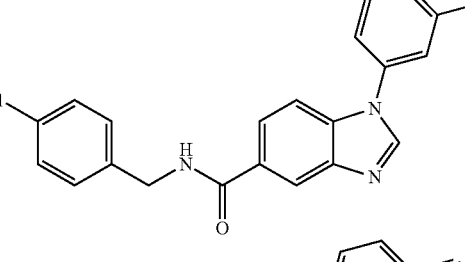
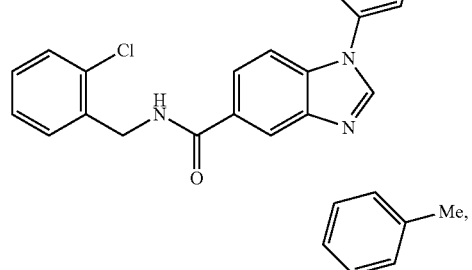
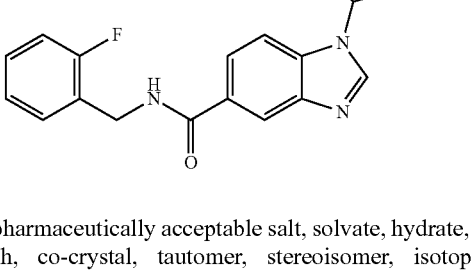
or a pharmaceutically acceptable salt, solvate, hydrate, polymorph, co-crystal, tautomer, stereoisomer, isotopically labeled derivative, or prodrug thereof.
The compounds of the invention may be useful in treating and/or preventing a disease associated with protein aggregation in a subject in need thereof.

Pharmaceutical Compositions, Kits, and Administration

The present invention also provides pharmaceutical compositions comprising a compound described herein, or a pharmaceutically acceptable salt, solvate, hydrate, polymorph, co-crystals, tautomer, stereoisomer, isotopically labeled derivative, or prodrug thereof, and optionally a pharmaceutically acceptable excipient.

In certain embodiments, the compound described herein, or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is a prophylactically effective amount. In certain embodiments, the effective amount is an amount useful for treating and/or preventing a disease associated with protein aggregation in a subject in need thereof. In certain embodiments, the effective amount is an amount useful for reducing and/or preventing protein aggregation in a subject in need thereof. In certain embodiments, the effective amount is an amount useful for modulating E3 ubiquitin ligase in a subject in need thereof.

The effective amount of the compound in the composition may be useful for treating and/or preventing a disease associated with protein aggregation, reducing and/or preventing protein aggregation, and/or modulating E3 ubiquitin ligase as a single agent or in combination with another pharmaceutical agent.

In certain embodiments, the effective amount is an amount useful for preventing and/or treating a disease associated with protein aggregation, reducing and/or preventing protein aggregation, and/or for modulating E3 ubiquitin ligase in a subject in need thereof. An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

Pharmaceutical compositions described herein can be prepared by any method known in the art of pharmacology. In general, such preparatory methods include the steps of bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer P-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (I) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity in preventing and/or treating a disease associated with protein aggregation, in preventing and/or treating a neurodegengerative disease, in preventing and/or treating a disease associated with TDP-43, in reducing and/or preventing protein aggregation, and/or for modulating E3 ubiquitin ligase in a subject in need thereof), bioavailability, reduce and/or modify their metabolism, inhibit their excretion, and/or modify their distribution within the body of a subject. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

Additional pharmaceutical agents include, but are not limited to, anti-proliferative agents (e.g., anti-cancer agents), anti-diabetic agents, anti-inflammatory agents, immunosuppressant agents, antifungal agents, antiprotozoan agents, anti-bacterial agents, anti-viral agents, anti-inflammatory agents, anti-allergic agents, and pain-relieving agents. In certain embodiments, the additional pharmaceutical agent is an E3 ubiquitin ligase modulator. In certain embodiments, the additional pharmaceutical agent is an E3 ubiquitin ligase activitor. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agents are pharmaceutical agents useful for treating and/or preventing Parkinson's disease, such as such as l-dopa, dopa decarboxylase inhibitors (such as carbidopa, levodopa, benserazide, combination preparations of carbidopa/levodopa (e.g., SINEMET, PARCOPA), benserazide/levodopa (e.g., MADOPAR)), carbidopa/levodopa/entacapone (STALEVO), COMT inhibitors (such as entacapone (COMTAN) and tolcapone (TASMAR)), dopamine agonists (such as bromocriptine (PARLODEL), pergolide (PERMA), pramipexole (MIRAPE), rotigotine transdermal (NEUPRO), ropinirole (REQUIP), cabergoline, apomorphine (APOKYN), and lisuride), dopamine agonists, MAO-B inhibitors (such as rasagiline (AZILECT), selegiline (ELDEPRYL, CARBEX, DEPRENYL), benzotropine mesylate (COGENTIN), metabolites of selegiline (L-amphetamine and L-methamphetamine), amantadine (SYMMETREL) and trihexyphenyl (ARTANE)). In certain embodiments, the additional pharmaceutical agents are pharmaceutical agents useful for treating and/or preventing Alzheimer's disease, such as cholinesterase inhibitors (e.g., ARICEPT, rivastigmine (EXELON), galantamine (REMINYL, now RAZADYNE)), NMDA antagonists (such as memantine (NAMENDA) and PDE4 inhibitors such as cilomilast (ARIFLO)), nonsteroidal anti-inflammatory drugs (NSAIDs) (such as R-flurbiprofen (FLURIZAN)), cholesterol-lowering statin drugs (such as pravastatin, simvastatin, and atorvastatin), anti-amyloid and anti-Aβ immune therapy, compounds which inhibit the aggregation of Aβ (such as scylloinositol and clioquinol), compounds which inhibit or modify Aβ production or processing (such as γ-secretase inhibitors, β-secretase inhibitors, γ-secretase modulators, Aβ modulators, and GSK-3 inhibitors), compounds which regulate Aβ turnover (such as PAI-1 inhibitors), compounds which regulate tau phosphorylation (such as GSK-3 and CDK-5 inhibitors), PPARγ agonists (such as rosiglitazone), compounds which regulate tau or phosphor-tau turnover or oligomerization (such as HSP90 inhibitors, HDAC inhibitors and anti-tau immune therapy), compounds which stabilize or bind to microtubules (such as taxane derivatives and epothilone derivatives), and compounds which regulate mitochondria function (such as latrepirdine).

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the first container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the kits described herein are useful for preventing and/or treating a neurodegenerative disease. In certain embodiments, the kits described herein are useful for preventing and/or treating a disease associated with protein aggregation in a subject in need thereof. In certain embodiments, the kits are useful for reducing and/or preventing protein aggregation in a subject in need thereof. In certain embodiments, the kits are useful for preventing and/or treating a disease associated with TDP-43. In certain embodiments, the kits are useful for modulating E3 ubiquitin ligase in a subject in need thereof. In certain embodiments, the kits further include instructions for administering the compound, or a pharmaceutically acceptable salt, solvate, hydrate, polymorph, co-crystal, tautomer, stereoisomer, isotopically labeled derivative, or prodrug, or a pharmaceutical composition thereof. In certain embodiments, the kits and instructions provide for treating and/or preventing a disease associated with protein aggregation in a subject in need thereof. In certain embodiments, the kits and instructions provide for reducing and/or preventing protein aggregation in a subject in need thereof. In certain embodiments, the kits and instructions provide for modulating E3 ubiquitin ligase in a subject in need thereof. The kit of the invention may include one or more additional pharmaceutical agents described herein as a separate composition.

Methods of Treatment and Uses

Protein aggregation is a biological phenomenon in which misfolded proteins aggregate (i.e., accumulate and clump together) either intra- or extracellularly. These protein aggregates are often toxic; protein aggregates have been implicated in a wide variety of disease known as amyloidoses, including Alzheimer's disease, Parkinson's disease, and prion disease.

Protein aggregation can occur due to a variety of causes. Individuals may have mutations that encode for proteins that are particularly sensitive to misfolding and aggregation. Alternatively, disruption of the pathways to refold proteins (chaperones) or to degrade misfolded proteins (the ubiquitin-proteasome pathway) may lead to protein aggregation. As many of the diseases associated with protein aggregation increase in frequency with age, it seems that cells lose the ability to clear misfolded proteins and aggregates over time. It has been suggested that protein aggregation is a second line of the cellular reaction to an imbalanced protein homeostasis rather than a harmful, random process. It has also been found that sequestration of misfolded, aggregation-prone proteins into inclusion sites is an active organized cellular process, that depends on quality control components, such as HSPs and co-chaperones. Moreover, it was shown that eukaryotic cells have the ability to sort misfolded proteins into two quality control compartments: 1. The JUNQ (JUxta Nuclear Quality control compartment). 2. The IPOD (Insoluble Protein Deposit). The partition into two quality control compartments is due to the different handling and processing of the different kinds of misfolded aggregative proteins: the IPOD serves as a sequestration site for non-ubiquitinated terminally aggregated proteins, such as the huntingtin protein. Under stress conditions, such as heat, when the cellular quality control machinery is saturated, ubiquitinated proteins are sorted to the JUNQ compartment, where they are eventually degraded. Thus, protein aggregation may be regulated and/or controlled through means such as ubiquitination.

Ubiquitin is a small regulatory protein that has been found in almost all tissues of eukaryotic organisms. It directs proteins to compartments in the cell, including the proteasome which destroys and recycles proteins. Ubiquitin can be attached to proteins and label them for destruction. Ubiquitin tags can also direct proteins to other locations in the cell, where they control other protein and cell mechanisms.

An E3 ubiquitin ligase is a protein that in combination with an E2 ubiquitin-conjugating enzyme causes the attachment of ubiquitin to a lysine on a target protein via an isopeptide bond (e.g., an amide bond that is not present on the main chain of a protein); an E3 ubiquitin ligase targets specific protein substrates for degradation by the proteasome. The E3 ubiquitin ligase may be involved in ubiquitination, such as polyubiquitination and mono-ubiquitination. In polyubiquitination, a second ubiquitin is attached to the first, a third is attached to the second, and so forth. Polyubiquitination marks proteins for degradation by the proteasome. There are also some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin.

There are nearly 600 ubiquitin ligases encoded by the human genome, and they may be central to a multitude of human diseases involving problems in protein homeostasis (e.g., the regulation of protein aggregation), such as diseases associated with protein aggregation (e.g., amyloidoses). Currently no therapies target the underlying cellular pathologies responsible for the major neurodegenerative diseases, such as Parkinson's disease (PD). Given the complexities of these diseases and the protein homeostasis networks that control them, phenotypic screens offer a powerful alternative to target-based drug discovery. Using this unbiased approach, compounds of Formula (I) (e.g., compound ABI) that strongly and specifically protected yeast and neuronal models from the PD protein, α-synuclein (α-syn) are discovered. Three chemical genetic screens in wild-type yeast cells established that ABI activates the E3 ubiquitin ligase, Rsp5/Nedd4. Network analysis using established genetic and physical interactions illuminated the multifaceted relationships among ABI, Rsp5, and the highly specific cellular perturbations caused by α-syn. Phenotypic screening and chemical genetics in yeast hold promise for breaking early roadblocks in identifying compounds for neurodegenerative diseases and determining their mechanisms of action.

In one aspect, the present invention provides methods of modulating E3 ubiquitin ligase in a subject in need thereof.

In certain embodiments, the methods of the invention include administering to the subject an effective amount of a compound described herein, or a pharmaceutical composition thereof.

In certain embodiments, the subject described herein is a human. In certain embodiments, the subject is an animal.

The animal may be of either sex and may be at any stage of development. In certain embodiments, the subject is a fish. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Without wishing to be bound by any particular theory, the inventive compounds, pharmaceutical compositions, and/or methods may regulate (e.g., activate) the E3 ubiquitin ligase, such as Rsp5/Nedd4. Therefore, the compounds, pharmaceutical compositions, and/or methods of the invention may be useful for modulating (e.g., promoting) ubiquitin-mediated processes controlled by the E3 ligase, such as protein aggregation.

Another aspect of the present invention relates to methods of activating E3 ubiquitin ligase in a subject in need thereof.

In another aspect, the present invention provides methods of treating and/or preventing a disease associated with ubiquitin and/or E3 ubiquitin ligase in a subject in need thereof. Diseases associated with ubiquitin and/or E3 ubiquitin ligase may involve degeneration of neurons in the brain and may be characterized by the presence, in affected neurons, of abnormal filaments that comprise ubiquinated components. In certain embodiments, the diseases associated with ubiquitin and/or E3 ubiquitin ligase that may be treated and/or prevented by the inventive methods include, but are not limited to, AD (including senile dementia of the Alzheimer's type), PD, Pick's disease, progressive supranuclear palsy (PSP), and diffuse Lewy body diseases.

In another aspect, the present invention provides methods of reducing and/or preventing protein aggregation in a subject in need thereof.

Another aspect of the present invention relates to methods of treating and/or preventing a disease associated with protein aggregation in a subject in need thereof. In certain embodiments, the disease that may be treated and/or prevented by the inventive methods is a neurodegenerative disease. In certain embodiments, the disease associated with protein aggregation that may be treated and/or prevented by the inventive methods is an amyloidosis. In certain embodiments, the amyloidosis described herein is Parkinson's disease. In certain embodiments, the amyloidosis described herein is Alzheimer's disease. In certain embodiments, the amyloidosis described herein is a prion disease. In certain embodiments, the prion disease described herein is a transmissible spongiform encephalopathy (TSE), such as Creutzfeldt-Jakob disease (CJD), Gerstmann-Straiussler-Scheinker syndrome (GSS), fatal insomnia (FI), bovine spongiform encephalopathy (BSE), or chronic wasting disease (CWD). Other diseases associated with protein aggregation known in the art are also contemplated as within the scope of the present invention.

Another aspect of the present invention relates to methods of treating and/or preventing a neurodegenerative disease in a subject in need thereof. The pathology of neurodegenerative disease, including polyglutamine diseases, may be characterized by the presence of inclusion bodies in brain tissue of affected patients. In general, these inclusion bodies consist of insoluble, unfolded proteins that are commonly tagged with ubiquitin. Covalent tagging of proteins with chains of ubiquitin generally targets them for degradation. The ubiquitin/proteasome system (UPS) may be the major route through which intracellular proteolysis is regulated. This implicates the UPS in these disease-associated inclusions, either due to malfunction (of specific UPS components) or overload of the system (e.g., due to aggregation of proteins (e.g., unfolded/mutant proteins)), resulting in subsequent cellular toxicity. Protein targeting for degradation is a highly regulated process. It relies on transfer of ubiquitin molecules to the target protein via an enzyme cascade and specific recognition of a substrate protein by E3 ubiquitin ligase. E3 ubiquitin ligase may play a causal role in neurodegenerative disease, e.g., E3 ubiquitin ligase may be responsible for neurodegenerative diseases. Therefore, modulating E3 ubiquitin ligase may be useful for treating and/or preventing neurodegenerative diseases.

In certain embodiments, neurodegenerative diseases that may be treated and/or prevented by the inventive methods include, but are not limited to, Alexander disease, Alper's disease, AD, amyotrophic lateral sclerosis, ataxia telangiectasia, Canavan disease, Cockayne syndrome, corticobasal degeneration, Creutzfeldt-Jakob disease, Huntington disease, Kennedy's disease, Krabbe disease, Lewy body dementia, Machado-Joseph disease, multiple sclerosis, PD, Pelizaeus-Merzbacher disease, Pick's disease, primary lateral sclerosis, Refsum's disease, Sandhoff disease, Schilder's disease, Steele-Richardson-Olszewski disease, tabes dorsalis, and Guillain-Barre Syndrome.

Another aspect of the present invention relates to methods of treating and/or preventing a disease associated with TDP-43 in a subject in need thereof. TDP-43 is a normal cellular protein of 43 kDa that was originally discovered as the cellular protein involved in binding the transactivating region of HIV DNA that contains RNA binding motifs. TDP-43 was found in ubiquitinated cytoplasmic and neuritic inclusions in the neurons from affected regions of patients with diseases such as frontotemporal lobar degeneration (FTLD) and ALS. It has also been found to be present in non-ubiquitinated glial occlusions in one case of familial frontotemporal dementia. The absence of genetic linkage in a Manchester cohort of frontotemporal dementia patients, suggests that protein aggregation may be associated with the disease. TDP-43 has also been found to accumulate in the brains of Guam Parkinson's dementia patients, hippocampal sclerosis, neurodegenerative diseases (e.g., Lewy body diseases, AD, and Pick's disease), and has been proposed for use as a diagnostic for neurodegenerative disorders. A number of mutations have been discovered linking TDP-43 to neurodegenerative diseases. TDP-43 has been shown to be associated with SOD in frontotemporal dementia and ALS. TDP-43 has also been demonstrated to be associated with α-synuclein and tau. The nuclear protein TDP-43 was found to be the neuropathological substrate in non-tau forms of FTLD, ALS, and other neurodegenerative diseases. When TDP-43 is overexpressed, it is toxic to neurons. TDP-43 gene transfer with AAV9 has provided unequivocal examples of cytoplasmic and ubiquinated lesions, apoptosis, micro- and astrogliosis, vector dose-dependent loss of dopaminergic neurons in the substantia nigra and their axons in the striatum, progressive motoric behavior deficit, and expression of TDP-43 in neuronal plasmalemma.

In certain embodiments, the diseases associated with TDP-43 that may be treated and/or prevented by the inventive methods include, but are not limited to, amyotrophic lateral sclerosis (ALS), frontotemporal dementia, FTLD, AD, and hippocampal sclerosis.

Another aspect of the invention relates to methods of screening a library of compounds to identify one or more compounds that are useful in the methods of the invention. In certain embodiments, the one or more compounds identified are useful for treating and/or preventing a disease associated with protein aggregation in a subject in need thereof. In certain embodiments, the one or more compounds identified are useful for reducing and/or preventing protein aggregation in a subject in need thereof. In certain embodiments, the one or more compounds identified are useful for modulating E3 ubiquitin ligase in a subject in need thereof. In certain embodiments, the library of compounds is a library of compounds described herein. In certain embodiments, the methods of screening a library include providing at least two different compounds described herein; and performing at least one assay using the different compounds described herein, to identify one or more compounds that are useful in the inventive methods.

The different compounds described herein may be generated by synthetic methods such as combinatorial chemistry (see, e.g., Ecker et al., Bio/Technology, (1995) 13:351-360 and U.S. Pat. No. 5,571,902). In certain embodiments, the different compounds are provided by liquid-phase or solution synthesis. In certain embodiments, the different compounds are provided by solid-phase synthesis. In certain embodiments, the different compounds are provided by a high-throughput, parallel, or combinatorial synthesis. In certain embodiments, the different compounds are provided by a low-throughput synthesis. In certain embodiments, the different compounds are provided by a one-pot synthesis. The different compounds may be provided robotically or manually. In certain embodiments, the step of providing at least two different compounds of the present invention include arraying into at least two vessels at least two different compounds of the present invention wherein the compounds are bound to solid supports, cleaving the compounds from the solid supports, and dissolving the cleaved compounds in a solvent. The solid supports include, but do not limit to, beads (e.g., resin beads and magnetic beads), hollow fibers, solid fibers, plates, dishes, flasks, meshes, screens, and membranes. In certain embodiments, the solid supports are beads. In certain embodiments, one solid support is capable of supporting at least 50 nmol of a compound. In certain embodiments, one solid support is capable of supporting at least 100 nmol of a compound. In certain embodiments, one solid support is capable of supporting at least 200 nmol of a compound. Each vessel may contain one or more support-bound compounds of the present invention. In certain embodiments, each vessel contains one support-bound compounds of the present invention. The solid supports and/or the compounds may be labeled with one or more labeling agents for the identification or detection of the compounds. The vessels may be wells of a microtiter plate. The solvent may be an inorganic solvent, organic solvent, or a mixture thereof. The steps of arraying, cleaving, and dissolving may be performed robotically or manually.

Typically, the methods of screening a library of compounds involve at least one assay. In certain embodiments, the assay is performed to detect one or more characteristics associated with the treatment and/or prevention of a disease associated with protein aggregation, the reduction and/or prevention of protein aggregation, and/or the modulation of E3 ubiquitin ligase in a subject in need thereof. The assay may be an immunoassay, such as a sandwich-type assay, competitive binding assay, one-step direct test, two-step test, or blot assay. The step of performing at least one assay may be performed robotically or manually.

In another aspect, the present invention provides the compounds and pharmaceutical compositions described herein for use in the treatment and/or prevention of a disease associated with protein aggregation in a subject in need thereof.

In yet another aspect, the present invention provides the compounds and pharmaceutical compositions described herein for use in the reduction and/or prevention of protein aggregation in a subject in need thereof.

In still another aspect, the present invention provides the compounds and pharmaceutical compositions described herein for use in the modulation of E3 ubiquitin ligase in a subject in need thereof.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Preparation of the Compounds

Compounds of Formula (I) may be prepared by the synthetic sequence outlined below in Scheme 1. Alternatively, compounds of Formula (I) may be synthesized by other methods described herein.

Scheme 1. Exemplary synthesis of compounds of Formula (I).

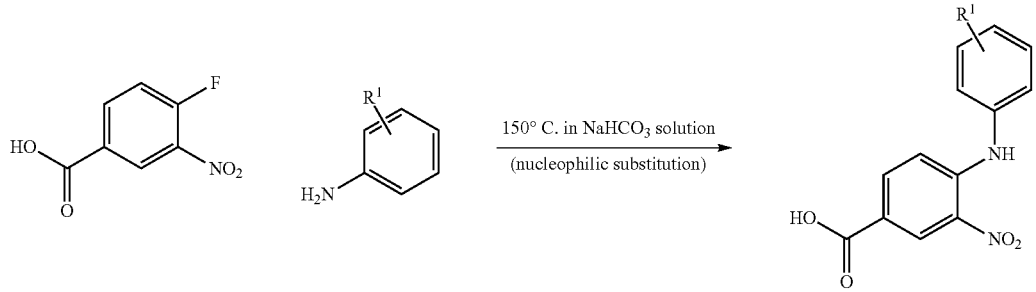

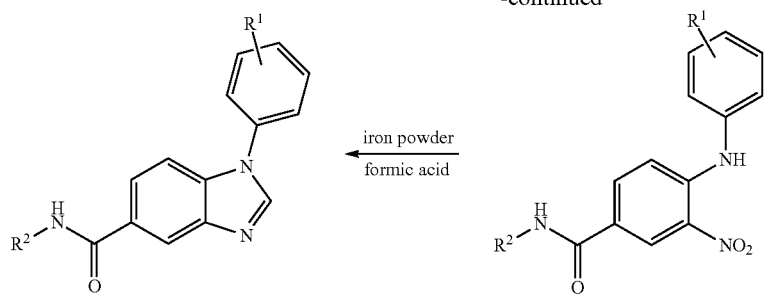
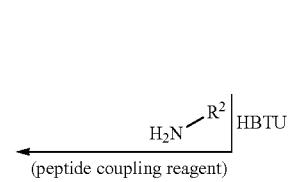

The original screen hit compound, ABI, was purchased from ChemDiv (K783-0286). Subsequent synthesis was performed according to the following strategy.

O-(Benzotriazol-1-yl)-N,N,N',N'-tetramethyluronium hexafluorophosphate (HBTU, 99%) was purchased from Oakwood Products, Inc. and iron powder (99%, 325 mesh) was obtained from Acros Organics. All other starting materials and solvents were purchased from Aldrich Chemical Co. or Alfa Aesar and all reagents were used as received. Compounds were purified by flash chromatography using Silicycle SiliaFlashP60 (230-400 mesh) silica gel. All new compounds were characterized by $^1$H NMR, $^{13}$C NMR, IR Spectroscopy, melting point, and elemental analysis. NMR data were recorded on a Varian XL 500 MHz spectrometer and chemical shifts ($\delta$) are internally referenced to residual portion of solvent. Infrared (IR) spectra were obtained using a Thermo Scientific Nicolet iS5 FT-IR spectrometer equipped with an iD5 ATR Diamond plate. Elemental analyses were carried out by Atlantic Microlabs Inc., Norcross, Ga.

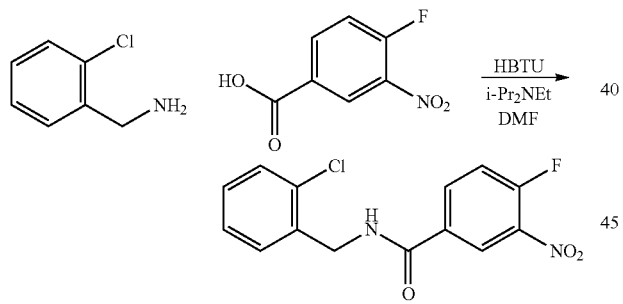

N-(2-chlorobenzyl)-4-fluoro-3-nitrobenzamide

To a stirred solution of 4-fluoro-3-nitrobenzoic acid (925 mg, 5.0 mmol), HBTU (1.90 g, 5.0 mmol), N,N-diisopropylethylamine (1.05 mL, 6.0 mmol), and DMF (10 mL) was slowly added 2-chlorobenzylamine (0.65 mL, 5.5 mmol) at room temperature. After 30 min, the solution was diluted with ethyl acetate (50 mL) and washed sequentially with water, 1M HCl (aq), 1M KOH (aq), and brine. The organic layer was dried (Na$_2$SO$_4$), filtered, and concentrated using a rotary evaporator. Purification of the residue by silica gel chromatography using a Biotage Isolera 4 (silica-packed 25 g SNAP column; 10-45% EtOAC/Hexanes; material loaded using toluene) provided the title compound as a yellow solid (1.26 g, 82% yield), mp 149-150 C. 1H NMR (500 MHz, CDCl$_3$) $\delta$ 8.47 (dd, J=6.9, 2.3 Hz, 1H), 8.10 (ddd, J=8.7, 4.1, 2.3 Hz, 1H), 7.44-7.32 (m, 3H), 7.28-7.22 (m, 2H), 6.94 (t, J=5.8 Hz, 1H), 4.70 (d, J=5.8 Hz, 2H). $^{13}$C NMR (126 MHz, CDCl$_3$) $\delta$ 164.77, 158.98, 156.83, 135.46, 135.25, 135.17, 134.44, 131.79, 131.76, 131.21, 130.41, 130.11, 127.95, 125.73, 125.71, 119.77, 119.60, 43.17 (observed complexity due to carbon-fluorine coupling). IR (neat) 3292, 1640, 1620, 1531, 1347, 1318, 1266, 845, 753, 658 cm$^{-1}$. Anal Calcd. for C$_{14}$H$_{10}$ClFN$_2$O$_3$: C, 54.47; H, 3.27. Found: C, 54.52; H, 3.22.

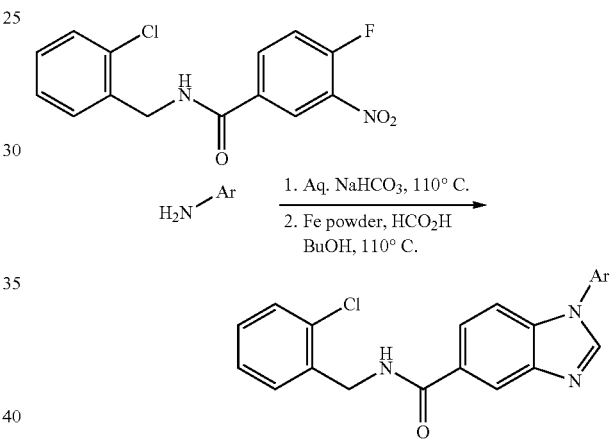

General Procedure for the Conversion of N-(2-chlorobenzyl)-4-fluoro-3-nitrobenzamide to Compounds ABI1, ABI2, ABI3

A screw-top test tube containing N-(2-chlorobenzyl)-4-fluoro-3-nitrobenzamide (100 mg, 0.32 mmol), sodium bicarbonate (54 mg, 0.64 mmol), arylamine (0.64 mmol), and water (0.75 mL) was sealed with a Teflon screw cap, placed in a preheated 110° C. oil bath, and aged at that temperature with stirring for 24 h. Upon cooling to room temperature, the mixture was poured onto ethyl acetate (and any solid dissolved) and the solution washed sequentially with 1M HCl (aq), water, and brine. The organic layer was dried (Na$_2$SO$_4$), filtered, and concentrated using a rotary evaporator. In all cases, complete reaction was observed by TLC (30% EtOAc/Hexanes). The resulting crude nitroaniline was dissolved in n-butanol (2 mL), transferred to a second screw-top test tube and the solution was treated with formic acid (2 mL), iron powder (180 mg, 3.2 mmol), and concentrated HCl (0.40 mL). The test tube was sealed with a Teflon screw cap, again placed into a preheated 110° C. oil bath, and aged with stirring for 1 h. After cooling to room temperature, the mixture was poured onto a mixture of ethyl acetate (25 mL) and saturated sodium bicarbonate (150 mL)

in a separatory funnel. The mixture was shaken with venting (CAUTION: pressure buildup due to release of $CO_2$) and solid sodium bicarbonate added until pH~12. The layers were separated and the organic layer was washed with water, dried and concentrated as before. The residue was purified by silica gel chromatography using a Biotage Isolera 4 (silica-packed 25 g SNAP column; 40-100% EtOAC/Hexanes; material loaded using chloroform) to afford the title compound.

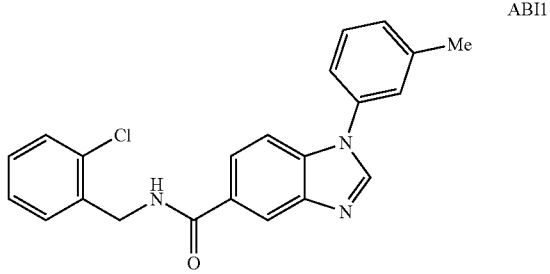 [SMILES: Cc1cccc(-n2cnc3cc(C(=O)NCc4ccccc4Cl)ccc32)c1]

N-(2-chlorobenzyl)-1-(m-tolyl)-1H-benzo[d]imidazole-5-carboxamide (ABI1)

Using m-toluidine (69 µL, 0.64 mmol), the general procedure afforded 117.0 mg (97% yield) of the title compound as a white solid, mp 129-131° C. 1H NMR (500 MHz, CDCl$_3$) δ 8.40 (dd, J=1.7, 0.6 Hz, 1H), 8.01 (s, 1H), 7.92 (dd, J=8.5, 1.7 Hz, 1H), 7.55-7.42 (m, 4H), 7.35 (dd, J=7.6, 2.1 Hz, 1H), 7.32-7.14 (m, 5H), 4.79 (d, J=5.9 Hz, 2H), 2.46 (s, 3H). $^{13}$C NMR (126 MHz, CDCl$_3$) δ 168.41, 144.46, 144.16, 141.14, 136.65, 136.50, 136.40, 134.25, 130.74, 130.64, 130.19, 130.05, 129.92, 129.50, 127.80, 125.28, 124.36, 121.74, 119.97, 111.44, 42.71, 22.16. IR (neat) 3293, 1655, 1500, 1475, 1312, 1244, 781, 747, 692 cm$^{-1}$. Anal Calcd. for $C_{22}H_{18}ClN_3O$: C, 70.30; H, 4.83. Found: C, 70.07; H, 4.90.

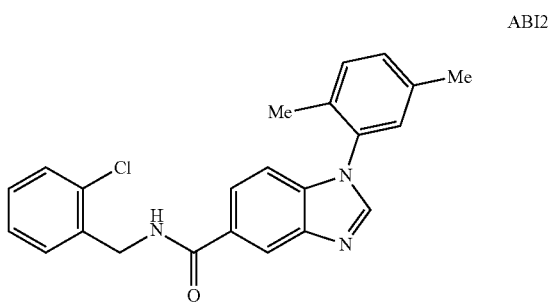 [SMILES: Cc1ccc(C)c(-n2cnc3cc(C(=O)NCc4ccccc4Cl)ccc32)c1]

N-(2-chlorobenzyl)-1-(2,5-dimethylphenyl)-1H-benzo[d]imidazole-5-carboxamide (ABI2)

Using 2,5-dimethylaniline (80 µL, 0.64 mmol), the general procedure afforded 112.7 mg (90% yield) of the title compound as a white solid, mp 141-142° C. 1H NMR (500 MHz, CDCl$_3$) δ 8.47 (d, J=1.5 Hz, 1H), 7.90 (dd, J=8.5, 1.6 Hz, 1H), 7.85 (s, 1H), 7.69 (t, J=5.9 Hz, 1H), 7.47 (dd, J=7.3, 2.1 Hz, 1H), 7.32 (dd, J=7.5, 1.7 Hz, 1H), 7.28 (d, J=7.9 Hz, 1H), 7.26-7.22 (m, 1H), 7.21-7.12 (m, 3H), 7.05 (s, 1H), 4.78 (d, J=5.9 Hz, 2H), 2.38 (s, 3H), 1.97 (s, 3H). $^{13}$C NMR (126 MHz, CDCl$_3$) δ 168.56, 145.15, 143.44, 137.99, 137.51, 136.73, 134.65, 134.16, 132.54, 132.11, 131.12, 130.55, 130.15, 129.89, 129.40, 128.63, 127.76, 124.31, 119.89, 111.46, 42.64, 21.49, 17.80. IR (neat) 3290, 1642, 1614, 1510, 1471, 1309, 1038, 816, 748 cm$^{-1}$. Anal Calcd. for $C_{23}H_{20}ClN_3O$: C, 70.85; H, 5.17. Found: C, 70.34; H, 5.19

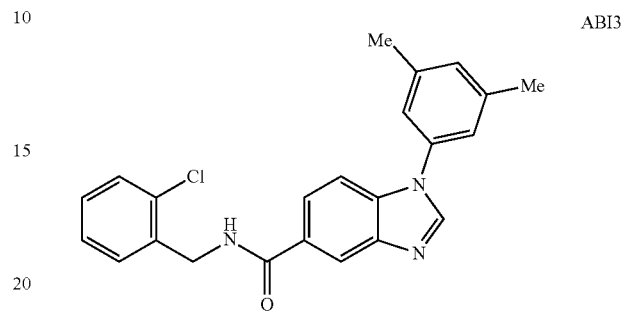

N-(2-chlorobenzyl)-1-(3,5-dimethylphenyl)-1H-benzo[d]imidazole-5-carboxamide (ABI3)

Using 3,5-dimethylaniline (80 µL, 0.64 mmol), the general procedure afforded 95.2 mg (76% yield) of the title compound as a white solid, mp XX-XX ° C. 1H NMR (500 MHz, CDCl$_3$) δ 8.39 (d, J=1.2 Hz, 1H), 8.01 (s, 1H), 7.92 (dd, J=8.6, 1.7 Hz, 1H), 7.54 (dd, J=8.6, 0.7 Hz, 1H), 7.49 (dd, J=7.2, 2.1 Hz, 1H), 7.43 (t, J=6.0 Hz, 1H), 7.36 (dd, J=7.3, 2.0 Hz, 1H), 7.25-7.18 (m, 2H), 7.11 (s, 1H), 7.06 (s, 2H), 4.80 (d, J=5.9 Hz, 2H), 2.42 (s, 6H). $^{13}$C NMR (126 MHz, CDCl$_3$) δ 168.41, 144.54, 144.17, 140.83, 136.66, 136.56, 136.33, 134.27, 130.77, 130.20, 129.97, 129.51, 127.82, 124.26, 122.37, 119.91, 111.53, 42.72, 22.04. IR (neat) 3278, 1642, 1598, 1489, 1308, 1213, 1038, 748, 693 cm$^{-1}$. Anal Calcd. for $C_{23}H_{20}ClN_3O$: C, 70.85; H, 5.17. Found: C, 70.37; H, 5.32.

Example 2. High-Throughput Small Molecule Screen

Taking advantage of the ease of yeast culture and the ability to synchronously induce expression of toxic proteins that strongly inhibit growth, about 190,000 diverse compounds were screened for the restoration of growth in cells expressing the ND-associated protein TDP-43 (6). Compound ABI (FIG. 1A) identified by its modest efficacy against TDP-43 proved to have much greater potency and efficacy against α-syn (FIG. 1B). ABI was not, however, effective against other ND-associated proteins, including htt72Q, FUS/TLS, and the Aβ peptide (FIG. 1B). Thus, rescue was not targeted to a common feature of misfolded protein toxicity, but rather reflected the ability of ABI to target specific pathologies related to α-syn (and to a lesser degree TDP-43).

It was found that ABI reversed several key pathogenic features of α-syn toxicity. First, ABI prevented the accumulation of cytoplasmic α-syn foci, which are pools of stalled vesicles that fail to fuse with destination membranes (FIG. 1C) (7, 8). Second, ABI completely abolished the generation of reactive oxygen species that occurs as part of an α-syn-mediated effect on mitochondrial function (FIG. 1D) (9). Finally, ABI directly ameliorated an ER-Golgi trafficking block and prevented the generation of highly localized nitrosative stress, a newly identified toxic phenotype. The detrimental effects of α-syn are extremely dosage dependent, in yeast and in humans (11, 12), however ABI did not reverse α-syn phenotypes by reducing α-syn levels (FIG. 1E).

Example 3. Chemical Genetic Screens

Overexpression Screen

The overexpression screen was carried out using a pooled FlexGene library (35) transformed into WT yeast compromised for drug efflux. A frozen aliquot of a pooled yeast library was thawed in SGalUra supplemented with 0.05% glucose in 30 mL and grown at 30° C. for ~8 hours. During this time, the culture doubled about between 0.5 and 1 time. Yeast were then diluted to an $OD_{600}$ of 0.0005 in SGalUra, which corresponded to an approximate 20-fold coverage of the diversity of the library, and 40 μM ABI2. After ~3 days of growth, visible colonies growing in the 384 well plates were recovered and validated independently. Plasmids were recovered using a yeast plasmid isolation kit (ZymoResearch), amplified in E. coli, and sequenced. Resulting sequences were then interrogated with BlastN (NCBI) to identify the responsible ORF.

Transposon (Tn7) Screen

The transposon-based deletion screen was performed instead of a traditional haploid deletion screen for technical reasons. The BY4741 host strain for the deletion library was much less sensitive to the compound because of an intact drug efflux system, thereby preventing the use of this screening strategy. Therefore, a different approach was used whereby an in vitro-generated transposon library (Tn7) contains random insertions of a transposon in genomic DNA (not necessarily ORFs) (14). The transposon is marked with a URA3 gene for selection. The pooled Tn7 library was linearized with NotI and transformed into WT yeast with deletions of Δpdr1 and Δpdr3. Yeast were selected on SDUra plates (~200,000 colonies were obtained), pooled, and frozen in aliquots. For the screen, the yeast were thawed and treated essentially as in the over expression screen. Cells were plated at an $OD_{600}$ of 0.005 and grown for ~3 days. ABI2-resistant colonies were confirmed and the transposon sequenced using an established ligation-mediated PCR strategy.

Spontaneous ABI2-Resistant Mutants

The selection of ABI2-resistant mutants was accomplished by dispensing WT yeast in 384 well plates and an $OD_{600}$ of 0.01 and selecting colonies that grew out after 3-4 days. Drug-resistant clones were validated, checked against other toxic compounds, and their genomes sequenced using barcoded, multiplex HiSeq Illumina sequencing. Yeast genomic DNA from 5 mLs of saturated YPD cultures was isolated using four ZymoResearch DNA isolation kits to maximize recovery. 2 μg of DNA was sonicated to ~200-500 bp fragments.

Using an Illumina HiSeq platform, one lanes of 40 base pair single end reads was obtained, resulting in an average coverage of 20-30 fold (all reads will be available at NCBI). After quality control filtering, reads from each sequenced genome were aligned S. cerevisiae reference sequence (sacCer2, June 2008 assembly, downloaded from UCSC on Apr. 1, 2011: hgdownload.cse.ucsc.edu/goldenPath/sacCer2/chromosomes/) using the BWA aligner (39). This was followed by variant calling with respect to this S. cerevisiae reference using the UnifiedGenotyper from the Genome Analysis Toolkit (GATK) (40). To identify variants (including SNPs and indels) unique to a strain, the "parental" strain was compared to individual "derived" strains. A combination of custom code and the GATK's CombineVariants and SelectVariants features was used a to locate, and then to rank by quality, the SNPs and indels detected in open reading frames that were present only in derived strains. Alignments of the reads for the ranked SNPs and indels were then visually inspected to in the Integrative Genomics Viewer (IGV) (41) for quality control. The SNP in Rsp5p (G747E) was visualized using PyMol and PDB (3OLM) (FIG. 3F (16)).

Example 4. General Methods of Biological Assays

Yeast Strains and Culturing

Yeast strains expressing toxic proteins have been described previously (6, 9, 33, 34) (Table 1). All strains have either single or multiple inserts for galactose-inducible expression. In addition, all stains have either deletions of the Δpdr1::KanMX and Δpdr3::KanMX or Δpdr5::KanMX to reduce efflux of compounds and required compound dosing. Yeast were cultured in complete synthetic media (CSM) and an appropriate dropout (minus HIS or URA) to maintain plasmids if required. For galactose-induction experiments, overnight cultures were grown in CSM/2% glucose to saturation and diluted 1:20 into CSM/2% raffinose for ~2 generations. Cultures were then diluted into CSM/2% galactose at an optimum $OD_{600}$ for the experiment (see 'Growth assays').

TABLE 1

Yeast strains.

| Strain | Genotype | Reference |
|---|---|---|
| Y5595 | W303; MATα his3, leu2, trp1, ura3, pdr1::Kan, pdr3::Kan | (9) |
| TDP-43-GFP | Y5595; GAL1-TDP-43-GFP::HIS3 and GAL1-TDP-43-GFP::TRP1 | (6) |
| α-syn-GFP | Y5595; GAL1-α-syn-GFP::TRP1, GAL1-α-syn-GFP::URA3 | (9) |
| htt72Q-CFP | Y5595; GAL1-htt72Q-CFP::HIS3 | (42) |
| Aβ | Y5595; GAL1-Kar2ss-Aβ::TRP1 and GAL1-Kar2ss-Aβ::URA3 loci | (33) |
| FUS | Y5595; GAL1-FUS::HIS3 | (34) |
| NoTox | Y5595; GAL1-α-syn-GFP::URA3, pAG304::TRP1 | (9) |
| InTox | Y5595; pAG304::TRP1, GAL1-α-syn-GFP::HIS3 loci | (9) |
| NoTox | Y5595; GAL1-α-syn::URA3, pAG304::TRP1 | (9) |
| HiTox | Y5595; GAL1-α-syn::TRP1, GAL1-α-syn::URA3 | (9) |
| Δbul1 | Y5595, gene disruption with $Hyg^R$ | |
| Δdoa4 | Y5595, gene disruption with $Hyg^R$ | |
| Δvrp1 | Y5595, gene disruption with $Hyg^R$ | |
| Δp.rsp5 | Y5595, gene disruption with $Hyg^R$ | |
| RSP5 | Y5595, WT RSP5 marked with $Hyg^R$ | |
| rsp5G747E | Y5595, mutation marked with $Hyg^R$ | |
| Δsla1 | Y5595, gene disruption with $Hyg^R$ cassette | |
| Δbul1 α-syn | α-syn-GFP, gene disruption with $Hyg^R$ | |
| Δdoa4 α-syn | α-syn-GFP, gene disruption with $Hyg^R$ | |
| Δvrp1 α-syn | α-syn-GFP, gene disruption with $Hyg^R$ | |
| Δp.rsp5 α-syn | α-syn-GFP, gene disruption with $Hyg^R$ | |
| RSP5 α-syn | α-syn-GFP, WT RSP5 marked with $Hyg^R$ | |
| rsp5G747E α-syn | α-syn-GFP, mutation marked with $Hyg^R$ | |
| Δsla1 α-syn | α-syn-GFP, gene disruption with $Hyg^R$ cassette | |
| BUL1/Δbul1 | MATa/α with Δbul1::HYG | |
| DOA4/Δdoa4 | MATa/α with Δdoa4::HYG | |
| VRP1/Δvrp1 | MATa/α with Δvrp1::HYG | |

TABLE 1-continued

Yeast strains.

| Strain | Genotype | Reference |
| --- | --- | --- |
| RSP5/Δrsp5 | MATa/α with Δrsp5::HYG | |
| SLA1/Δsla | MATa/α with Δsla1::HYG | |

Deletion strains were generated by transforming WT yeast with a PCR fusion product of the HygromycinR cassette and 5' and 3' flanking sequences. In some cases, an ~300 bp 5' PCR fragment and ~300 bp 3' PCR fragment were individually amplified with oligo sequences homologous to the HygromycinR (Hyg$^R$) cassette and used in a second PCR to generate a Hyg$^R$ fragment with ~300 bp of homology on either side. This increase in homology was required because conventional ~40 bp homology was sometimes insufficient to accurately target genetic disruptions to the desired loci. In some cases, PCR products recombined with the KanamycinR cassettes used to delete Δpdr1::KanMX and Δpdr3::KanMX, thus requiring extra homology. These two fragments were then used as primers off of the HygR plasmid. PCR products were purified (Qiagen, MinElute), verified by agarose gel electrophoresis, and transformed into competent yeast using LiOAc-based transformation. Cells were grown in rich media (YPD) for ~4 hrs before plating on YPD/Hygromycin plates. Genetic disruption was confirmed by PCR using oligonucleotides upstream of the deletion and a reverse oligo within the Hyg$^R$ gene. For deletions in the α-syn-expressing yeast, deletions were generated in opposite mating type and mated, sporulated, and dissected to obtain the correct genotypes. Correct markers and mating type were confirmed.

WT or α-syn strains harboring plasmids were constructed by LiOAc transformation of empty vector (e.g., pAG413/416Gal-ccdb) or pAG413/416Gal-ORF. Transformations were plated on synthetic drop-out lacking either histidine or uracil for selection of the plasmid. All subsequent husbandry used appropriate drop-out media.

Plasmids

Plasmid construction for galactose-inducible overexpression experiments was accomplished by transferring ORFs from the FlexGene library (35) to pDONR221 using BP Clonase (Invitrogen) according to manufacturer's specifications. Entry clones were verified by BsrGI restriction digests and, if needed, DNA sequencing. After verification, ORFs were transferred to Gateway-compatible destination vectors (pAG413Gal) using LR Clonse (Invitrogen) according to manufacturer's specifications. Clones were verified by BsrGI restriction digests. Generated plasmids are listed in Table 2.

TABLE 2

Yeast plasmids used for overexpression and Gateway cloning. Expression plasmids were used in either WT or α-syn yeast strains for dosage-sensitivity experiments with ABI2.

| Plasmid | Description | Reference |
| --- | --- | --- |
| pGAL1-BAP2 | FlexGene, GAL1, URA3, CEN | (35) |
| pGAL1-BAP3 | FlexGene, GAL1, URA3, CEN | (35) |
| pGAL1-LEU2 | FlexGene, GAL1, URA3, CEN | (35) |
| pGAL1-MMP1 | FlexGene, GAL1, URA3, CEN | (35) |
| pGAL1-UBP7 | FlexGene, GAL1, URA3, CEN | (35) |
| pGAL1-UBP11 | FlexGene, GAL1, URA3, CEN | (35) |
| pGAL1-BUL1 | FlexGene, GAL1, URA3, CEN | (35) |
| pGAL1-DOA4 | FlexGene, GAL1, URA3, CEN | (35) |
| pGAL1-RSP5 | FlexGene, GAL1, URA3, CEN | (35) |
| pGAL1-VRP1 | FlexGene, GAL1, URA3, CEN | (35) |
| pGAL1-SLA1 | FlexGene, GAL1, URA3, CEN | (35) |
| pENTR-BAP2 | pDONR221, KanR | |
| pENTR-MMP1 | pDONR221, KanR | |
| pENTR-UBP7 | pDONR221, KanR | |
| pENTR-UBP11 | pDONR221, KanR | |
| pENTR-BUL1 | pDONR221, KanR | |
| pENTR-DOA4 | pDONR221, KanR | |
| pENTR-RSP5 | pDONR221, KanR | |
| pENTR-VRP1 | pDONR221, KanR | |
| pENTR-SLA1 | pDONR221, KanR | |
| pAG413-BAP2 | pAG413, GAL1, HIS3, CEN (AmpR) | |
| pENTR-MMP1 | pAG413, GAL1, HIS3, CEN (AmpR) | |
| pENTR-UBP7 | pAG413, GAL1, HIS3, CEN (AmpR) | |
| pENTR-UBP11 | pAG413, GAL1, HIS3, CEN (AmpR) | |
| pENTR-BUL1 | pAG413, GAL1, HIS3, CEN (AmpR) | |
| pENTR-DOA4 | pAG413, GAL1, HIS3, CEN (AmpR) | |
| pENTR-RSP5 | pAG413, GAL1, HIS3, CEN (AmpR) | |
| pENTR-VRP1 | pAG413, GAL1, HIS3, CEN (AmpR) | |
| MORF-BAP2 | GAL1-BAP2-HIS-HA-ZZ | (43) |

Yeast Growth Assays

Starting cultures for all dose-response assays were established as described above. All growth assays were carried out in 384 well-format. Source plates were assembled in 96 well plates using multichannel pipettes to dilute rows in 1.6-fold serial dilutions of CSMGal. To these dilution series containing 2× final concentration of compound, 2×OD$_{600}$ culture (in CSMGal) was dispensed with a multichannel pipette to achieve a final drug/culture mix with the desired OD$_{600}$ and drug concentration. For wild type yeast, the final starting OD$_{600}$ was 0.01. For α-syn, the final starting OD$_{600}$ was 0.02. Drug concentration ranges varied depending on efficacy, growth inhibition, and solubility in media. A Tecan EvoFreedom liquid handling robot was then used to transfer culture from 96 to 384 well format with each well being represented four times. Final well volume was 35 μL. Plates were then incubated in humidified containers at 30° C. for either 24 or 40 hours. Plates were then read with a Tecan Saphire plate reader at OD$_{600}$.

Raw OD$_{600}$ values were transformed to "Relative Growth" in WT cells or "% Maximum Rescue" in α-syn experiments. In WT cells, the well background was subtracted and all values were then normalized to 100% for the untreated condition. In α-syn rescue experiments, the well background was subtracted and the maximum rescue in the particular experiment was normalized to 100%. All experimental data points were then calculated by (OD$_{600Exp}$−OD$_{600untreated}$/(OD$_{600Max}$−OD$_{600untreated}$)×100 to obtain rescue relative to maximum rescue observed. For deletion strains, data were normalized to the WT α-syn strain harboring no deletions. Dose-response curves were generated by nonlinear regression analysis using Prism Graphpad v. 6.0. In cases where ABI began inhibiting growth, only points up to the maximum were used to fit the curve. Above that, points were directly connected and are always presented as dotted lines.

Survivorship assays were carried out by inducing α-syn expression with 2% galactose overnight for 16 hours from log phase CSM/2% raffinose cultures. After induction, total cell number was counted and 200 cells plated on YPD solid agar plates. After 2 days, surviving colonies were counted using an Acolyte automatic colony counting instrument. Significance was determined using a one-way ANOVA and Tukey's test of significance.

Analysis of α-Synuclein

Microscopy.

Logarithmic growing raffinose cultures were induced with galactose for five hours in the presence or absence of the indication concentration of ABI. Cells were centrifuged, media discarded, and then fixed with 4% paraformaldehyde in 1×PBS for 1 hr. The fixed culture was centrifuged, and the pellet resuspended in 0.4% paraformaldehyde in 1×PBS and kept at 4° C. Single plain images were taken at 100× magnification with a Nikon Eclipse Ti microscope.

ROS.

The generation of reactive oxygen species (ROS) detected from yeast expressing untagged α-syn using the ROS sensing dye, CM-$H_2$DCFDA (Invitrogen), as previously described (9). Briefly, log phase raffinose cultures of α-syn (non-GFP tagged) were induced with galactose with or without ABI1 for 6 hours. At this time, the dye was added for an additional 30 minutes. Cells were then analyzed using an EasyCyte flow cytometer (Guava Technologies).

Western Blot.

Protein analysis of α-syn-GFP was performed in NoTox, InTox, and HiTox strains with ABI1 treatment at indicated concentrations. Log phase CSM/2% raffinose cultures were induced with 2% galactose for 5 hours with DMSO or ABI1. Cultures were normalized to cell density and cell pellets prepared for SDS-PAGE. Cell pellets were boiled in SDS-loading dye for 15', centrifuged, and resolved by 4-12% SDS-PAGE. After transfer, PVDF membranes were blotted for α-syn using the antibody (BD Transduction Laboratories, Cat. No. 610786) at 1:2,000 and an IRDye800 secondary antibody at 1:5,000 (Li-Cor Odyssey, Rockland Immunochemicals). From the same gel, total protein was detected by coomassie staining. Both blots and coomassie-stained gels were scanned using the Li-Cor Odyssey imaging system and quantitated. Values were expressed as α-syn normalized to total protein (FIG. 1E). Significance was determined using a one-way ANOVA with Tukey's test of significance.

CPY western blots were performed using culture conditions as described above. An anti-Cpy antibody (Invitrogen, A6428) was used at 1:5,000. Post-ER:ER ratios were quantitated using an IRDye800 secondary antibody (Li-Cor Odyssey, Rockland Immunochemicals) and scanned with the Li-Cor Odyssey imaging system. Significance was determined using a one-way ANOVA and Tukey's test of significance.

C. elegans Model of α-Syn Toxicity

Drug treatments of the C. elegans α-syn model were performed as previously described (6). Briefly, age-synchronized worms were obtained by treating gravid adults with 2% sodium hyopchlorite and 0.5M NaOH to isolate embryos (36). Variable concentrations of ABI1 or 0.2% DMSO was applied to embryos suspended in M9 buffer (22 mM KH2PO4, 22 mM Na2HPO4, 85 mM NaCl, 1 mM MgSO4) (time 0), and incubated at 25 C for 24 hours to obtain a synchronized L1 population. Worms were washed three times in distilled water and one additional rinse in M9 buffer. The synchronized L1 worms were plated on regular nematode growth media (NGM) plates seeded with 100 uL of Eschericia coli (OP50). Worms were then transferred every other day to new plates to insure food abundance and eliminate progeny contamination. Worms were then analyzed seven days post-hatching. Analyses were carried out according to the criteria previously described (37). In each case, ~30-40 animals were scored for the percent of WT animals. Experiments were completed in triplicate and averages calculated. A one-way ANOVA and Tukey's test was used to determine significance.

Primary Neuronal Cultures of α-Syn Toxicity

Experiments aimed at monitoring dopaminergic cell viability in primary mesencephalic cultures were performed as described previously (7-9). Briefly, cells obtained from the midbrains of E17 rat embryos were plated at a density of $2.18 \times 10^3$ cells per $mm^2$ on a 48-well plate. Four days after plating, the cells were treated with cytosine arabinofuranoside (20 μM) to restrict the growth of glial cells. Three days later (7 days in vitro), the cells were transduced with an adenovirus encoding A53T α-syn, generated using the Invitrogen ViraPower Adenoviral Expression System (38), at a multiplicity of infection (MOI) of 15 in the absence or presence of ABI1 (0.1 μM). After a 72-h transduction period, the media was replaced with fresh media with or without ABI1 for an additional 24 h. The cells were stained for microtubule associated protein 2 (MAP2), a general neuronal marker, and tyrosine hydroxylase (TH), a marker of dopaminergic neurons (7-9). MAP2- and TH-immunoreactive neurons were counted by an investigator blinded to the identity of the treatment conditions in at least ten randomly chosen observation fields (encompassing ~800-1600 $MAP2^+$ neurons) per treatment using a Nikon TE2000-U inverted fluorescence microscope with a 20× objective. Relative dopaminergic cell viability was calculated as the percentage of MAP2-positive neurons that were also TH-positive and normalized by the value determined for control cells (set to 100%). Each experiment was repeated four times using embryonic cultures isolated from independent pregnant rats. For neurite analysis, primary midbrain cultures were plated on coverslips and treated and stained as described above. Neurite length measurements were carried out on approximately 80 neurites from 30-35 neurons in each sample using NIS-Elements software (Nikon). Statistical analyses were conducted using the program GraphPad Prism, version 6.0 (www.graphpad.com/prism/Prism.htm).

Network Analysis.

ABI Network.

The ABI network (FIG. 3E) was generated based on interactions from String 9.0 (string-db.org) and manual literature curation of genetic, functional, or physical interactions not reported in String.

Constructing ABI: α-Syn Network.

The core ABI network was established as described extensively in the paper and depicted in FIG. 3. The α-syn network consisted of 110 genes known to modulate α-syn toxicity in the absence of stressors. 77 of these were established in a reported over-expression screen (8, 21). 33 additional modifiers from 10 other publications were added. (Table 3). An interaction network was generated by collating all genetic and physical interactions cataloged in Biogrid (thebiogrid.org), and visualizing in Cytoscape software. Self-interactions were excluded. Only nodes demonstrating at least one connection with the core ABI network were depicted.

Figure 4C:
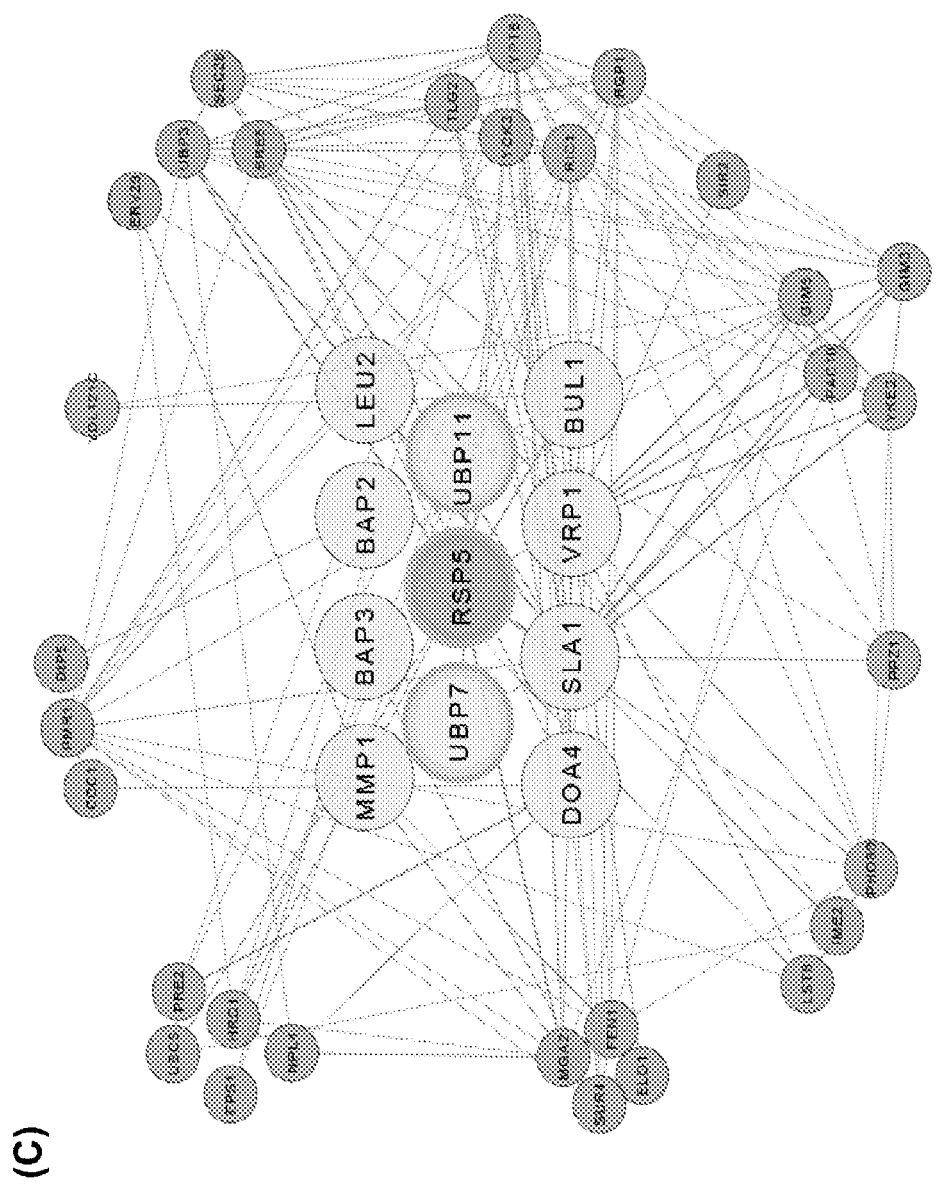
FIG. 4 shows that ABI2 targets Rsp5p activity to rescue α-syn toxicity. (A) ABI2 ($\log_2$, μM) dose-response curves showing % maximum response of α-syn strains overexpressing pUBP7 or pUBP11. (B) ABI2 dose-response curves in α-syn strains deleted for Δbul1 or Δsla1, or expressing the $rsp5_{G747E}$ mutation. (C) Interaction network of α-syn and ABI2 genetic modifiers. α-syn nodes are blue; ABI2 nodes are red, and nodes shared by α-syn and ABI2 networks are red/pink with blue outline. Edges between nodes depict physical or genetic interactions (Biogrid). Thicker lines indicate both genetic and physical interactions. Red edges link to members of the core ABI network. All other edges are blue. (D) Percent survivorship of WT α-syn and $rsp5_{G747E}$ strains after 16 hours of α-syn expression. ****: $P<0.0001$ using a Student's t-test. (E) Western blot of endogenous Cpy in α-syn-expressing strains treated with DMSO or ABI2. Both immature ER and processed post-ER forms are indicated. Accumulation of ER form indicates a block in ER-to-Golgi trafficking. *: $P<0.05$. (F) α-syn-GFP localization in WT α-syn cells with DMSO (left) or ABI2 (middle), and α-syn cells with an $rsp5_{G747E}$ treated with ABI2. Inlaid values indicate % of cells with large α-syn foci with standard deviation. (G) Model depicting direct or indirect activation of Rsp5p to antagonize α-syn toxicity by modulating aspects of vesicular trafficking.

TABLE 3

α-syn interaction network genes for genetic modifiers of α-syn toxicity in addition to those described by reported overexpression screen (8, 21). Only genes shown to affect α-syn toxicity itself, were used for network analysis (FIG. 4C).

| α-syn modifier | Reference |
| --- | --- |
| RSP5 | (22) |
| ATG11, ATG32, SIR2 | (44) |
| ELO1, ELO2, ELO3 | (45) |

TABLE 3-continued

α-syn interaction network genes for genetic modifiers of
α-syn toxicity in addition to those described by reported
overexpression screen (8, 21). Only genes shown to affect α-syn
toxicity itself, were used for network analysis (FIG. 4C).

| α-syn modifier | Reference |
|---|---|
| YCK1, YCK2 | (46) |
| FAS1 | (47) |
| GIM1, GIM2, GIM3, GIM4, ALF1, RBL2 | (48) |
| SEN3, DOA3 | (49) |
| SSA3, YCA1 | (50) |
| RIC1, RGP1, YPT6, TLG2, VPS51, VPS53, VPS54 | (51) |
| NPL4, PRE1, PRE2, SEN3, UBC5 | (10) |

Example 5. ABI Protects Neurons Against α-Syn Toxicity

ABI was tested in nematodes that express both α-syn and GFP in dopaminergic (DA) neurons (9). This model permits the direct visualization of PD-relevant neurons and their age-dependent degeneration in a living animal. Although concentration differences in drugging nematodes (which have a thick cuticle) preclude direct comparison to efficacy in cells, the C. elegans model has proven highly predictive in the characterization of efficacious genetic and chemical modifiers of NDs in mammalian systems (13). In these animals, ABI afforded a partial, yet highly significant, rescue of DA neurons from α-syn toxicity, supporting a conserved MOA (FIGS. 2A and 2B).

Figure 2C:
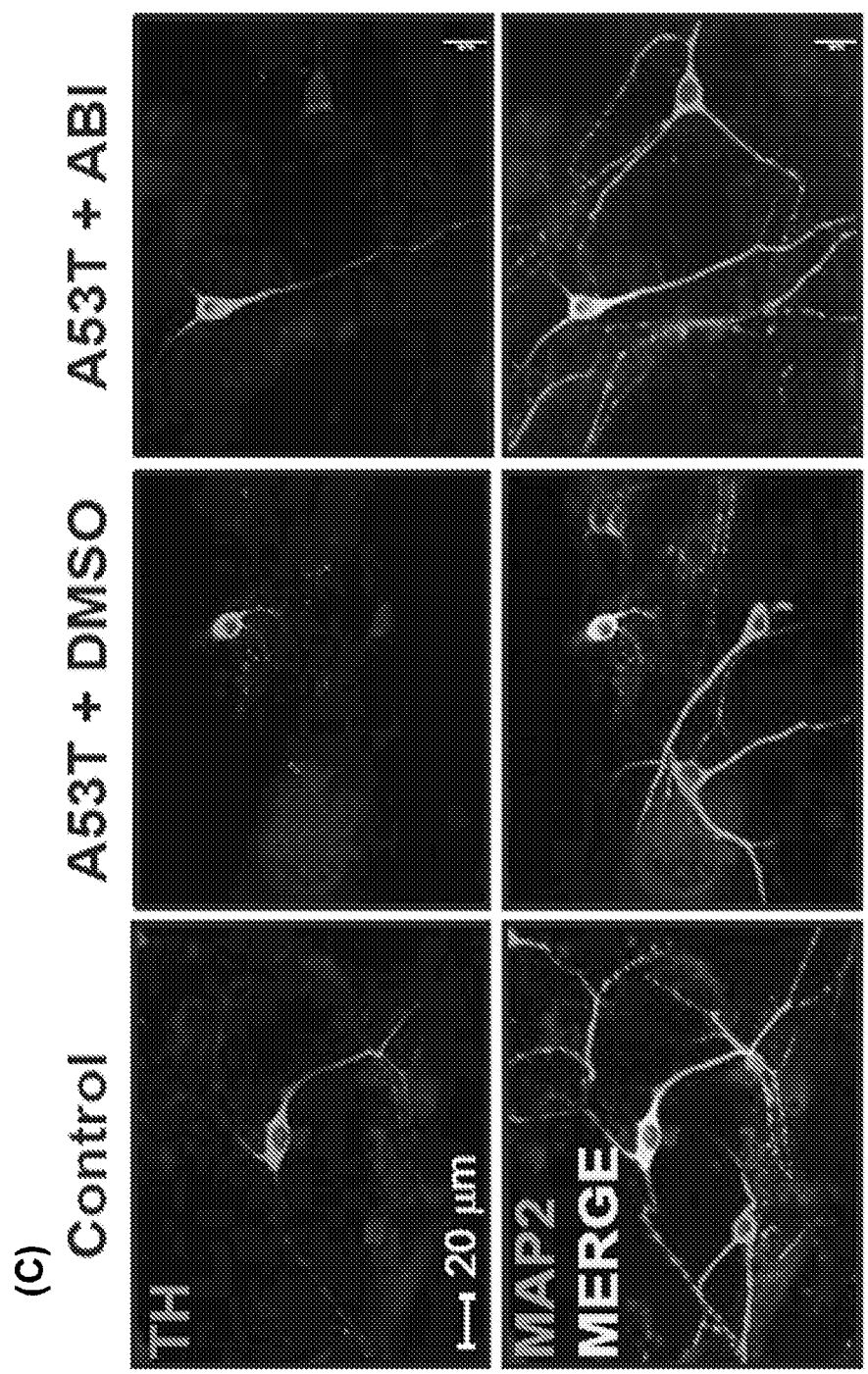
FIG. 2 shows that ABI protects neurons against α-syn toxicity. (A) Fluorescence microscopy of representative C. elegans expressing human α-syn and GFP in the six anterior DA neurons after treatment with DMSO (top) or ABI (bottom). Arrows indicate DA neurons. (B) Quantitation of (A) reported as % of worms with the WT number of DA neurons. (C) Representative images of ventral mesencephalic cultures established from embryonic rat midbrains. The cultures were untransduced ('con') or transduced with A53T α-syn virus in the absence or presence of 0.1 μM ABI. (Top) Tyrosine hydroxylase (TH)-positive neurons (Green or grey). (Bottom) Merge (white) with MAP2 (neuronal tubulin that marks all neurons; red or grey). (D) Percent of TH-positive neurons relative to MAP2 positive neurons (with the control set to 100%). (E) Quantitation of neurite length. Error bars are SEM. In all panels, *: $P<0.05$; : $P<0.01$; *: $P<0.001$, according to one-way ANOVA and a Tukey's test.

ABI was also tested in neurons of mammalian origin. Primary ventral mesencephalic cultures from embryonic rat midbrains were established, which are enriched in DA neurons that are particularly susceptible to α-syn toxicity in humans. Transduction with an adenovirus expressing a familial α-syn mutation (A53T) decreased the percentage of total neurons that express tyrosine-hydroxylase (TH, a marker of DA neurons (9)). ABI largely restored the survival of these neurons (FIGS. 2C, 2D, and 5). ABI also markedly reduced the retraction of neuronal processes caused by A53T α-syn (FIGS. 2C, 2E, and 5). Adenovirus encoding for bacterial lacZ had no effect on either DA neuron loss or neurite length (data not shown).

ABI was also tested in human cortical neurons (which are also affected in PD and related dementias) that were generated from induced pluripotent stem cells (iPSCs) from a patient carrying α-syn mutations. ABI both ameliorated an ER-to-Golgi protein trafficking defect and reduced nitrosative stress in these neurons.

Example 6. Chemical Genetic Screens of ABI2 Reveal a Network Centered on the E3 Ligase, Rsp5p The ability of ABI to ameliorate α-syn toxicity in cell types from yeast to human neurons establishes that its MOA is highly conserved across evolution. The underline mechanism was investigated by taking advantage of three different genome-wide genetic approaches in yeast (5). Typically, altering the levels of a compound's target, or the levels of proteins intimately related to its target pathway, may change the dosage required to produce the compound's phenotype. It is found that ABI inhibited growth at concentrations about four-fold higher than its $EC_{50}$ in rescuing α-syn toxicity (FIG. 3A). At this concentration, the compound also inhibited the growth of wild-type cells (FIG. 3A). Since screening for restored growth facilitates chemical genetic screening, it was investigated whether growth inhibition at high concentrations was related to α-syn rescue at lower concentrations.

50 derivatives of ABI (ABI1 being the parent compound) were generated. It was investigated whether those that altered their activity against α-syn altered their ability to slow the growth of wild-type (WT) cells in a commensurate way. Indeed, this was the case (FIG. 3B). For example, adding a single methyl group at the ortho position (ABI2) or at the meta position (ABI3) of the imidazole linked phenyl group shifted both the efficacy against α-syn, and the ability to inhibit growth to lower (ABI2) or to higher (ABI3) concentrations (FIGS. 3B and 6). Importantly, even at the highest growth-inhibitory doses, cells retained 100% viability (FIG. 3C).

Figure 3D:
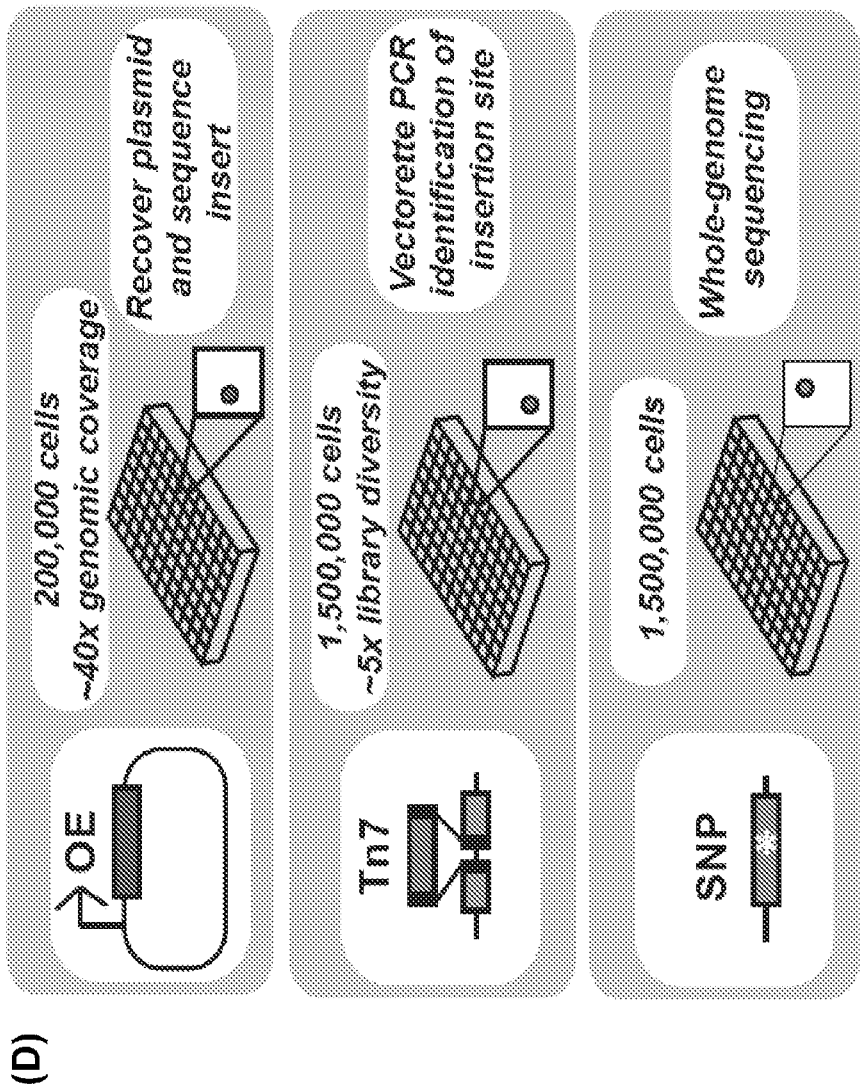
FIG. 3 shows that chemical genetic screens of ABI2 reveal a network centered on the E3 ligase, Rsp5p. (A) Dose-response curves of ABI1 ($\log_2$, μM) in WT (red or squares: relative to no ABI) or α-syn (black or circles: relative to maximum ABI rescue) yeast strains. (B) $EC_{50}$ in α-syn (y-axis) versus $IC_{50}$ in WT (-axis). Additional methyl groups (red or arrows) are shown on imidazole-linked phenyl rings of ABI2 and ABI3. (C) Viable colony forming units (Y-axis) recovered from a single well after prolonged treatment (days) with growth inhibitory concentrations of ABI2. (D) Schematics of overexpression (green or top pane), transposon deletion (blue or middle pane) and spontaneous mutation (red or bottom pane) screens. Selection conditions and 'hit' identification methods are noted. (E) Network of ABI2 modifiers. Nodes are color coded with three different shadings according to the screen of origin in (D): black-, grey-, and white-shaded nodes are according to the bottom pane, top pane, and middle pane in (D), respectively. Edges are interactions based on String database and literature curation: solid lines, genetic/functional interactions; long dashed lines, physical interactions; short dashed lines, both genetic and physical interactions. (F-H) Massively parallel DNA sequencing of ABI2-resistant mutants identify (F) RSP5, (G) BUL1, and (H) DOA4. Gray bars are individual sequencing reads (Illumina) viewed with IGV v. 2.2. Colored vertical lines in the bottom panels denote SNPs. Nucleotide and amino acid substitutions are indicated below sequencing panels. In (F), Rsp5p structure (PDB 3OLM (16)) highlights the active site cysteine (yellow, C777) and G747E (red). In (G) and (H), protein sequences with relevant proximal features are shown. (I) ABI2 ($\log_2$, μM) dose-response curves showing relative growth of heterozygous deletion (+/−) or WT diploid (+/+) strains. (J) ABI2 dose-response curve of cells with either increased (galactose-inducible plasmid, denoted by "p") or decreased expression (Δbul1 or Δp.rsp5 hypomorphic allele where an insertion 500 bp upstream of the promoter reduces expression by ~80% (32)) of Rsp5p or Bul1p.

Growth inhibition in WT cells facilitated three independent chemical genetic selections to explore the MOA of ABI in a genome-wide manner. In each case, genetic alterations were searched for that restored growth at a fully inhibitory concentration of ABI2. First, a galactose-inducible library of single-copy plasmids was used that covered 90% of the yeast genome, screening a sufficient number of transformants to achieve 40× coverage of the genome (FIG. 3D, green or top pane). Second, a library of random transposon insertions was screened in a haploid strain, which allows recovery of knock out insertions and regulatory insertions that alter gene expression (14). A sufficient number of integrants was used for 5× genome coverage (FIG. 3D, blue or middle pane). Finally, genomic mutations arising spontaneously in the absence of mutagenesis were recovered (FIG. 3D, red or bottom pane).

Colonies carrying suppressors were isolated, and the identity of the suppressing gene were determined. For the overexpression screen, the plasmid was isolated and sequenced. For the Tn7 screen, a ligation-mediated vectorette PCR (14) was used to identify the insertion site. And, for the spontaneous ABI2-resistant mutants, multiplexed whole-genome sequencing and SNP-calling algorithms were used to identify the responsible mutations. Finally, it was confirmed that these alterations conferred resistance to ABI on their own by re-constructing them in WT cells.

Figure 3E:
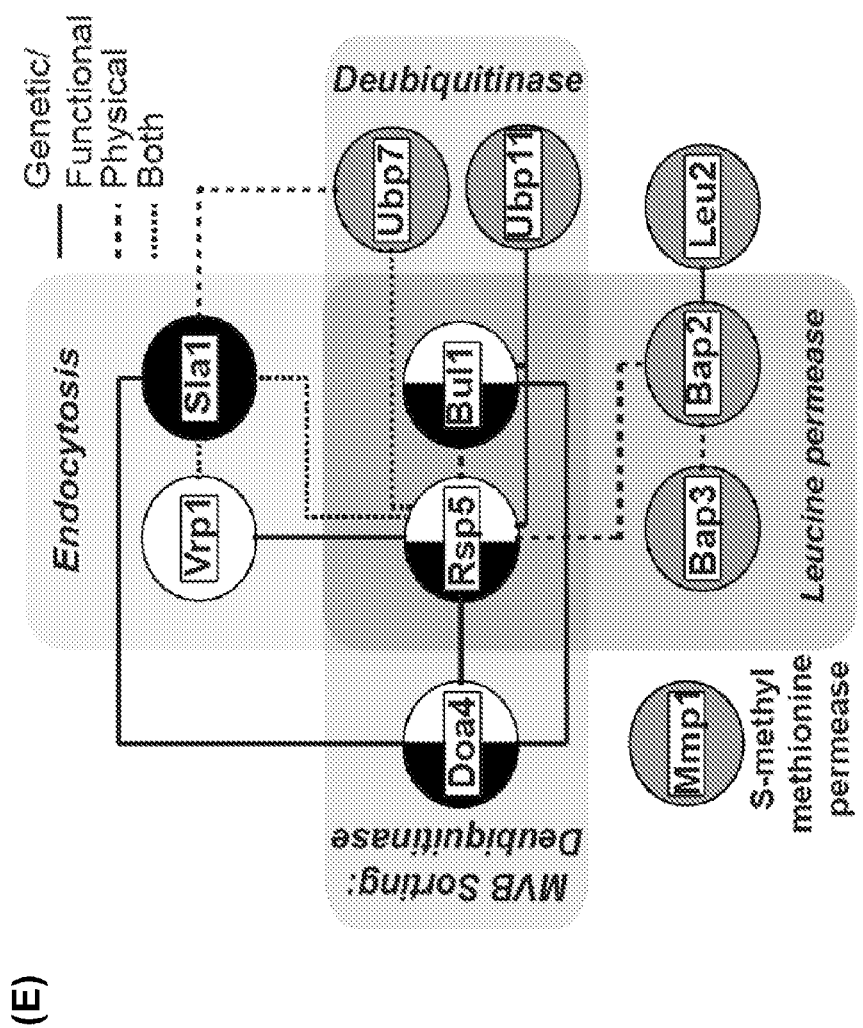
Figure 8:
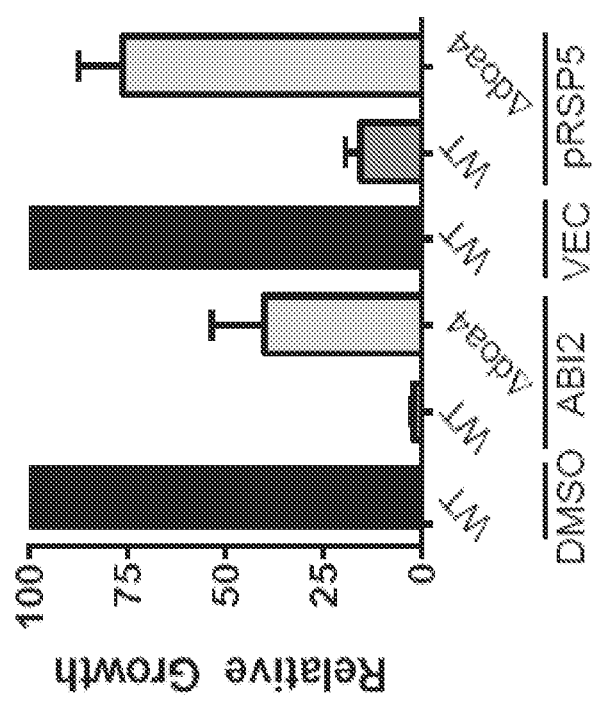
FIG. 8 shows that RSP5 overexpression inhibits growth of WT cells and is suppressed by Δdoa4. WT or Δdoa4 cells with either an empty vector or plasmid encoding RSP5 under the control of the GAL1 promoter were analyzed after 40 hours of induction in 384 well plates. RSP5 overexpression suppressed growth by ~80% and this was largely rescued by Δdoa4. Treatment of Δdoa4 with ABI2 is shown for comparison. Data are normalized relative to untreated or vector controls for ABI2 and RSP5, respectively.

Remarkably, all three screens recovered only a small number of genes and each of these pointed to the same MOA: ABI promotes ubiquitin-mediated processes controlled by the E3 ligase, Rsp5/Nedd4 (FIGS. 3E and 7). Rsp5p is the single yeast member of the mammalian Nedd4 E3 ligase family and has many conserved cellular functions related to endocytic and endosomal trafficking (15). The conservation includes the HECT ubiquitin ligase domain that, in contrast to RING ubiquitin ligases, forms a direct thioester linkage with ubiquitin. Conservation also extends over multiple WW domains that participate in diverse protein-protein interactions with both substrates and adaptor proteins, including the functionally conserved α-arrestins. The genetic alterations are color-coded (FIG. 3E) to correspond to the screen from which they were derived (FIG. 3D). The mutations in RSP5 and BUL1 should reduce Rsp5p activity directly, while the mutations in DOA4, SLA1 and VRP1 and the overexpression plasmids for UBP7 and UBP11 should reduce Rsp5 activity indirectly. The rescuing hits in BAP2/3, MMP1, and LEU2 should ameliorate the consequences of excessive Rsp5p activation. If, as suggested by all of these alterations, growth inhibition at high concentrations of ABI is due to over-activation of Rsp5p, then Rsp5p overexpression should itself reduce the growth of WT cells. Indeed, this was the case (FIG. 8).

The three spontaneous single amino-acid substitutions in RSP5, BUL1, and DOA4 that conferred resistance to ABI are each located proximal to key functional sites. The rsp5$_{G747E}$ mutation is close to the ligase's active site, at a point between the N- and C-terminal lobes of the HECT domain (FIG. 3F, (16)). The bul1$_{Q146P}$ mutation resides ten residues from the PPxY motif that binds the WW domain of Rsp5p, likely compromising binding to Rsp5p (FIG. 3G). Finally, the doa4$_{C579F}$ mutation is eight amino acids from the active site cysteine in the protease domain of Doa4p, and is likely to compromise its activity (FIG. 3H).

Investigating the relationship between the leucine permease BAP2 and ABI2, it was found that ABI2 reduced Bap2p levels in an Rsp5p-dependent manner (FIG. 9) (17). This decrease in Bap2p sensitized cells to low leucine levels as did a Δbap2 deletion (FIG. 9). Conversely, the rsp5$_{G747E}$ point mutation, which mitigated growth inhibition by ABI2, stabilized Bap2p and allowed cells to grow in low leucine (FIG. 9).

Finally, the nature of the genetic variants recovered in enzymes that remove ubiquitin from protein substrates (Ubp7p, Ubp11p, and Doa4p), in combination with established genetic and physical interactions, support the hypothesis that ABI exerts its effect on growth by activating Rsp5p. For example, overexpressing Ubp7p rescued ABI2 growth inhibition and Ubp7p interacts with Rsp5p and antagonize the ubiquitination of cargo destined for the vacuole (yeast equivalent of lysosome) (18). For DOA4, deleting it limits ubiquitin availability and stabilizes Rsp5p substrates (19, 20). This effect of deleting Δdoa4 directly antagonized the slow growth phenotype caused by Rsp5p overexpression (FIG. 8).

The central role of Rsp5p in the ABI2 network was confirmed by its dosage relationship to ABI growth inhibition. Of the five genes that conferred resistance to ABI2, only RSP5 and its adapter protein BUL1 became more resistant to ABI2 when a single copy of the genes encoding them was deleted from diploid cells (FIG. 3I). In contrast, increasing their levels enhanced growth inhibition by ABI2 (FIG. 3J). This bidirectional effect on dosage-sensitivity is a hallmark of drug targets in chemical genetic screens (5).

Example 7. ABI2 Targets Rsp5p Activity to Rescue α-Syn Toxicity

Having used growth inhibition in WT cells as a surrogate for ABI activity, it is investigated how this ABI2 genetic network affected ability of ABI2 to rescue α-syn. Overexpressing UBP7 and UBP11 antagonized α-syn rescue, indicating that the de-ubiquitination of substrates is important in ameliorating α-syn toxicity (FIGS. 4A and 10). Similarly, the rsp5$_{G747E}$ and Δsla1 mutations antagonized α-syn rescue (FIGS. 4B and 10). The effect of Δbul1 was marginal, separating the effects of ABI2 on growth inhibition from its activities in ameliorating α-syn toxicity.

Figure 11A:
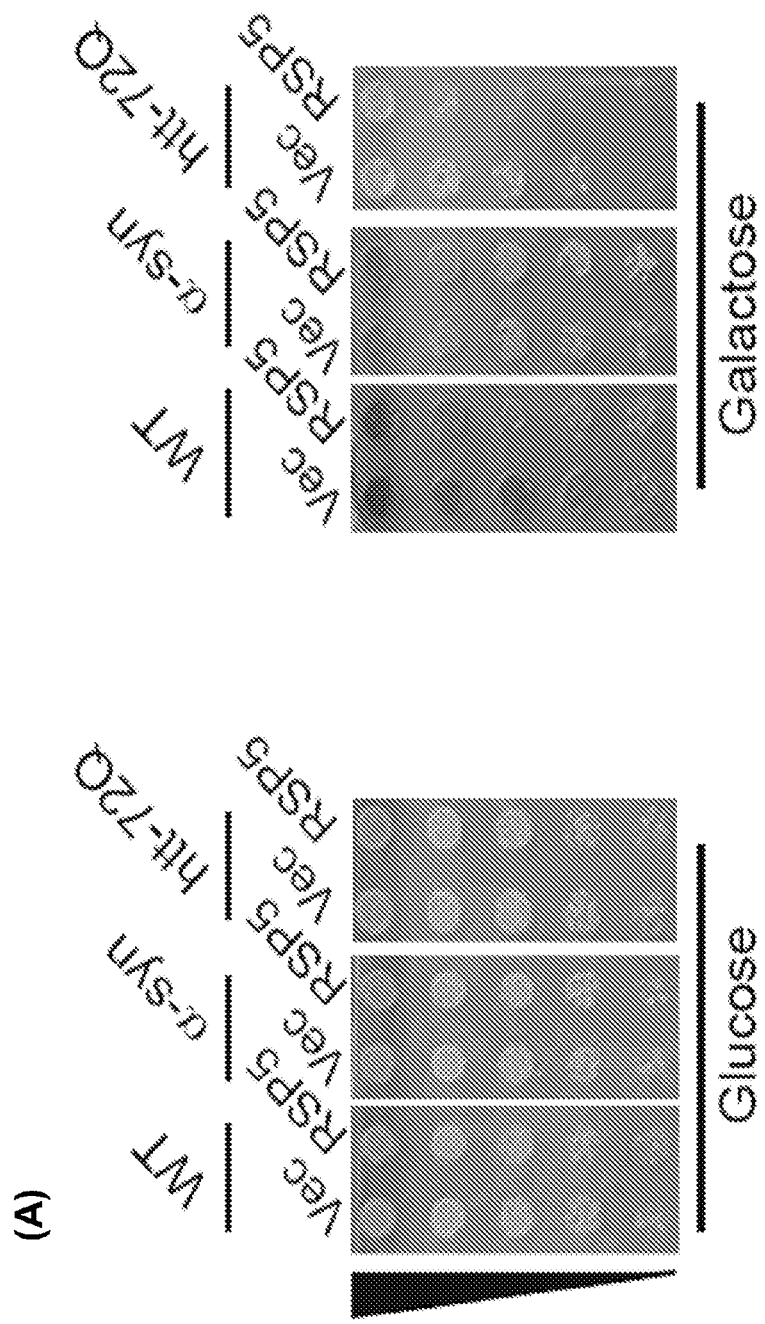
FIG. 11 shows the effects of shared ABI: α-syn network genes on α-syn toxicity. (A) RSP5 overexpression rescued α-syn toxicity. RSP5 overexpression in liquid media inhibits growth. However, on plates where expression levels are lower, RSP5 overexpression rescues α-syn toxicity. Htt72Q, which is not rescued by ABI, is shown for comparison. Plates are 3-fold serial dilutions spotted onto either glucose (left) or galactose (right)-containing plates and grown for 3 days. (B) Dose-response curves for ABI2 (μM) in WT strains deleted for or overexpression pUBP7 or pUBP11. Y-axis is relative growth to untreated condition. (C) Dose-response curves for ABI2 (μM) in α-syn expressing strains with deletions of Δubp7 and Δubp11. Y-axis is % maximum response relative to ABI2 in the WT α-syn strain.

To provide a more global view, the well-documented list of α-syn genetic modifiers in yeast ((8, 21) and Table 3) were integrated with the extensive repository of physical- and genetic-interactions available in this organism. Remarkably, nearly 30% of previously identified α-syn genetic modifiers—functioning in Golgi/vesicular transport, endosomal transport, lipid metabolism, protein catabolism, and tubulin assembly—were directly linked to genes within the ABI network (FIG. 4C). Three nodes Rsp5p, Ubp7p, and Ubp11p were shared between the two network modules. (Notably, UBP7 is the single genetic modifier in common between the α-syn and TDP-43 models, likely explaining why ABI was initially recovered as a modest modifier of TDP-43 (pers. comm. A. Gitler). For each of the shared nodes, the effects of ABI on growth and α-syn toxicity were in opposite directions: Rsp5p overexpression suppressed α-syn toxicity (22) (FIG. S7) and enhanced ABI2 growth inhibition (FIG. 3J); Ubp7p/Ubp11p enhanced α-syn toxicity (21) and suppressed the growth phenotype of ABI2 (FIGS. 3E and 11). Thus, ABI2 acts at a molecular juncture that directly antagonizes the biological effects of α-syn toxicity.

Of the three protein nodes shared by the two networks, only Rsp5p showed a bi-directional dosage sensitivity to ABI2 (FIG. 3J). To rigorously investigate the relationship between Rsp5p and α-syn toxicity, isogenic cells were examined that differed only by the single amino acid substitution in rsp5$_{G747E}$. Remarkably, this substitution, which conferred resistance to ABI in WT cells, enhanced the toxicity of α-syn in the absence of ABI2 (FIG. 4D).

To confirm that the rescuing activity of ABI against α-syn toxicity depended on Rsp5p, ABI's ability to restore ER-to-Golgi trafficking of a representative cargo (Cpy) and to reduce the formation of α-syn foci was tested. ABI2 rescued these phenotypes in WT cells (FIG. 1C, (10)). Moreover, both rescuing activities were compromised in cells that carried the rsp5$_{G747E}$ mutation (FIGS. 4E and 4F). Thus, a single amino acid substitution in the 809 amino acid Rsp5p protein both conferred ABI resistance in WT cells and enhanced toxicity in α-syn-expressing cells. This establishes a pivotal role for Rsp5p in the complex network of α-syn toxicity and, further, establishes that this node can be targeted by a small molecule identified in an unbiased phenotypic screen.

Whether ABI works directly or indirectly on Rsp5p, its net effect is to activate this ubiquitin ligase (FIG. 4G). Rsp5p can ubiquitinate α-syn (22), but the experiments did not detect changes in α-syn levels (FIG. 1E). ABI also did not enhance ubiquitination of recombinant Rsp5p or Nedd4 in vitro (pers. comm. B. Schulman and A. Goldberg). Rather, ABI directly antagonized α-syn-induced pathologies, and it affected the very same biological pathways in cells that did not express α-syn. In living cells, Rsp5p operates within a biologically complex network that creates an extreme challenge for in vitro, reductionist target-based assays. Rsp5p enlists diverse adaptor proteins to ubiquitinate diverse substrates. These activities are regulated by $Ca^{++}$-dependent lipid binding (23, 24) and by diverse post-translational modifications on Rsp5p itself and its partner proteins. Moreover, Rsp5p functions in endocytic and endosomal trafficking, as well as in retrograde Golgi-ER trafficking (25) and ERAD (26). Given this complexity, compounds that regulate Rsp5p activities seem more likely to emerge with phenotypic approaches that place the protein in its normal cellular context. Importantly, this target space is highly relevant to human synucleinopathies, as vesicle trafficking is perturbed by alterations in α-syn and other disease-related genes, including VPS35, LRRK2, and PARK16/RAB7L1 (8, 27-30). The interface between these pathways and the ABI network (FIG. 4C) suggests that the efficacy of ABI against α-syn derives from its power to affect multiple Rsp5p activities.

Figure 12A:
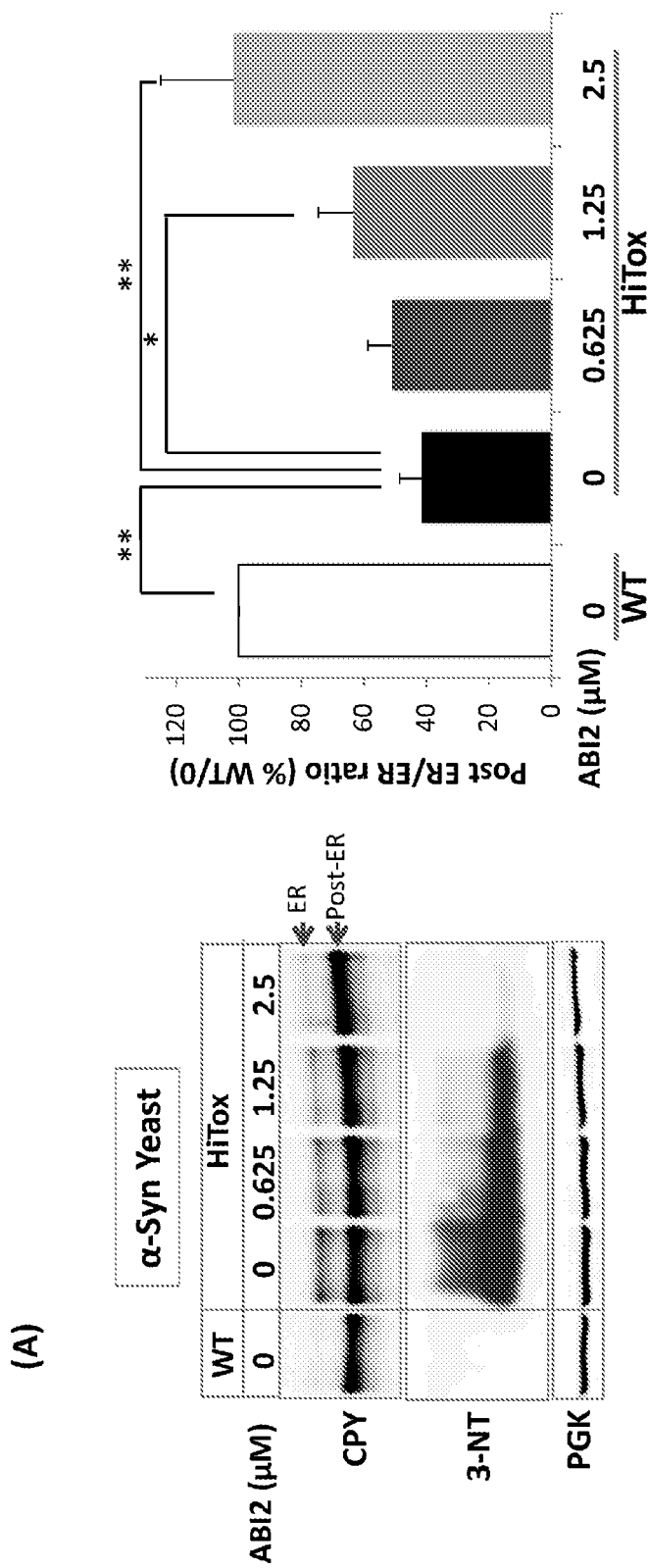
FIG. 12 shows that compound ABI2 corrects analogous defects in yeast and human iPS cellular synucleinopathy models. (A) ABI2 improves forward protein trafficking through the ER and reduces nitrosative stress in the yeast synucleinopathy model. ER vs. post ER (vacuole) form of CPY protein was compared to assess the trafficking from ER (n=3). Nitrosative stress was monitored by protein nitration levels using the 3-NT antibody. (B) ABI2 improves forward protein trafficking through the ER in aSyn$^{A53T}$ iPS neurons. Cells were treated with 20 μM ABI2 for 7-10 days between 8-12 weeks of neuronal differentiation. Trafficking from ER was assessed by probing for nicastrin and GCase with or without Endo H treatment. Data are normalized using corrected/A53T ratios established in FIG. 6 to more faithfully depict the biological significance of the small molecule effects (n=3). (C) ABI2 decreases nitrosative stress in aSyn$^{A53T}$ iPS neurons. A53T or mutation-corrected neural precursors were transduced with lentivirus encoding RFP under the synapsin promoter. Upon differentiation, neurons were labeled with RFP. At 8-12 weeks of differentiation, neurons were treated with 5 μM ABI2 for 7-10 days, loaded with FL2 and live-imaged with the NO sensor FL2 (C; a representative experiment showing quantitation from 18-54 neurons for each condition, the same result was obtained in another independent experiment). All data represented as mean±SEM (*: p<0.05; **: p<0.01, two tail t-test compared to control condition).

Example 8. Compound ABI2 Rescues Defects—Both Trafficking and Nitrosative Stress—in Neurons Derived from Human Parkinson's Disease (PD) Patients ABI2, a small molecule identified in a previous unbiased yeast screen, improves forward protein trafficking through the ER and reduces nitrosative stress in the yeast synucleinopathy model (FIG. 12A).

Figure 12B:
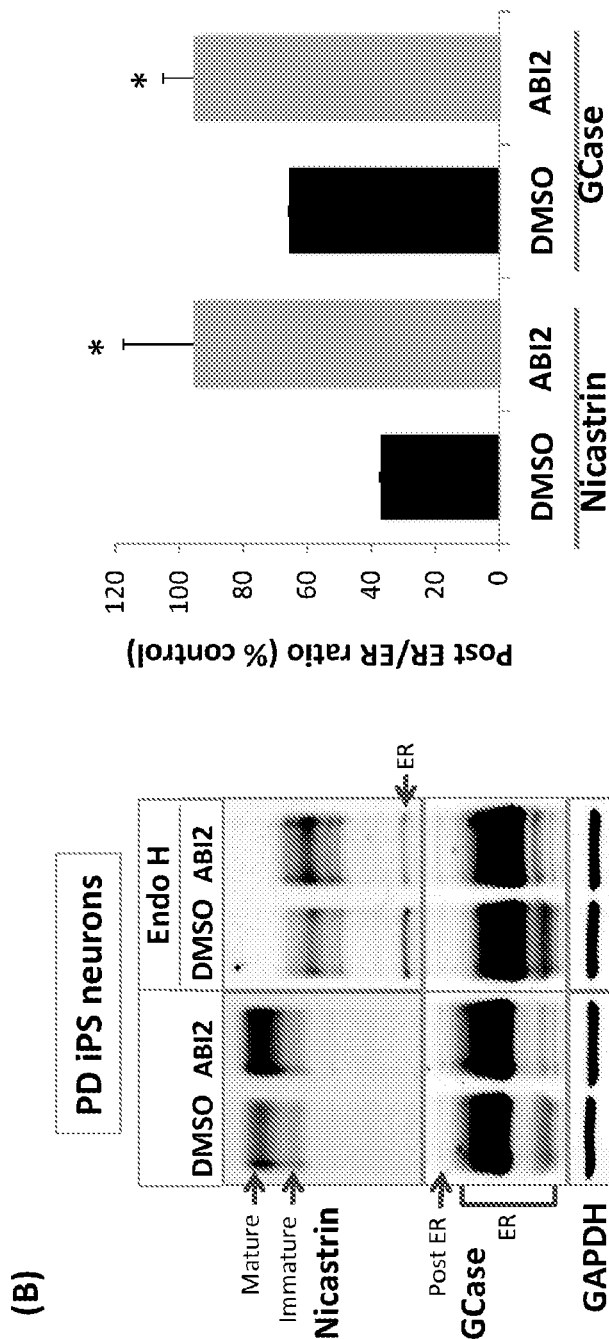

Cells were treated with 20 μM ABI2 for 7-10 days between 8-12 weeks of neuronal differentiation. Trafficking from ER was assessed by probing for nicastrin and GCase with or without Endo H treatment. The results, shown in FIG. 12B, demonstrate that ABI2 improves forward protein trafficking through the ER in aSyn$^{A53T}$ iPS neurons.

Figure 12C:
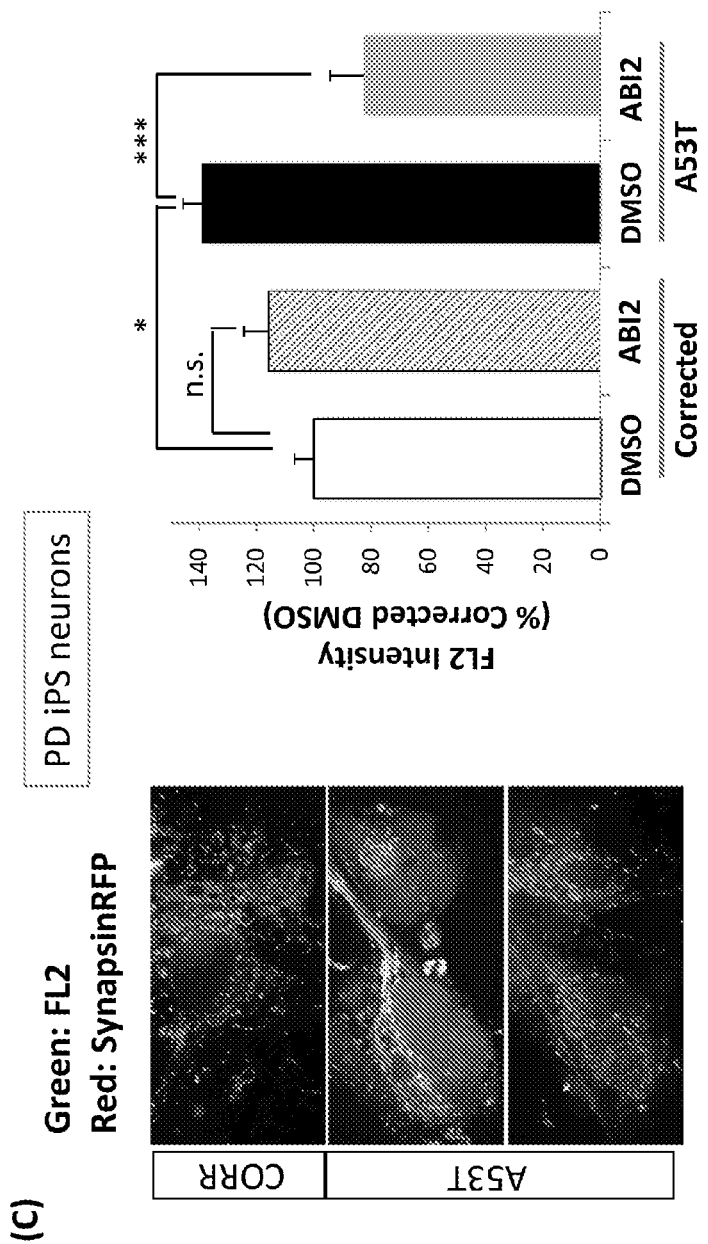

A53T or mutation-corrected neural precursors were transduced with lentivirus encoding RFP under the synapsin promoter. Upon differentiation, neurons were labeled with RFP. At 8-12 weeks of differentiation, neurons were treated with 5 μM ABI2 for 7-10 days, loaded with FL2 and live-imaged with the NO sensor FL2 (a representative experiment showing quantitation from 18-54 neurons for each condition, the same result was obtained in another independent experiment). The results, shown in FIG. 12C, demonstrate that ABI2 decreases nitrosative stress in aSyn$^{A53T}$ iPS neurons.

Example 9: Chemical Genetic Screens of ABI2 Reveal a Network Centered on the E3 Ligase, Rsp5

Yeast screens can reveal the target space for small molecules that suppress growth by identifying genetic alterations that restore it (A. M. Smith, R. Ammar, C. Nislow, G. Giaever, A survey of yeast genomic assays for drug and target discovery Pharmacol Ther 127, 156 (August, 2010)). At concentrations higher than those that rescued α-syn toxicity, compounds described herein (e.g., compound ABI2) inhibited the growth of WT cells. Compounds inactive in rescuing α-syn did not reverse α-syn foci formation or rescue ER-to-Golgi trafficking. Compounds that potently rescued α-syn, also more potently inhibited growth in wild type cells (FIG. 13A). Though ABI inhibited growth, cells retained full viability (FIG. 13B).

Genetic alterations that allowed growth at high concentrations were determined using compound ABI2. Three approaches were used: (1) a library of over-expression strains covering most genes in the yeast genome (about 5,800 genes), (2) a library of about 300,000 random transposon-insertions (A. Kumar, Multipurpose transposon insertion libraries for large-scale analysis of gene function in yeast Methods Mol Biol 416, 117 (2008)), and (3) spontaneous genomic point mutations arising from about 2 million cells. A small number of hits were recovered and formed a highly connected network of functionally related genes (FIG. 13C). These were an E3 ubiquitin ligase that promotes endosomal transport (RSP5), endocytic proteins (SLA1, VRP1), a multivesicular body sorting deubiquitinase (DOA4), an Rsp5 adaptor (BUL1), two proteins that can deubiquitinate Rsp5 substrates (UBP7, UBP11), known and potential Rsp5 substrates (BAP2, BAP3, MMP1) and VPS23, which directs Rsp5 substrates for degradation in the vacuole (FIG. 13C). Analogs ineffective against α-syn did not exhibit dosage sensitivity with ABI network genes, thus supporting a related MOA between α-syn rescue and growth inhibition of wild type cells.

The network topology of screen hits, and the nature of their altered dosage-sensitivity to ABI2, suggested that ABI2 acts on Rsp5 to promote ubiquitin-mediated endosomal transport. With the exception of RSP5, which is essential, every other gene in the network described herein could be deleted. But no deletion (including a double deletion of UBP7 and UBP11) conferred more than partial resistance to ABI2. Thus, while these other proteins are involved in ABI2 activity, they cannot themselves be its target. Indeed, the effects of altering RSP5 gene dosage indicate it is the central node: increased RSP5 dosage increased sensitivity to ABI2 and decreased RSP5 dosage decreased sensitivity to ABI2 (FIG. 13D). Furthermore, in otherwise isogenic cells, a single amino acid substitution in the about 1000 amino acid protein (rsp5$_{G747E}$) conferred resistance to ABI2 (FIG. 13D). Rsp5 is the single yeast member of the highly conserved mammalian family of HECT domain Nedd4 E3 ligases. These proteins catalyze K63 linkages of ubiquitin to diverse membrane proteins and thereby regulate endosomal trafficking, not proteasomal degradation (D. Rotin, S. Kumar, Physiological functions of the HECT family of ubiquitin ligases Nat Rev Mol Cell Biol 10, 398 (June, 2009); E. Lauwers, Z. Erpapazoglou, R. Haguenauer-Tsapis, B. Andre, The ubiquitin code of yeast permease trafficking Trends Cell Biol 20, 196 (April, 2010)). HECT domain ubiquitin ligases contain multiple protein-protein interaction domains that bind diverse adaptor proteins and substrates. Calcium, lipid binding, and autoinhibitory conformations regulate substrate specificity and endosomal transport from either the plasma membrane or Golgi to the vacuole/lysosome. Most aspects of these complex modes of Rsp5 regulation have not been recapitulated in vitro.

Figure 13E:
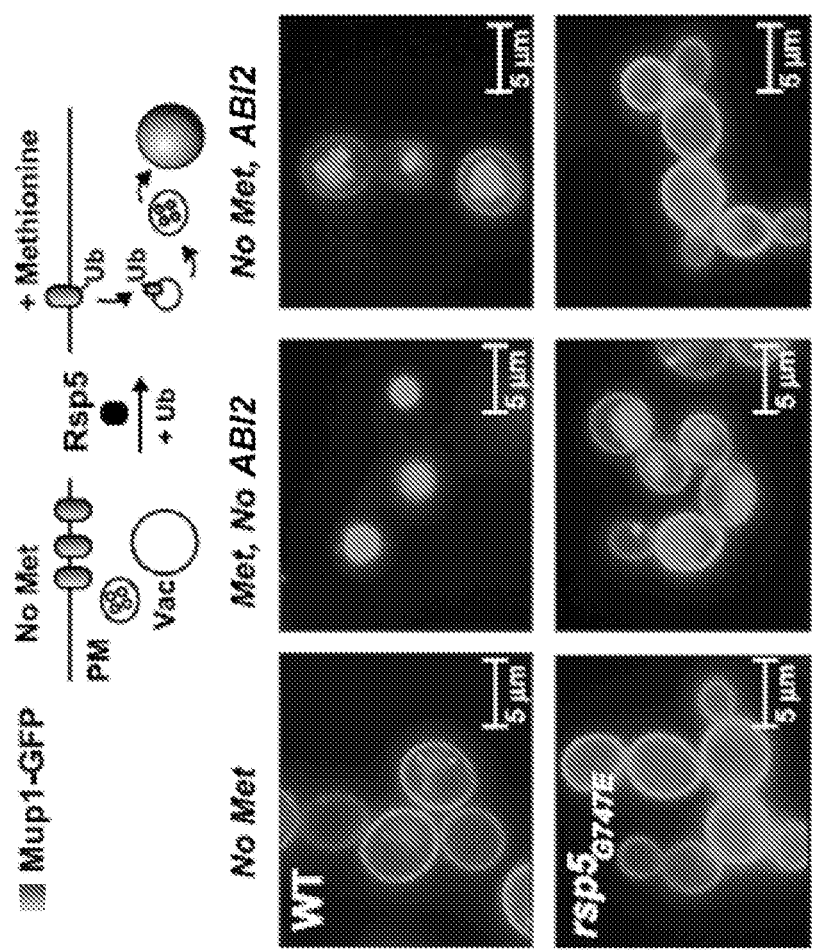
FIG. 13 shows that chemical genetic screens of ABI2 reveal a network centered on the E3 ligase, Rsp5. R: red; G: green; B: blue; Y: yellow. (A) Efficacy (EC$_{40}$) in α-syn cells versus growth inhibition (IC$_{40}$) in WT cells for compounds ABI1 and ABI2. (B) Viable cells recovered after prolonged treatment with ABI2. (C) ABI2 interaction network. Node color reflects screen of origin indicated below. Edges are interactions (see legend, top right) according to String database and literature. VPS23 was deleted after identification of other hits. (D) Heat map of RSP5 variant cell growth in response to increasing ABI2 concentration compared to untreated cells. Mutants include $rsp5_{G747E}$ and the hypomorphic allele, Δp.rsp5. (E) (Top) Methionine- and Rsp5-dependent Mup1-GFP endocytosis; (Bottom) Mup1-GFP localization in wild type and $rsp5_{G747E}$ strains under indicated conditions. (F) (Left) Schematic of Sna3-GFP endosomal trafficking to the vacuole, where GFP is cleaved; (Right) Immunoblot analysis of Sna3-GFP in WT and $rsp5_{G747E}$ cells treated with ABI2.
Figure 13F:

Therefore, to further investigate ABI2 activities, ABI2's effects, in WT cells, on three proteins whose trafficking depends on Rsp5 were monitored: Mup1 (A. Menant, R. Barbey, D. Thomas, Substrate-mediated remodeling of methionine transport by multiple ubiquitin-dependent mechanisms in yeast cells EMBO J 25, 4436 (Oct. 4, 2006)), Sna3 (C. MacDonald, D. K. Stringer, R. C. Piper, Sna3 is an Rsp5 adaptor protein that relies on ubiquitination for its MVB sorting Traffic 13, 586 (April, 2012)) and Bap2 (F. Omura, Y. Kodama, T. Ashikari, The basal turnover of yeast branched-chain amino acid permease Bap2p requires its C-terminal tail FEMS Microbiol Lett 194, 207 (Jan. 15, 2001)). ABI2: (1) promoted the Rsp5-dependent endocytosis and vacuolar delivery of the methionine permease, Mup1 (FIG. 13E); (2) promoted the Rsp5-dependent Golgi-to-vacuole trafficking of the adaptor protein, Sna3 (FIG. 13F); and (3) promoted the Rsp5-dependent degradation of the leucine permease, Bap2. This affected leucine-dependent growth explaining its recovery in the overexpression screen.

Figure 14A:
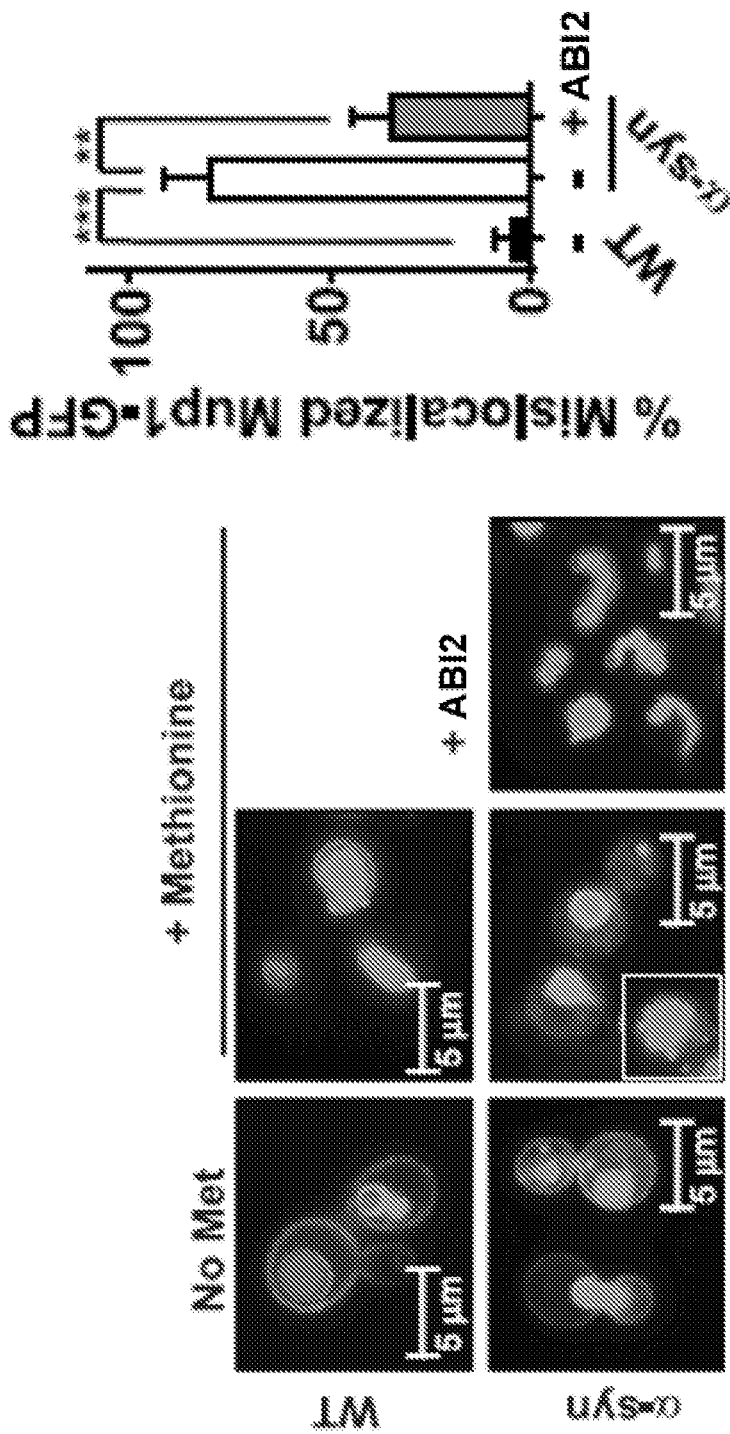
FIG. 14 shows that ABI2 directly antagonizes α-syn-induced endosomal defects. (A) Methionine-stimulated Mup1-GFP endocytosis in wild type or untagged α-syn strains with DMSO or ABI2. Pulse-labeling cells with FM4-64 during the first hour of α-syn expression marked the vacuole. (B) Effects of α-syn on Sna3-GFP localization. Immunoblot shows Sna3-GFP cleavage in response to α-syn and ABI2. FM4-64 labeling is as in (A). Arrows indicate stalled endosomal vesicles containing Sna3-GFP. (C) Pulse-labeling of FM4-64 of α-syn cells after 4 hours of expression in the presence or absence of ABI2. (D) Schematic of ABI2 mechanism in antagonizing core and secondary α-syn pathologies.
Figure 14B:
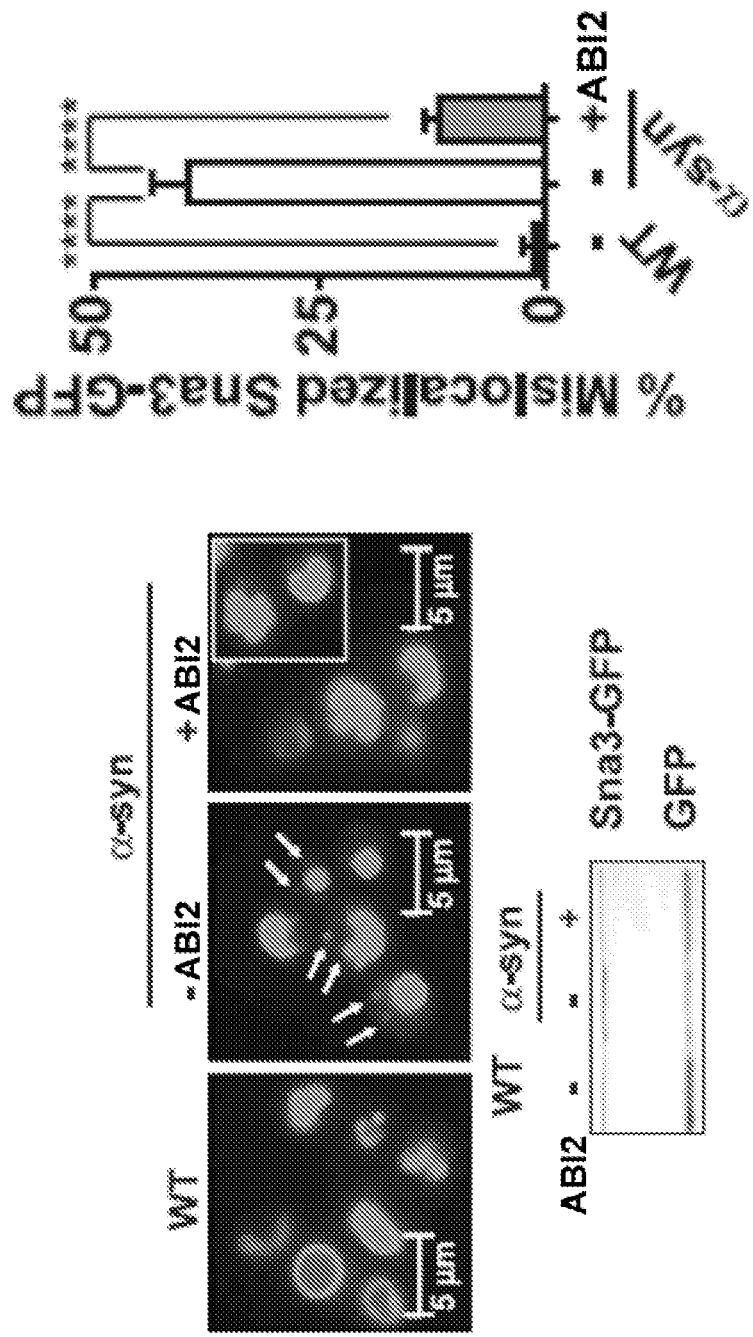

Example 10. ABI2 Directly Antagonizes α-Syn-Induced Endosomal Defects

α-Syn's effect on Mup1-GFP and Sna3-GFP trafficking was tested. Indeed, α-syn expression impeded both the methionine-induced transport of Mup1-GFP from the plasma membrane to the vacuole (FIG. 14A) and the constitutive trafficking of Sna3-GFP from the Golgi and the vacuole (FIG. 14B). Further, in the presence of α-syn, ABI2 restored trafficking of both substrates (FIG. 14A and FIG. 14B).

Figure 14C:
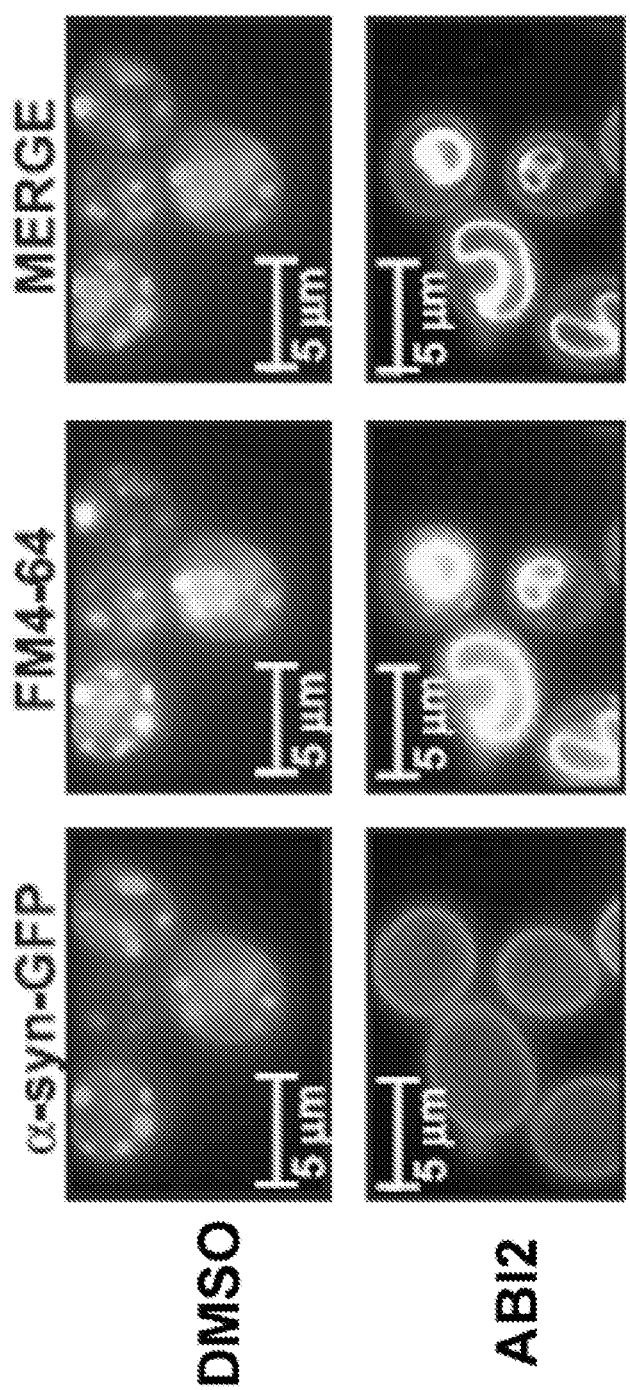
Figure 14D:
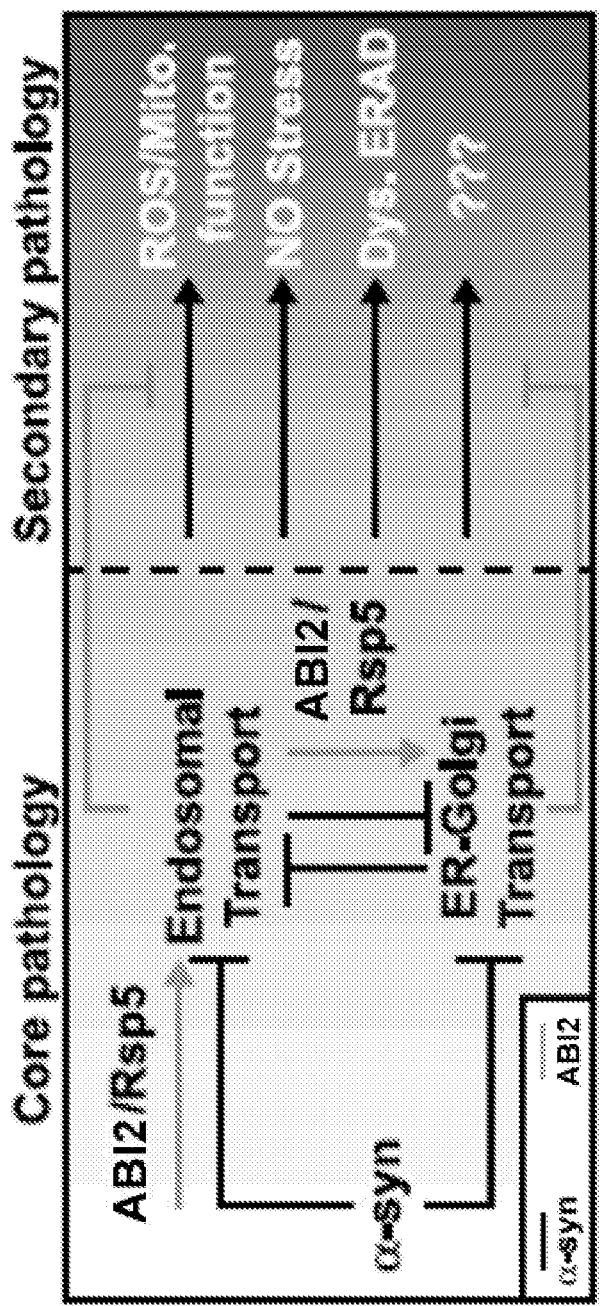

In addition to specific substrates, bulk endosomal transport from the plasma membrane to the vacuole was perturbed by α-syn (FIG. 4C) (T. F. Outeiro, S. Lindquist, Yeast cells provide insight into alpha-synuclein biology and pathobiology Science 302, 1772 (Dec. 5, 2003); A. D. Gitler et al., The Parkinson's disease protein alpha-synuclein disrupts cellular Rab homeostasis Proc Natl Acad Sci USA 105, 145 (Jan. 8, 2008); J. H. Soper, V. Kehm, C. G. Burd, V. A. Bankaitis, V. M. Lee, Aggregation of alpha-synuclein in S. cerevisiae is associated with defects in endosomal trafficking and phospholipid biosynthesis J Mol Neurosci 43, 391 (March, 2011)); Sancenon et al., Suppression of alpha-synuclein toxicity and vesicle trafficking defects by phosphorylation at S129 in yeast depends on genetic context Hum Mol Genet 21, 2432 (Jun. 1, 2012)). When FM4-64 was used to pulse-label the endosomal pathway, after prolonged α-syn expression, the dye strongly co-localized with α-syn inclusions and failed to reach the vacuole (FIG. 14C). ABI2 fully restored endocytosis and concomitantly reduced α-syn inclusions (FIG. 14C, bottom panels). Thus, the ability of ABI2 to promote Rsp5-dependent processes directly restored diverse cellular pathologies caused by α-syn, including both ER-to-Golgi and endosomal trafficking (FIG. 14D).

Rsp5/Nedd4 can ubiquitinate α-syn and Nedd4 localizes to Lewy Bodies in brain samples from PD patients (G. K. Tofaris et al., Ubiquitin ligase Nedd4 promotes alpha-synuclein degradation by the endosomal-lysosomal pathway Proc Natl Acad Sci USA 108, 17004 (Oct. 11, 2011)). However, α-syn levels were not altered by ABI2 in vivo. And, when tested in vitro, ABI2 did not affect the ubiquitination of α-syn and Sna3 by Rsp5. As noted, however, most of the complexities of Rsp5 in vivo activities have yet to be recapitulated in vitro. Thus, ABI2 exemplifies the ability of unbiased in vivo phenotypic screens to uncover chemical probes that cannot be discovered through simple target-based in vitro approaches. Likewise, ABI2 chemical genetics identify a deeply rooted biological node, Rsp5 that had not been identified previous overexpression or deletion screens. Notably, despite their central role in protein homeostasis and several human diseases, to date E3 ubiquitin ligases are virtually untouched by biological probes, let alone therapeutics.

The vesicular trafficking processes perturbed by α-syn and promoted by the compounds described herein are fundamental to all eukaryotic cells, yet are particularly important to neurons that rely heavily on efficient synaptic vesicle dynamics and regulated neurotransmitter release. Indeed, dysfunctional endosomal transport is emerging as contributing factor in α-syn pathology in human neurons. Altered cell biology, post-mortem pathology, and human genetic risk factors all implicate altered vesicular trafficking (A. A. Cooper et al., Alpha-synuclein blocks ER-Golgi traffic and Rab1 rescues neuron loss in Parkinson's models Science 313, 324 (Jul. 21, 2006); T. F. Outeiro, S. Lindquist, Yeast cells provide insight into alpha-synuclein biology and pathobiology Science 302, 1772 (Dec. 5, 2003); A. D. Gitler et al., The Parkinson's disease protein alpha-synuclein disrupts cellular Rab homeostasis Proc Natl Acad Sci USA 105, 145 (Jan. 8, 2008); J. H. Soper, V. Kehm, C. G. Burd, V. A. Bankaitis, V. M. Lee, Aggregation of alpha-synuclein in S. cerevisiae is associated with defects in endosomal trafficking and phospholipid biosynthesis J Mol Neurosci 43, 391 (March, 2011); V. Sancenon et al., Suppression of alpha-synuclein toxicity and vesicle trafficking defects by phosphorylation at S129 in yeast depends on genetic context Hum Mol Genet 21, 2432 (Jun. 1, 2012); G. Esposito, F. Ana Clara, P. Verstreken, Synaptic vesicle trafficking and Parkinson's disease Dev Neurobiol 72, 134 (January, 2012); D. A. Macleod et al., RAB7L1 Interacts with LRRK2 to Modify Intraneuronal Protein Sorting and Parkinson's Disease Risk Neuron 77, 425 (Feb. 6, 2013); C. Vilarino-Guell et al., VPS35 mutations in Parkinson disease Am J Hum Genet 89, 162 (Jul. 15, 2011); A. Zimprich et al., A mutation in VPS35, encoding a subunit of the retromer complex, causes late-onset Parkinson disease Am J Hum Genet 89, 168 (Jul. 15, 2011); P. Zabrocki et al., Phosphorylation, lipid raft interaction and traffic of alpha-synuclein in a yeast model for Parkinson Biochim Biophys Acta 1783, 1767 (October, 2008)). The ability of the compounds described herein to promote endosomal trafficking through Rsp5/Nedd4 and thus "reset" vesicle trafficking homeostasis, in turn, rescued several other, seemingly disparate, α-syn phenotypes. Identifying such deeply rooted pathways that ramify to affect multiple aspects of protein folding pathology may be useful for developing disease-modifying therapies.

REFERENCES

1. D. C. Swinney, J. Anthony, Nat Rev Drug Discov 10, 507 (July, 2011).
2. J. Kotz, Science-Business Exchange 15, (2012).
3. D. F. Tardiff, S. Lindquist, Drug Discovery Today: Technologies, (2012).
4. V. Khurana, S. Lindquist, Nat Rev Neurosci 11, 436 (June, 2010).
5. A. M. Smith, R. Ammar, C. Nislow, G. Giaever, Pharmacol Ther 127, 156 (August, 2010).
6. D. F. Tardiff, M. L. Tucci, K. A. Caldwell, G. A. Caldwell, S. Lindquist, J Biol Chem 287, 4107 (Feb. 3, 2012).
7. A. D. Gitler et al., Proc Natl Acad Sci USA 105, 145 (Jan. 8, 2008).
8. A. A. Cooper et al., Science 313, 324 (Jul. 21, 2006).
9. L. J. Su et al., Dis Model Mech 3, 194 (March-April, 2010).
10. M. L. Duennwald, S. Lindquist, Genes Dev 22, 3308 (Dec. 1, 2008).
11. T. F. Outeiro, S. Lindquist, Science 302, 1772 (Dec. 5, 2003).
12. A. B. Singleton et al., Science 302, 841 (Oct. 31, 2003).
13. P. M. Dexter, K. A. Caldwell, G. A. Caldwell, Neurotherapeutics 9, 393 (April, 2012).
14. A. Kumar, Methods Mol Biol 416, 117 (2008).
15. D. Rotin, S. Kumar, Nat Rev Mol Cell Biol 10, 398 (June, 2009).
16. H. C. Kim, A. M. Steffen, M. L. Oldham, J. Chen, J. M. Huibregtse, EMBO Rep 12, 334 (April, 2011).
17. F. Omura, Y. Kodama, T. Ashikari, FEMS Microbiol Lett 194, 207 (Jan. 15, 2001).
18. J. Ren, Y. Kee, J. M. Huibregtse, R. C. Piper, Mol Biol Cell 18, 324 (January, 2007).
19. S. Swaminathan, A. Y. Amerik, M. Hochstrasser, Mol Biol Cell 10, 2583 (August, 1999).
20. S. Dupre, R. Haguenauer-Tsapis, Mol Cell Biol 21, 4482 (July, 2001).
21. E. Yeger-Lotem et al., Nat Genet 41, 316 (March, 2009).
22. G. K. Tofaris et al., Proc Natl Acad Sci USA 108, 17004 (Oct. 11, 2011).
23. P. J. Plant, H. Yeger, O. Staub, P. Howard, D. Rotin, J Biol Chem 272, 32329 (Dec. 19, 1997).
24. R. Dunn, D. A. Klos, A. S. Adler, L. Hicke, J Cell Biol 165, 135 (April, 2004).
25. K. Jarmoszewicz, K. Lukasiak, H. Riezman, J. Kaminska, PLoS One 7, e39582 (2012).
26. C. M. Haynes, S. Caldwell, A. A. Cooper, J Cell Biol 158, 91 (Jul. 8, 2002).
27. G. Esposito, F. Ana Clara, P. Verstreken, Dev Neurobiol 72, 134 (January, 2012).
28. D. A. Macleod et al., Neuron 77, 425 (Feb. 6, 2013).
29. C. Vilarino-Guell et al., Am J Hum Genet 89, 162 (Jul. 15, 2011).
30. A. Zimprich et al., Am J Hum Genet 89, 168 (Jul. 15, 2011).
31. A. L. Barabasi, N. Gulbahce, J. Loscalzo, Nat Rev Genet 12, 56 (January, 2011).
32. C. Hein, J. Y. Springael, C. Volland, R. Haguenauer-Tsapis, B. Andre, Mol Microbiol 18, 77 (October, 1995).
33. S. Treusch et al., Science 334, 1241 (Dec. 2, 2011).

34. S. Ju et al., *PLoS Biol* 9, e1001052 (April, 2011).
35. Y. Hu et al., *Genome Res* 17, 536 (April, 2007).
36. J. A. Lewis, J. T. Fleming, *Methods Cell Biol* 48, 3 (1995).
37. S. Cao, C. C. Gelwix, K. A. Caldwell, G. A. Caldwell, *J Neurosci* 25, 3801 (Apr. 13, 2005).
38. F. Liu et al., *Free Radic Biol Med* 45, 242 (Aug. 1, 2008).
39. H. Li, R. Durbin, *Bioinformatics* 25, 1754 (Jul. 15, 2009).
40. M. A. DePristo et al., *Nat Genet* 43, 491 (May, 2011).
41. H. Thorvaldsdottir, J. T. Robinson, J. P. Mesirov, *Brief Bioinform*, (Apr. 19, 2012).
42. M. L. Duennwald, S. Jagadish, F. Giorgini, P. J. Muchowski, S. Lindquist, *Proc Natl Acad Sci USA* 103, 11051 (Jul. 18, 2006).
43. D. M. Gelperin et al., *Genes Dev* 19, 2816 (Dec. 1, 2005).
44. B. Sampaio-Marques et al., *Autophagy* 8, 1494 (October, 2012).
45. Y. J. Lee, S. Wang, S. R. Slone, T. A. Yacoubian, S. N. Witt, *PLoS One* 6, e15946 (2011).
46. V. Sancenon et al., *Hum Mol Genet* 21, 2432 (Jun. 1, 2012).
47. Y. Y. Sere, M. Regnacq, J. Colas, T. Berges, *Free Radic Biol Med* 49, 1755 (Dec. 1, 2010).
48. M. Kim et al., *Biochem Biophys Res Commun* 365, 628 (Jan. 25, 2008).
49. N. Sharma et al., *J Mol Neurosci* 28, 161 (2006).
50. T. R. Flower, L. S. Chesnokova, C. A. Froelich, C. Dixon, S. N. Witt, *J Mol Biol* 351, 1081 (Sep. 2, 2005).
51. J. H. Soper, V. Kehm, C. G. Burd, V. A. Bankaitis, V. M. Lee, *J Mol Neurosci* 43, 391 (March, 2011).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

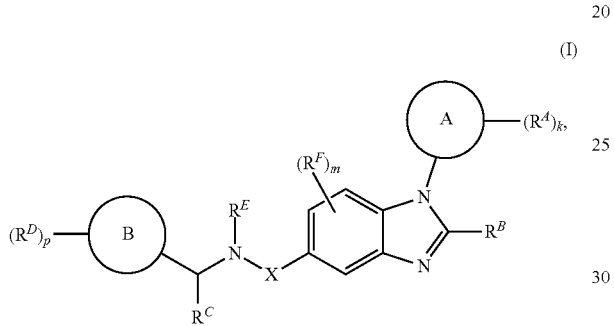

or a pharmaceutically acceptable salt, solvate, hydrate, polymorph, co-crystal, tautomer, stereoisomer, or isotopically labeled derivative thereof;
wherein:
Ring A is aryl;
Ring B is aryl;
X is —C(=O)—;
each instance of $R^4$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —SCN, —C(=$NR^{A1}$)$R^{A1}$, —C(=$NR^{A1}$)$OR^{A1}$, —C(=$NR^{A1}$)$N(R^{A1})_2$, —C(=O)$R^{A1}$, —C(=O)$OR^{A1}$, —C(=O)$N(R^{A1})_2$, —$NO_2$, —$NR^{A1}$C(=O)$R^{A1}$, —$NR^{A1}$C(O)$OR^{A1}$, —$NR^{A1}$C(=O)$N(R^{A1})_2$, —OC(=O)$R^{A1}$, —OC(=O)$OR^{A1}$, or —OC(=O)$N(R^{A1})_2$, or two $R^4$ groups are joined to form a substituted or unsubstituted carbocyclic, substituted or unsubstituted heterocyclic, substituted or unsubstituted aryl, or substituted or unsubstituted heteroaryl ring;
each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted heterocyclic ring;
$R^B$ is hydrogen, halogen, or substituted or unsubstituted $C_{1-6}$ alkyl;
$R^C$ is hydrogen, halogen, or substituted or unsubstituted $C_{1-6}$ alkyl;
each instance of $R^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{D1}$, —$N(R^{D1})_2$, —$SR^{D1}$, —CN, —SCN, —C(=$NR^{D1}$)$R^{D1}$, —C(=$NR^{D1}$)$OR^{D1}$, —C(=$NR^{D1}$)$N(R^{D1})_2$, —C(=O)$R^{D1}$, —C(=O)$OR^{D1}$, —C(=O)$N(R^{D1})_2$, —$NO_2$, —$NR^{D1}$C(=O)$R^{D1}$, —$NR^{D1}$C(=O)$OR^{D1}$, —$NR^{D1}$C(=O)$N(R^{D1})_2$, —OC(=O)$R^{D1}$, —OC(=O)$OR^{D1}$, or —OC(=O)$N(R^{D1})_2$;
each instance of $R^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom;
$R^E$ is hydrogen, substituted or unsubstituted $C_{1-6}$ alkyl, or a nitrogen protecting group;
each instance of $R^F$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{F1}$, —$N(R^{F1})_2$, —$SR^{F1}$, —CN, —SCN, —C(=$NR^{F1}$)$R^{F1}$, —C(=$NR^{F1}$)$OR^{F1}$, —C(=$NR^{F1}$)$N(R^F)_2$, —C(=O)$R^{F1}$, —C(=O)$OR^{F1}$, —C(=O)$N(R^{F1})_2$, —$NO_2$, —$NR^{F1}$C(=O)$R^{F1}$, —$NR^{F1}$C(=O)$OR^{F1}$, —$NR^{F1}$C(=O)$N(R^{F1})_2$, —OC(=O)$R^{F1}$, —OC(=O)$OR^{F1}$, or —OC(=O)$N(R^{F1})_2$, or two $R^F$ groups are joined to form a substituted or unsubstituted carbocyclic, substituted or unsubstituted heterocyclic, substituted or unsubstituted aryl, or substituted or unsubstituted heteroaryl ring;

each instance of $R^{F1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{F1}$ groups are joined to form a substituted or unsubstituted heterocyclic ring;

k is 1, 2, 3, 4, or 5;

p is 1, 2, 3, 4, or 5; and m is 0, 1, 2, or 3;

provided that at least one instance of $R^A$ or $R^D$ is not hydrogen; and provided that the compound is not

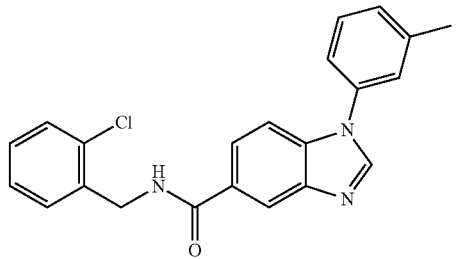

or

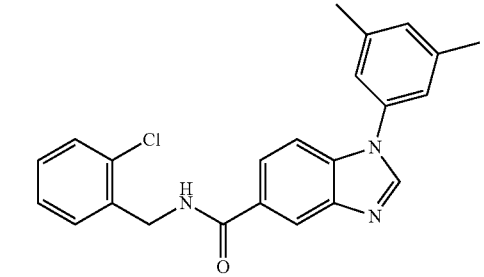

2. The compound of claim 1, wherein the compound is of the formula:

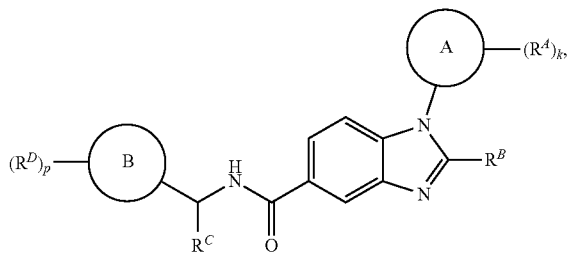

or a pharmaceutically acceptable salt thereof.

3. The compound of claim 1, wherein the compound is of the formula:

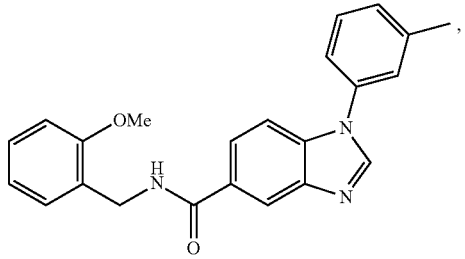

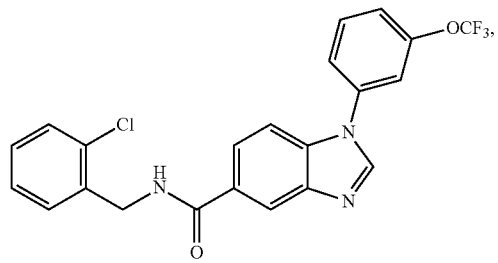

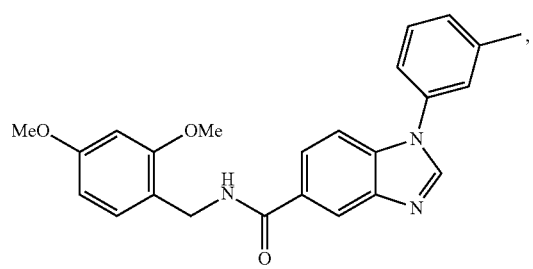

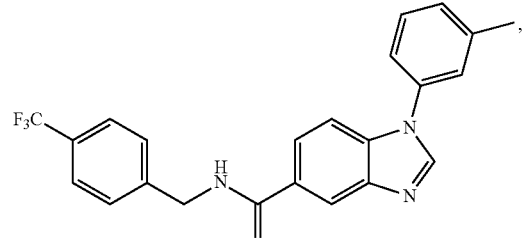

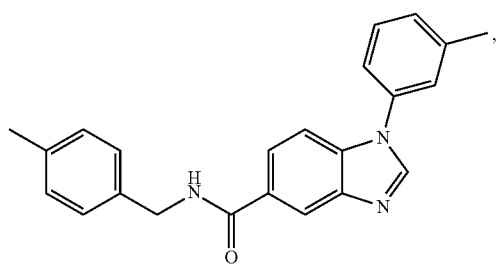

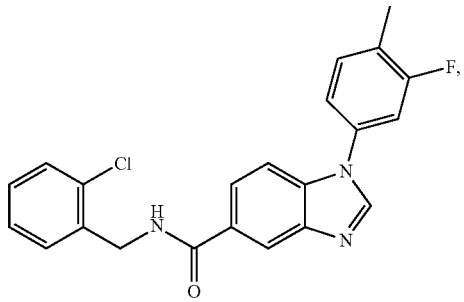

107
-continued
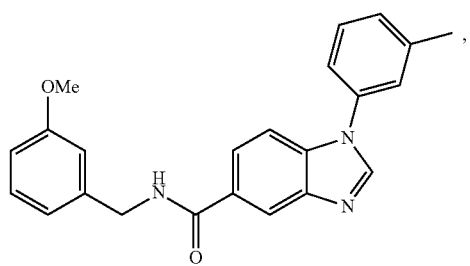
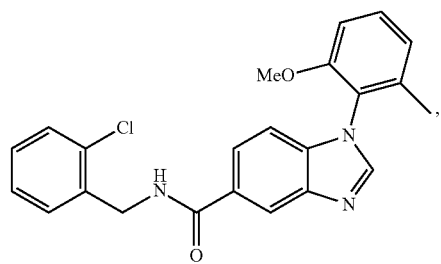
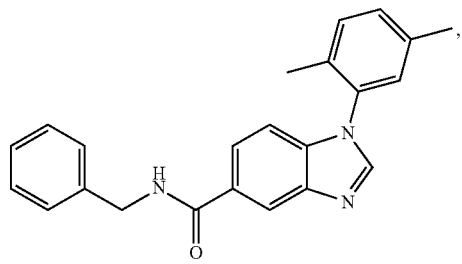
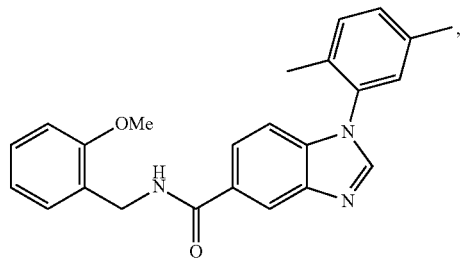
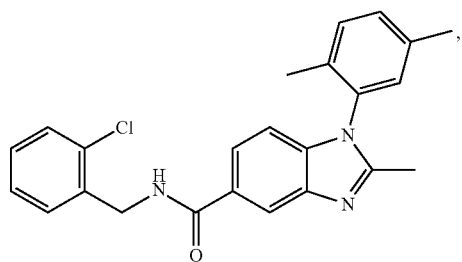
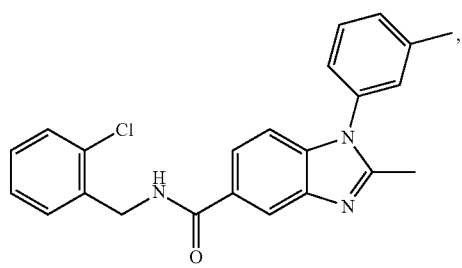
108
-continued
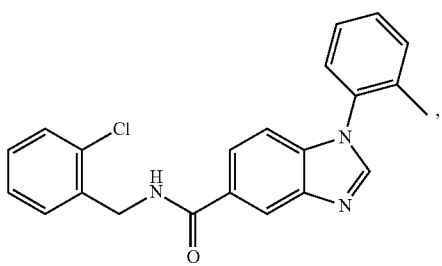
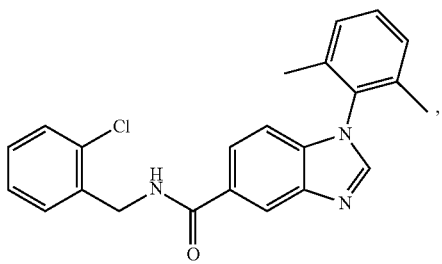
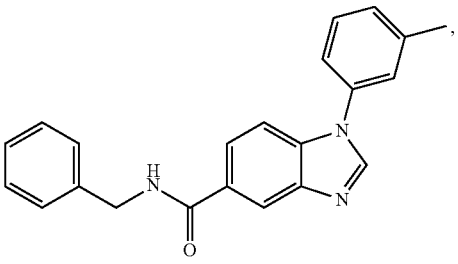
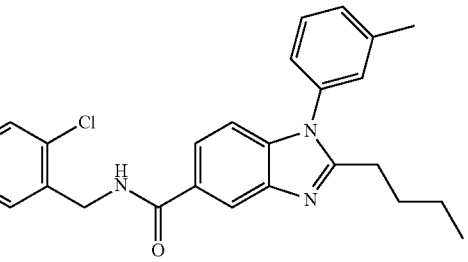
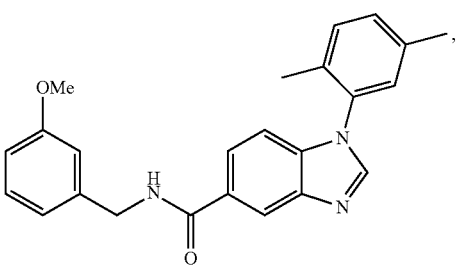
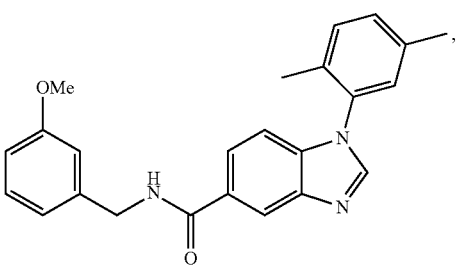

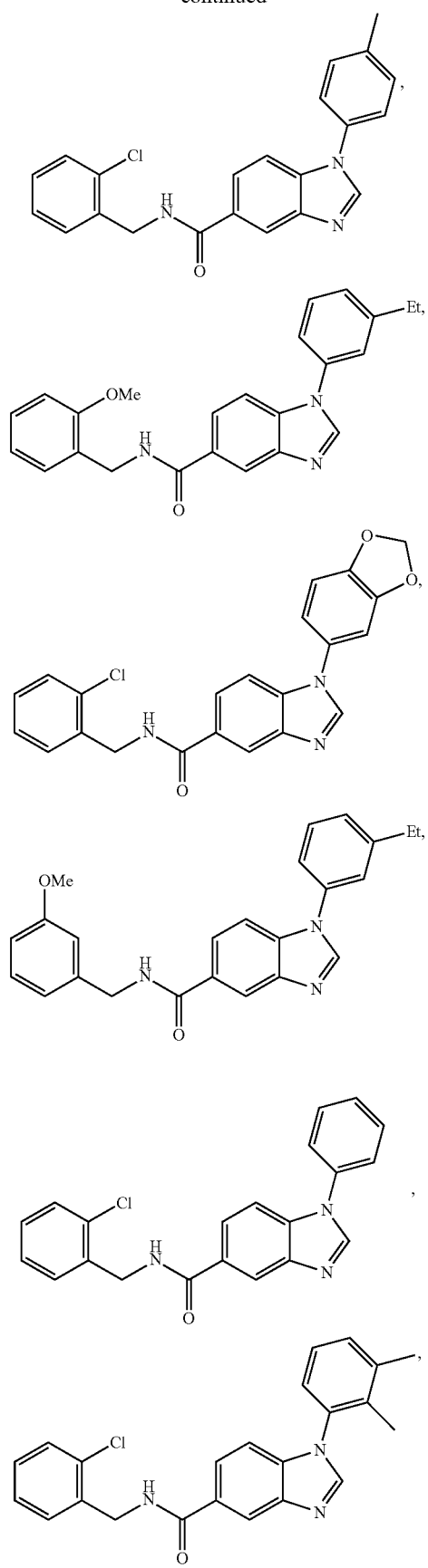
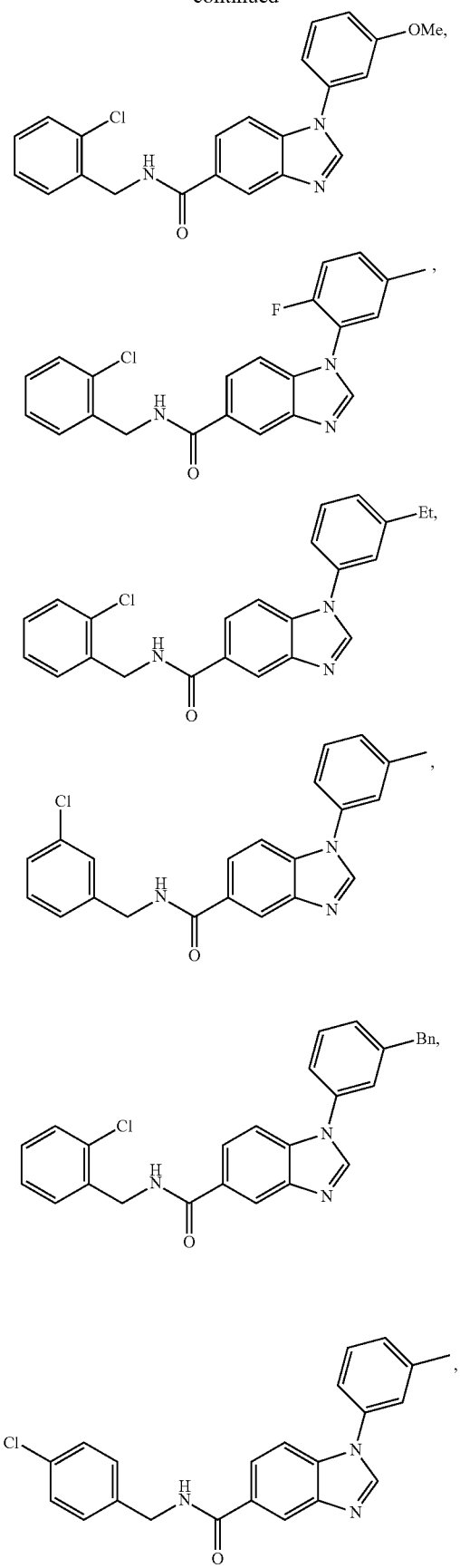

-continued

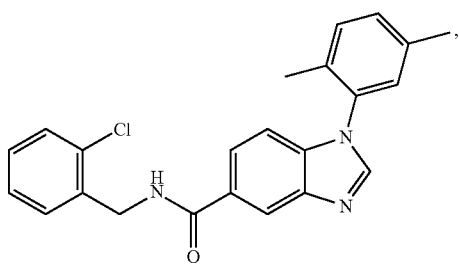

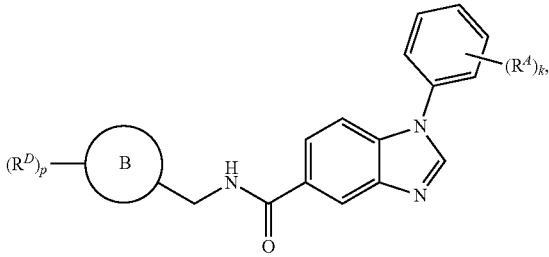

or a pharmaceutically acceptable salt thereof.

7. The compound of claim 1, wherein the compound is of the formula:

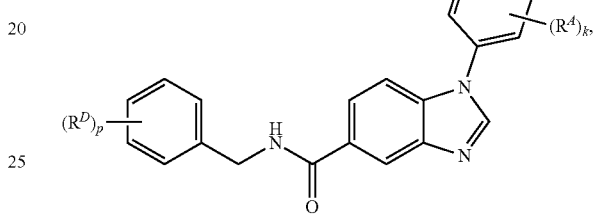

or a pharmaceutically acceptable salt thereof.

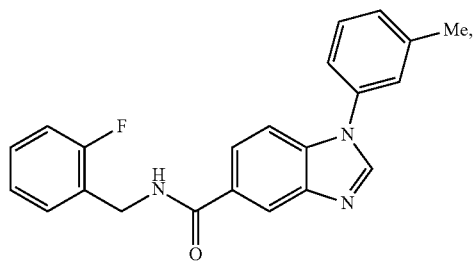

or a pharmaceutically acceptable salt thereof.

4. The compound of claim 1, wherein the compound is of the formula:

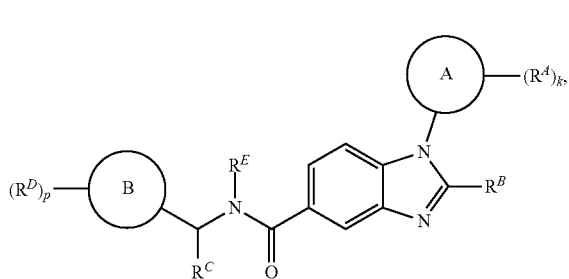

or a pharmaceutically acceptable salt thereof.

5. The compound of claim 1, wherein the compound is of the formula:

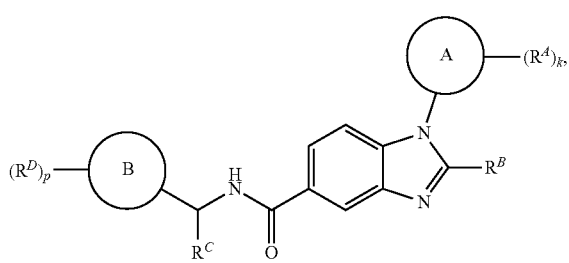

or a pharmaceutically acceptable salt thereof.

6. The compound of claim 1, wherein the compound is of the formula:

8. A pharmaceutical composition comprising a compound of claim 1 or a compound of the formula:

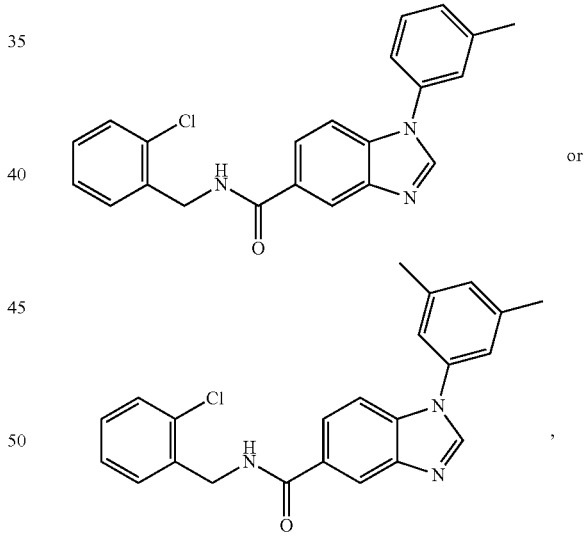

or a pharmaceutically acceptable salt thereof; and optionally a pharmaceutically acceptable excipient.

9. A method of treating a disease associated with protein aggregation in a subject in need thereof, wherein the disease is amyloidosis, Parkinson's disease, Alzheimer's disease, or a prion disease, the method comprising:
 administering to the subject a therapeutically or prophylactically effective amount of a compound of claim 1, or a pharmaceutically acceptable salt thereof.

10. The method of claim 9, wherein the subject is a human.

* * * * *

UNITED STATES PATENT AND TRADEMARK OFFICE
CERTIFICATE OF CORRECTION

PATENT NO. : 9,790,188 B2
APPLICATION NO. : 14/776184
DATED : October 17, 2017
INVENTOR(S) : Susan L. Lindquist et al.

Page 1 of 1

It is certified that error appears in the above-identified patent and that said Letters Patent is hereby corrected as shown below:

In the Claims

In Claim 5, at Column 111, Lines 54-64, the formula, should read:

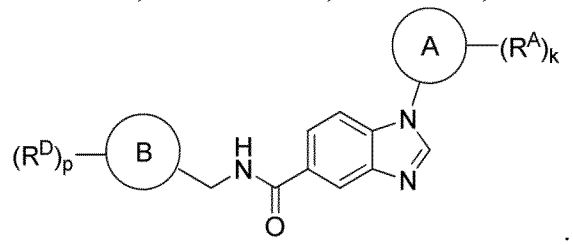

Signed and Sealed this
Eleventh Day of September, 2018

Andrei Iancu
*Director of the United States Patent and Trademark Office*

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1

His Ile Pro Pro Gly Asn Val Asp Pro Asp Arg His Asp Phe Pro Pro
1               5                   10                  15
```

```
Ser Tyr

<210> SEQ ID NO 2
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 2

Asn Ser Cys Tyr Met Asn Cys Ile Ile Gln Phe Ile Leu
1               5                   10
```